United States Patent [19]
Felthouse et al.

[11] Patent Number: 5,945,368
[45] Date of Patent: Aug. 31, 1999

[54] MOLYBDENUM-MODIFIED VANADIUM-PHOSPHORUS OXIDE CATALYSTS FOR THE PRODUCTION OF MALEIC ANHYDRIDE

[75] Inventors: Timothy R. Felthouse; Robert A. Keppel; Carl J. Schaefer, all of St. Louis, Mo.

[73] Assignee: Huntsman Petrochemical Corporation, Salt Lake City, Utah

[21] Appl. No.: 08/538,005

[22] Filed: Oct. 2, 1995

[51] Int. Cl.[6] .......................... B01J 27/198; B01J 27/199; B01J 27/19
[52] U.S. Cl. .......................... 502/209; 502/211; 502/305; 502/353
[58] Field of Search .......................... 502/209, 211, 502/305, 353

[56] References Cited

U.S. PATENT DOCUMENTS

| | | | |
|---|---|---|---|
| 3,919,257 | 11/1975 | Milberger et al. | 260/346.8 |
| 4,043,943 | 8/1977 | Schneider | 252/437 |
| 4,056,487 | 11/1977 | Kerr | 252/435 |
| 4,065,468 | 12/1977 | Grasselli et al. | 260/346 |
| 4,105,586 | 8/1978 | Kerr | 252/437 |
| 4,110,350 | 8/1978 | Umemura et al. | 260/346.75 |
| 4,147,661 | 4/1979 | Higgins et al. | 252/435 |
| 4,151,116 | 4/1979 | McDermott | 252/435 |
| 4,152,338 | 5/1979 | Kerr | 260/346.75 |
| 4,152,339 | 5/1979 | Kerr et al. | 260/346.75 |
| 4,153,577 | 5/1979 | Barone | 252/435 |
| 4,158,671 | 6/1979 | Barone | 260/546 |
| 4,167,516 | 9/1979 | Kerr | 260/346.75 |
| 4,172,084 | 10/1979 | Bremer | 260/346.75 |
| 4,177,161 | 12/1979 | Umemura et al. | 252/435 |
| 4,202,826 | 5/1980 | Kerr | 260/346.75 |
| 4,209,423 | 6/1980 | Hutchings et al. | 252/435 |
| 4,218,382 | 8/1980 | Milberger et al. | 260/346.75 |
| 4,219,484 | 8/1980 | Milberger et al. | 260/346.75 |
| 4,222,945 | 9/1980 | Higgins et al. | 260/346.75 |
| 4,225,465 | 9/1980 | Bremer | 252/435 |
| 4,244,878 | 1/1981 | McDermott | 260/346.75 |
| 4,288,372 | 9/1981 | Hutchings et al. | 260/346.75 |
| 4,317,777 | 3/1982 | Higgins et al. | 260/346.75 |

(List continued on next page.)

OTHER PUBLICATIONS

Ye, et al., Catalysis Today, "Effect of Additives on the Active Sites of (VO)$_2$P$_2$O$_7$ Catalysts," Apr. 1, 1993, vol. 16, No. 1, pp. 113–121.

Ye et al. "Number of Surface V=O Species of Promoted (VO)$_2$P$_2$O$_7$ Catalysts" Applied Catalysts, vol. 69 (1991) pp. L1–L5.

Ye et al. "Enhanced Activity of Promoted (VO)$_2$P$_2$O$_7$ by Preferential Exposure of the (020) Plane" J. Chem. Soc. Commun. (1990) pp. 1337–1338.

Bej et al. "Selective Oxidation of n–Butane to Maleic Anhydride. 1. Optimization Studies" Ind. Eng. Chem. Res., vol. 30 (1991) pp. 1819–1824.

Bej et al. "Selective Oxidation of n–Butane to Maleic Anhydride, A Comparative Study Between Promoted and Unpromoted VPO Catalysts" Appl. Catalysis A: General, vol. 83 (1992) pp. 149–163.

*Primary Examiner*—Michael Lewis
*Assistant Examiner*—Alexander G. Ghyka
*Attorney, Agent, or Firm*—Senniger Powers Leavitt & Roedel

[57] ABSTRACT

An active catalyst having a crystal structure corresponding to that of a catalyst that has been prepared and activated by the following process. A substantially pentavalent vanadium-containing compound is reacted with a pentavalent phosphorus-containing compound in an alcohol medium capable of reducing the vanadium to an oxidation state of less than +5. Molybdenum is incorporated into the product of the reaction, thereby forming a solid molybdenum-modified precursor composition. The alcohol is removed to produce a dried solid molybdenum-modified precursor composition. Shaped bodies comprising said dried solid molybdenum-modified precursor composition are formed. The dried formed molybdenum-modified catalyst precursor composition is activated to transform it into the active catalyst.

108 Claims, 13 Drawing Sheets

U.S. PATENT DOCUMENTS

| | | | |
|---|---|---|---|
| 4,396,535 | 8/1983 | Bremer et al. | 252/435 |
| 4,400,522 | 8/1983 | Lemanski et al. | 549/260 |
| 4,416,802 | 11/1983 | Udovich et al. | 502/209 |
| 4,416,803 | 11/1983 | Udovich et al. | 502/209 |
| 4,418,003 | 11/1983 | Udovich et al. | 502/209 |
| 4,448,893 | 5/1984 | Bremer et al. | 502/209 |
| 4,465,846 | 8/1984 | Bremer et al. | 549/260 |
| 4,510,259 | 4/1985 | Udovich et al. | 502/209 |
| 4,596,878 | 6/1986 | Click et al. | 549/259 |
| 4,649,205 | 3/1987 | Edwards et al. | 549/260 |
| 4,732,885 | 3/1988 | Edwards et al. | 502/209 |
| 4,748,140 | 5/1988 | Blum et al. | 502/209 |
| 4,824,819 | 4/1989 | Edwards et al. | 502/209 |
| 4,845,241 | 7/1989 | Edwards et al. | 549/260 |
| 4,855,459 | 8/1989 | Mummey | 549/260 |
| 4,933,312 | 6/1990 | Haddad et al. | 502/209 |
| 4,950,769 | 8/1990 | McCandless et al. | 549/257 |
| 4,957,894 | 9/1990 | Haddad et al. | 502/209 |
| 4,965,235 | 10/1990 | Haddad et al. | 502/209 |
| 4,996,179 | 2/1991 | Haddad et al. | 502/209 |
| 5,011,945 | 4/1991 | Taheri | 549/260 |
| 5,019,545 | 5/1991 | Haddad et al. | 502/209 |
| 5,070,060 | 12/1991 | Barone | 502/209 |
| 5,093,298 | 3/1992 | Haddad et al. | 502/209 |
| 5,095,125 | 3/1992 | Haddad et al. | 549/259 |
| 5,134,106 | 7/1992 | Haddad et al. | 502/209 |
| 5,137,860 | 8/1992 | Ebner et al. | 502/209 |
| 5,158,923 | 10/1992 | Barone | 502/209 |
| 5,262,548 | 11/1993 | Barone | 549/262 |
| 5,275,996 | 1/1994 | Andrews et al. | 502/209 |
| 5,280,003 | 1/1994 | Bortinger | 502/209 |
| 5,296,436 | 3/1994 | Bortinger | 502/209 |
| 5,330,954 | 7/1994 | Cadot et al. | 502/209 |
| 5,364,824 | 11/1994 | Andrews et al. | 502/209 |
| 5,506,187 | 4/1996 | Haddad et al. | 502/209 |
| 5,543,532 | 8/1996 | Kourtakis et al. | 549/260 |
| 5,641,722 | 6/1997 | Mitchell et al. | 502/209 |

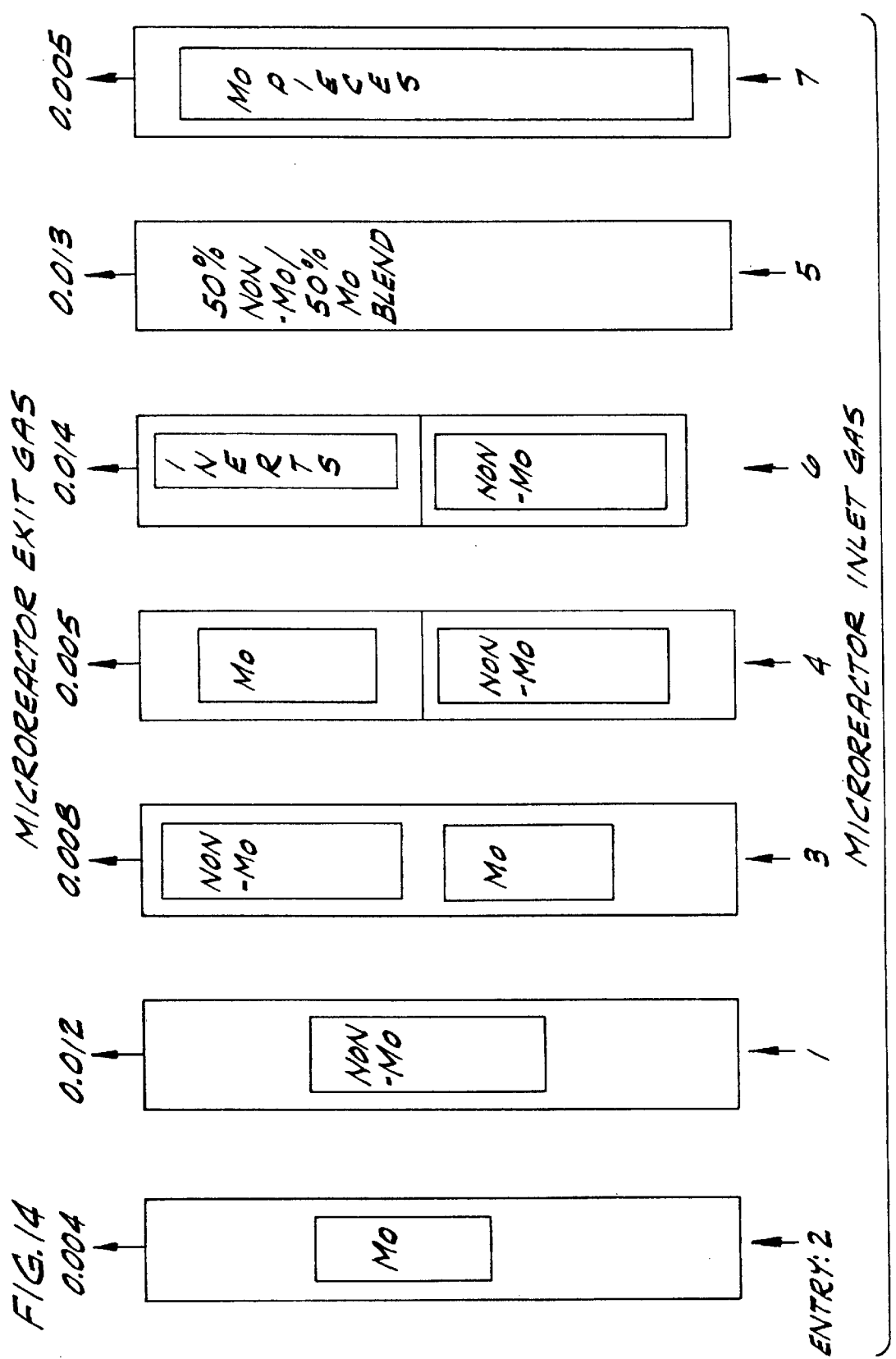

MOLYBDENUM-MODIFIED VANADIUM-PHOSPHORUS OXIDE CATALYSTS FOR THE PRODUCTION OF MALEIC ANHYDRIDE

BACKGROUND OF THE INVENTION

This invention relates to novel catalysts for the selective vapor phase oxidation of a hydrocarbon to a dicarboxylic anhydride and processes for the manufacture of these catalysts.

Maleic anhydride and other dicarboxylic anhydrides are commercially manufactured by vapor phase oxidation of a hydrocarbon such as n-butane as the hydrocarbon flows through a fixed bed reactor containing vanadium-phosphorus oxide catalyst. During the process, acrylic acid, acetic acid, carbon monoxide, and carbon dioxide are formed as by-products of the reaction. In butane-based maleic anhydride plants, downstream process equipment such as heat exchangers and distillation trays from the fixed bed reactor are often fouled after prolonged operation with a polyacrylic polymer derived from accumulation and reaction of acrylic acid. Such fouling is particularly acute in plants operating with aqueous-based maleic anhydride recovery processes where the acrylic acid polymerizes and obstructs distillation trays, reducing the performance of the distillation column. There has been a need for an improved catalyst that inhibits the formation of acrylic acid by-product while preserving maleic anhydride yield.

Procedures for the preparation of catalysts comprised of vanadium-phosphorus oxide are disclosed and taught in the prior art. Many references teach that it is preferable to reduce the vanadium to the tetravalent state in solution. Such catalysts are prepared by contacting vanadium and phosphorus compounds under conditions where substantial reduction to the tetravalent state of vanadium occurs to form the catalyst precursor. In many instances, promoter elements are also included in the catalyst precursor. The catalyst precursor is recovered, dried, and calcined to produce the catalyst.

It is generally recognized that the most desirable catalysts contain a substantial proportion of vanadyl pyrophosphate, a compound represented by the formula $(VO)_2P_2O_7$ whose X-ray diffraction pattern exhibits primary peaks at d-spacings of 3.86, 3.14 and 2.98 Å. Numerous references in the patent and open literature also discuss the incorporation of various metal ions as promoters in vanadium phosphorus oxide catalysts. A very wide variety of metal ions has been proposed for such purpose, and data have been published indicating a beneficial effect on yields or selectivity. Most of the literature does not speculate on how the promoters operate to enhance catalyst performance. However, some theories have been advanced. A survey article by Hutchings, "Effect of Promoters and Reactant Concentration on the Selective Oxidation of n-Butane to Maleic Anhydride Using Vanadium Phosphorus Oxide Catalysts," *Applied Catalysis* 72(1991), pp. 1–32 suggests that promoters serve a two fold function: to enable the formation of required vanadium phosphorus oxide ("VPO") compounds while decreasing the formation of deleterious phases; and to enable the formation of solid solutions which regulate the catalytic activity of the solid phase. Hutchings reports that promoter to vanadium molar ratios of 0.15 to 0.20 are considered to provide optimum results, though one study is adverted to in which favorable results were obtained with an Mo/V ratio of 0.04.

The Hutchings article further notes that the impregnation of a VPO catalyst with a promoter may increase the surface area. However, this reference does not mention, or indicate any significance to, the point at which surface area is measured. Nor does it suggest an effect of a promoter on the surface area of the catalyst. Most of the article concentrates on the reported effect of various promoters on the specific activity of a catalyst of a given area.

U.S. Pat. No. 4,043,943 describes vanadium-phosphorus oxides isolated from organic solutions which may contain minor amounts of molybdenum as a promoter. Molybdenum oxides are added at the 0.05 to 0.10 level and increase the surface areas of the catalysts after equilibration in a butane-oxygen gas stream.

U.S. Pat. Nos. 4,056,487, 4,105,586, 4,152,338, 4,152,339, 4,153,577, 4,158,671, 4,167,516 and 4,202,826 disclose catalyst disclose VPO catalyst complexes with several modifier elements selected from Mo, Cu, Ni, Co, Cr, Hf, Nb, Li, Re, Ru, Ba, Nd, Cb, Ce, and Y prepared from aqueous hydrochloric acid solution to which various amounts of oxalic acid and isopropyl alcohol are added. The ratio of molybdenum is 0.0025–0.04 mole per mole vanadium. Catalysts having a 0.010–0.012 Mo/V molar ratio were reported. Catalysts of this invention are said to produce molar yields of maleic anhydride from n-butane from 28.0 to 57.4% with salt bath temperatures from 388 to 450° C.

U.S. Pat. No. 4,065,468 describes a process for the production of maleic anhydride from n-butane using a catalyst that contains the oxides of vanadium, phosphorus, molybdenum, antimony, and various promoter elements such as nickel, bismuth, and titanium. Catalysts are reported having a Mo/V molar ratio of 2–12.1 $m^2/g$.

U.S. Pat. Nos. 4,110,350 and 4,177,161 give a process for oxidizing unsaturated hydrocarbons having 4 to 6 carbon atoms to maleic anhydride using a catalyst comprised of vanadium-phosphorus oxides and titanium with optional other elements including molybdenum in a Mo/V molar ratio of 0–1. The aqueous-prepared catalysts are said to produce yields of around 66% to maleic anhydride from 1,3-butadiene at 100% conversion and 450° C. One such reported catalyst had a molar ratio of Mo/V of 0.1.

U.S. Pat. No. 4,147,661 describes VPO catalysts modified with molybdenum in an atomic Mo/V ratio of 0.005–0.5 as prepared in an isobutanol and hydrogen chloride gas medium. Catalysts having an atomic Mo/V ratio of 0.03–0.05 are reported as providing a surface area of 16–24 $m^2/g$ for the calcined catalyst.

U.S. Pat. Nos. 4,151,116 and 4,244,878 describe catalysts containing vanadium-phosphorus oxide and a post-deposited promoter selected from elements that include molybdenum in a Mo/V atomic ratio of 0.12. All catalysts and their promoters are made in aqueous hydrochloric acid. Reported molar yields of maleic anhydride for the catalysts of this invention range from 32.0 to 48.8% with selectivities of 40.0 to 61.0% and salt bath temperatures of 410 to 500° C.

U.S. Pat. Nos. 4,172,084, 4,218,382, 4,219,484, and 4,225,465 describe catalysts of vanadium, phosphorus and uranium formed from aqueous oxide slurries that include promoter elements such as molybdenum in a Mo/V atomic ratio of 0.01–5, preferably 0.05.

U.S. Pat. Nos. 4,209,423 and 4,288,372 disclose catalysts containing vanadium, phosphorus and promoters such as molybdenum which are prepared from hydrochloric acid solutions. The molar ratio of molybdenum to vanadium ranges from 0.0015 to 1. A catalyst precursor prepared at a Mo/V ratio of 0.082 is reported to have a Mo/V atomic ratio of 0.043 in the dried solid. The final catalyst is reported to have a surface area of 9 m$^2$/g and gave a 55% molar pass yield of maleic anhydride at an n-butane conversion of 75%, 420° C., 1000/hr. of 1.5% n-butane in are at atmospheric pressure.

U.S. Pat. Nos. 4,222,945 and 4,317,777 describe a catalyst prepared by forming a VPO precursor in an aqueous hydrochloric acid medium, drying the solid precursor, boiling the solid to form a suspension, filtering the solid from the suspension, drying the solid, and mixing the solid with molybdenum trioxide at a Mo/V atomic ratio of 0.025. The resulting solid is ball milled, pelleted, crushed and sieved to give 500–700μ particles prior to calcination at 385° C. in a 1.5% n-butane/air mixture at 1000/hr GHSV. The final catalyst is reported to have a surface area of 32 m$^2$/g.

U.S. Pat. Nos. 4,396,535 and 4,465,846 disclose vanadium-phosphorus oxide catalyst precursors prepared in an aqueous slurry which are dried, crushed, slurried in alcohol, filtered, dried and calcined. Promoters such as molybdenum can be added to the precursor after drying or to the catalyst after calcination.

U.S. Pat. No. 4,400,522 describes vanadium-phosphorus oxide catalysts prepared from isobutanol with the addition of various promoter elements including molybdenum at a promoter to vanadium ratio of 0–0.5.

U.S. Pat. Nos. 4,416,802, 4,416,803, 4,418,003 4,510,259 and 4,748,140 describe VPO catalyst modified with a cometal such as molybdenum in a molar Mo/V ratio of 0.001–0.4. The catalysts are prepared from an aqueous hydrochloric acid solution. Catalysts having a molar Mo/V ratio of 0.03 are reported.

U.S. Pat. No. 4,596,878 discloses a method for regeneration of VPO catalysts which may contain molybdenum in a molar Mo/V ratio of 0.001–0.4.

U.S. Pat. No. 4,649,205 discloses a process for the reactivation of a vanadium-phosphorus oxide catalyst promoted by metals from a group that includes molybdenum in an atomic ratio of Mo to V of 0.005 to 0.25. The catalysts benefit by the use of water/ trialkylphosphate mixtures fed to the reactor with n-butane/air. Molar yields of 47.9 to 54.4% maleic anhydride are disclosed for catalysts having a Mo/V ratio of 0.03 with per day productivities ranging from 0.79 to 1.76 lb.-maleic anhydride/lb.-catalyst.

U.S. Pat. No. 4,732,885 describes a process for the manufacture of vanadium-phosphorus oxide (VPO) catalysts using a cometal as a promoter from a group that includes molybdenum. The cometal/vanadium ratio may range from 0.001 to 0.4. The promoted catalysts are used in the production of maleic anhydride from n-butane. The catalyst is prepared from an organic ether solvent containing a phosphoryl chloride in the presence of water or an aliphatic alcohol. The catalyst is activated in a gas stream of n-butane and water. Molybdenum-promoted VPO catalyst having a Mo/V molar ratio of 0.03 reportedly displayed a yield ranging from 77 to 103% maleic anhydride when a 1.1 to 1.5% n-butane gas stream was passed over the catalyst at a temperature between 375 and 440° C. and 1200/hr. to 2000/hr. space velocity. The surface area of one of the molybdenum-promoted catalysts was reportedly 40 m$^2$/g.

U.S. Pat. No. 4,824,819 discloses catalysts for the production of maleic anhydride which are comprised of vanadium-phosphorus oxide and a cometal such as molybdenum. A vanadium compound is deposited on top of the PO/cometal composition to give the final catalyst. Catalysts of this invention having a Mo/V molar ratio of 0.03 are described as exhibiting 72–89% conversion of a 1.1% n-butane/air feed at 1200/hr. space velocity at 431–445° C. with 80–94% molar yield of maleic anhydride.

U.S. Pat. No. 4,950,769 describes a process for vapor phase oxidation of n-butane to maleic anhydride by a vanadium-phosphorus oxide catalyst containing a cometal selected from a group that includes molybdenum in a Mo/V molar ratio of 0.001 to 0.2. A peroxide is added to the reactor gas stream to improve the catalyst operation. A molybdenum-promoted catalyst was reportedly prepared by an aqueous process wherein the Mo/V molar ratio was about 0.03.

U.S. Pat. Nos. 4,933,312, 4,957,894, 4,965,235, 4,996, 179, 5,093,298, and 5,095,125 disclose processes for the manufacture of catalysts used for maleic anhydride production. The catalysts are comprised of vanadium-phosphorus oxide and contain a cometal as a promoter from a group that includes molybdenum at a Mo/V molar ratio of 0.001–0.2. Catalysts prepared by the aqueous processes of the invention do not exhibit more than 2% expansion when activated for the oxidation of n-butane to make maleic anhydride. Catalysts having a Mo/V molar ratio of 0.03 are reported as producing molar yields of maleic anhydride around 53% for a 1.1% n-butane stream passing over the catalyst at 1200/hr. space velocity.

U.S. Pat. Nos. 5,011,945, 5,019,545, and 5,134,106 describe VPO catalysts containing a modifier such as molybdenum in a molar Mo/V ratio of 0.001–0.2. Catalysts prepared by the reaction of a vanadium compound and a phosphoryl halide in an aqueous medium are reported which have a molar Mo/V ratio of 0.06.

U.S. Pat. Nos. 5,070,060, 5,158,923 and 5,262,548 describe VPO catalysts containing Li, Zn and Mo promoters prepared in an aqueous hydrochloric acid solution. The molar Mo/V ratio ranges from 0.005–0.025. The reported catalysts having a Mo/V molar ratio of 0.0065, 0.013 or 0.026 provide a surface area of 3.9–11.4 m$^2$/g for the tableted catalyst.

U.S. Pat. Nos. 5,280,003 and 5,296,436 disclose VPO catalysts promoted with Li, Zn and Mo prepared in anhydrous isobutanol medium wherein the Mo/V ratio ranges from 0.005–0.025. Catalysts having a molar Mo/V ratio of 0.013–0.016 are reported.

Thus, it has long been known that various promoters including molybdenum can be added to VPO catalysts to obtain improved performance. Numerous patents from the 1980s as described above disclose the benefit of molybdenum addition in preparing aqueous derived catalysts. Since then, VPO catalysts prepared in aqueous media have been outpaced by catalysts prepared in non-aqueous media. See the Hutchings article discussed above. As indicated by the above cited patents, molybdenum has been suggested for VPO catalysts prepared in non-aqueous systems, in optimal Mo/V ratios of about 0.01–0.05.

SUMMARY OF THE INVENTION

Accordingly, among the several objects of the invention are the provision of a molybdenum-modified vanadium phosphorus oxide catalyst which minimizes the acrylic acid content of the reaction product gas produced in the catalytic oxidation of a hydrocarbon to a dicarboxylic acid anhydride; the provision of such a catalyst having high developed surface area, activity, selectivity, and productivity; the provision of such a catalyst in a shaped body form suitable for use in a commercial fixed or fluid bed reactor for the preparation of maleic anhydride; the provision of such a shaped body catalyst which preserves maleic anhydride yield; the provision of such a catalyst having enhanced catalyst life in a commercial fixed or fluid bed reactor; the provision of such a catalyst which is used without necessitating major capital alterations of existing plant equipment; the provision of such a catalyst which improves the performance of aqueous-based maleic anhydride recovery processes; and the provision of improved methods for producing molybdenum-modified VPO catalyst precursors and activated molybdenum-modified VPO catalyst, especially in shaped body form suitable for use in a commercial fixed bed reactor.

Briefly, therefore, the present invention is directed to an active catalyst having a crystal structure corresponding to that of a catalyst that has been prepared and activated by the following process. A substantially pentavalent vanadium-containing compound is reacted with a pentavalent phosphorus-containing compound in an alcohol medium capable of reducing the vanadium to an oxidation state of less than +5. Molybdenum is incorporated into the product of the reaction, thereby forming a solid molybdenum-modified precursor composition. The alcohol is removed to produce a dried solid molybdenum-modified precursor composition. Shaped bodies comprising the dried solid molybdenum-modified precursor composition are formed. The dried formed molybdenum-modified catalyst precursor composition is activated to transform it into the active catalyst.

The invention is further directed to an active, phosphorus vanadium oxide catalyst for the conversion to maleic anhydride of a non-aromatic hydrocarbon having at least four carbon atoms in a straight chain. The catalyst comprises a shaped body having a volume of at least about 0.02 cc and a B.E.T. surface area of at least about 15 m$^2$/g. The catalyst contains molybdenum and has a molar ratio of molybdenum to vanadium of between about 0.0020 and about 0.0060.

The invention is still further directed to an active catalyst for conversion to maleic anhydride of a non-aromatic hydrocarbon having at least four carbon atoms in a straight chain. The catalyst comprises phosphorus, vanadium, oxygen, and molybdenum and has a macrostructure predominantly consisting of radially oriented three-dimensional networks of randomly shaped open cells. The molybdenum is concentrated at the surfaces of the walls of the cells.

The invention is also directed to an active catalyst having a crystal structure corresponding to that of a catalyst that has been prepared and activated by the following process. A phosphorus vanadium oxide powder and a molybdenum-containing powder are blended to form a molybdenum-modified catalyst precursor composition. The molybdenum-modified catalyst precursor composition is formed into shaped bodies, each of the shaped bodies having a volume of at least about 0.02 cc. The formed molybdenum-modified catalyst precursor composition is then activated to transform it into the active catalyst.

The invention includes a further process for the preparation of an active catalyst. In the process, a substantially pentavalent vanadium-containing compound is reacted with a pentavalent phosphorus-containing compound in an alcohol medium capable of reducing the vanadium to an oxidation state of less than +5. Molybdenum is incorporated into the product of the reaction, thereby forming a solid molybdenum-modified precursor composition. The alcohol is removed to produce a dried solid molybdenum-modified precursor composition. Shaped bodies comprising the dried solid molybdenum-modified precursor composition are formed. The dried formed molybdenum-modified catalyst precursor composition is activated to transform it into the active catalyst.

The invention is further directed to a process for the preparation of an active catalyst. In the process, a phosphorus vanadium oxide powder and a molybdenum-containing powder are blended to form a molybdenum-modified catalyst precursor composition. The molybdenum-modified catalyst precursor composition is formed into shaped bodies, each of the shaped bodies having a volume of at least about 0.02 cc. The formed molybdenum-modified catalyst precursor composition is then activated to transform it into the active catalyst.

The invention is further directed to a method for producing a maleic anhydride reaction product gas having a low acrylic acid content. The method comprises passing a gas stream initially comprising a mixture of a nonaromatic hydrocarbon having at least four carbon atoms in a straight chain and a molecular oxygen-containing gas over a fixed catalyst bed. The bed has a first zone containing an active catalyst and a second zone containing the active catalyst of the present invention downstream of the first zone.

The invention is also directed to a method for producing maleic anhydride reaction product gas having a low acrylic acid content. The method comprises passing a gas stream initially comprising a mixture of nonaromatic hydrocarbon having at least four carbon atoms in a straight chain and a molecular oxygen-containing gas over a fixed catalyst bed. The bed contains an active catalyst consisting essentially of the catalyst of the present invention as the sole catalyst.

The invention is further directed to a fixed catalyst bed adapted for the production of maleic anhydride by passage therethrough of a gas stream initially comprising a mixture of a nonaromatic hydrocarbon having at least four carbon atoms in a straight chain and an oxygen containing gas. The catalyst bed comprises a first zone containing a phosphorous vanadium oxide catalyst substantially devoid of active sites comprising molybdenum, and a second zone downstream of the first zone with respect to the flow of the gas stream. The second zone comprises the active catalyst of the present invention.

The invention is still further directed to a fixed catalyst bed adapted for the production of maleic anhydride by passage therethrough of a gas stream initially comprising a mixture of a nonaromatic hydrocarbon having at least four carbon atoms in a straight chain and an oxygen containing gas. The catalyst bed comprises a mixture of the active catalyst of the present invention and a phosphorous vanadium oxide catalyst substantially-devoid of active sites comprising molybdenum.

Other objects and features will be in part apparent and in part pointed out hereinafter.

BRIEF DESCRIPTION OF THE DRAWINGS

FIG. 14 depicts several catalyst pack configurations and the acrylic acid content of the microreactor exit gas at 85% butane conversion of 2.4% butane.

Corresponding reference characters indicate corresponding parts throughout the drawings.

DESCRIPTION OF THE PREFERRED EMBODIMENTS

Figure 1:
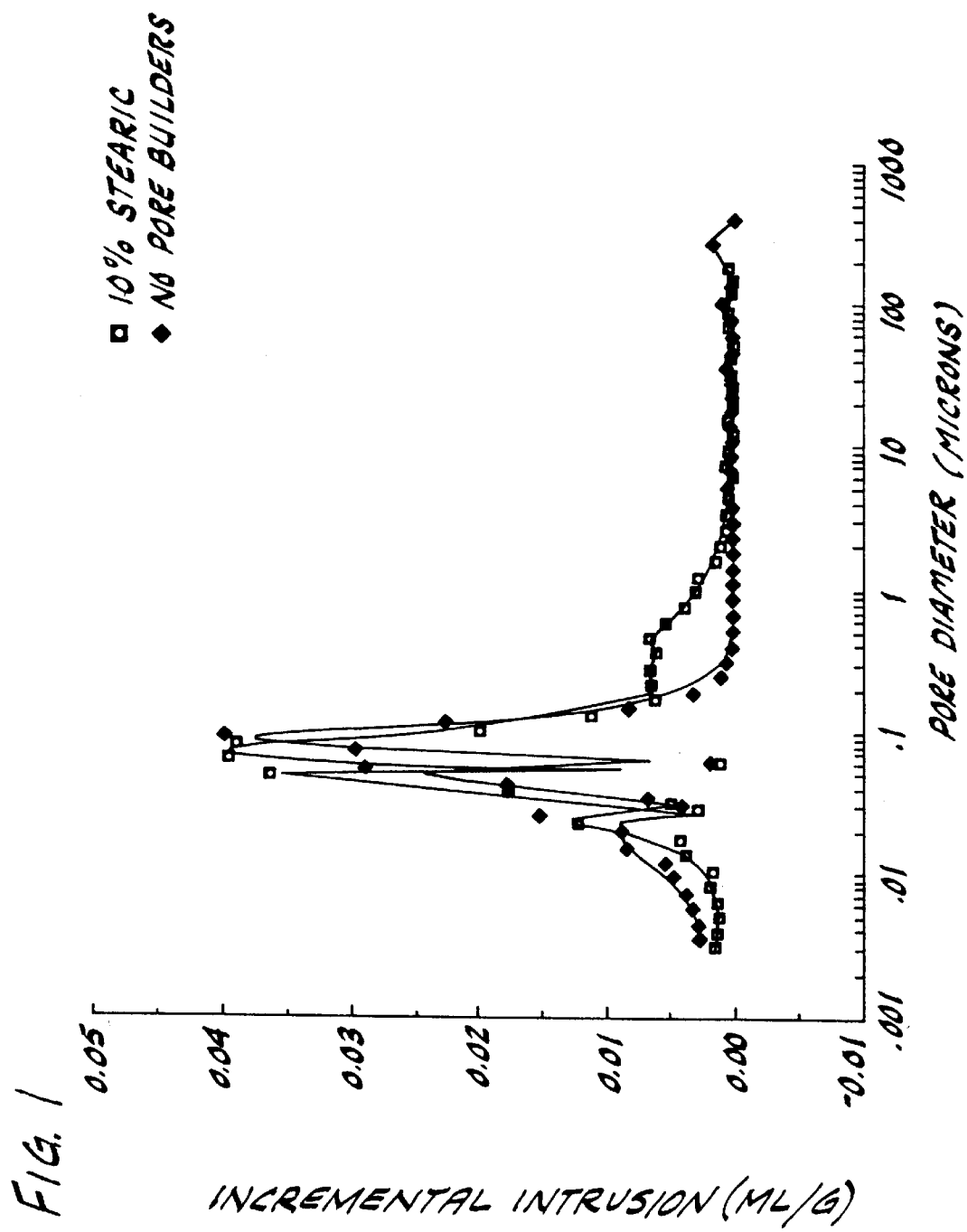
FIG. 1 is a plot comparing the distribution of pore volume as a function of pore diameter in two vanadium/phosphorus oxide catalysts prepared by ANST activation of a tableted catalyst precursor composition, one comprising a catalyst prepared from a precursor containing no pore modification agent, the other comprising a catalyst of the invention prepared from a precursor composition containing 10% by weight stearic acid in the pores thereof.

In accordance with the present invention, a novel molybdenum-modified vanadium phosphorus oxide (VPO) catalyst is provided which is effective in minimizing the acrylic acid content of the reaction product gas produced in the catalytic oxidation of a hydrocarbon to a dicarboxylic acid anhydride. In particular, it has been found that, by incorporating a relatively small and carefully controlled proportion of molybdenum into a VPO precursor and activating the modified precursor, a catalyst is provided which significantly reduces the acrylic acid content of the reaction product gas exiting a reactor in which maleic anhydride is produced by the vapor phase oxidation of a $C_4$ hydrocarbon such as butane.

The exact mode of action of the molybdenum is not completely understood. While not desiring to be bound by theory of the invention or to limit the invention in any way, it is believed that the molybdenum provides substantial surface area of active sites on the surface of the catalyst particles. As acrylic acid is formed, it is believed to be adsorbed on the active sites and subsequently decomposed to other by-products of the reaction. Such active site surface area allows the catalyst to minimize the proportion of acrylic acid exiting the reactor relative to the production rate of maleic anhydride. The catalyst does not require equilibration before acrylic acid formation is decreased.

It has also been discovered that molybdenum in the catalyst of the present invention is concentrated substantially on the surface of the catalyst particle. Such catalysts are formed, for example, by introducing a molybdenum-containing compound into the reaction mixture once a solid VPO precursor has formed. Prior art molybdenum-containing catalysts are generally prepared from a solution of vanadium and molybdenum salts prior to isolation of a solid VPO catalyst precursor, resulting in molybdenum dispersed throughout the catalyst particles.

As compared to conventional molybdenum-modified VPO catalysts, the catalyst of the present invention contains a relatively small amount of molybdenum. Molybdenum is present in a proportion of between about 0.0020 and about 0.0060 moles per mole of vanadium in the catalyst. Preferably, molybdenum is present in a proportion of between about 0.0030 and about 0.0060 moles per mole vanadium, and, more preferably, between about 0.0035 and about 0.0055 moles per mole vanadium. The molar ratio of molybdenum to vanadium is generally about 0.0020 to about 0.0060 in the catalyst precursor prior to activation, resulting in a concentration of molybdenum oxide well below one percent by weight of the catalyst, preferably about 0.20 to about 0.30 percent by weight. Although greater amounts of molybdenum may be used, acid anhydride yield may be diminished without further reduction in acrylic acid formation.

More generally, the proportion of molybdenum should be such as to enable the catalyst to have a developed surface area of at least about 15 $m^2/g$, and, preferably, at least about 20 $m^2/g$. The proportion of molybdenum should also be sufficient to enable the catalyst to exhibit a weight/area productivity of at least about 3.5 mg maleic anhydride/$m^2$-hr and/or a weight/weight productivity of at least about 100 g maleic anhydride/kg.cat.-hr. when contacted with a gas containing 2.4% by volume n-butane in air, at a gas flow volume to catalyst weight ratio of 2180 cc/g-min. under a pressure of $1.055 \times 10^2$-kPa-G, and at a temperature sufficient to maintain a hydrocarbon conversion of 85 mole percent.

The catalysts of the present invention preferably do not include promoter elements. However, minor amounts of promoter elements can be incorporated in the catalysts so long as the promoter elements do not counteract the ability of the catalyst to minimize acrylic acid formation. For the most advantageous performance properties, it is preferred that the ratio of the sum of the molar proportions of molybdenum and all promoter elements to the proportion of vanadium in the catalyst does not exceed about 0.04. Those skilled in the art will understand what other elements may be considered promoter elements for VPO catalysts. Most of the metallic and semiconductor elements have some effect, or have been proposed, as promoters for VPO catalysts used for the oxidation of $C_4$ hydrocarbons to maleic anhydride. These include, for example, Li, Na, Mg, Al, Ti, Cr, Mn, Fe, Co, Cu, Ca, Y, Nb, Ru, Ag, Sn, Ba, La, the rare earth metals, Hf, Ta, W, Re, Th, Bi, Sb, Ge, Zr, U, Ce, Ni, Zn and Si. Processes for incorporating promoters in VPO catalysts are described in U.S. Pat. No. 5,364,824 which is herein incorporated by reference.

Shaped bodies having pressure drop characteristics acceptable for commercial fixed bed reactors typically have a principal dimension of at least about ⅛", more typically 5/32" to ½". Generally, therefore, the catalyst has a volume per body of at least about 0.02 cc, more commonly at least about 0.03 cc, and most preferably at least about 0.05 cc. Suitable body shapes for use in a fixed bed reactor are further described in U.S. Pat. No. 5,168,090. Catalysts of the present invention may also be used in commercial fluid bed reactors.

Figure 11:
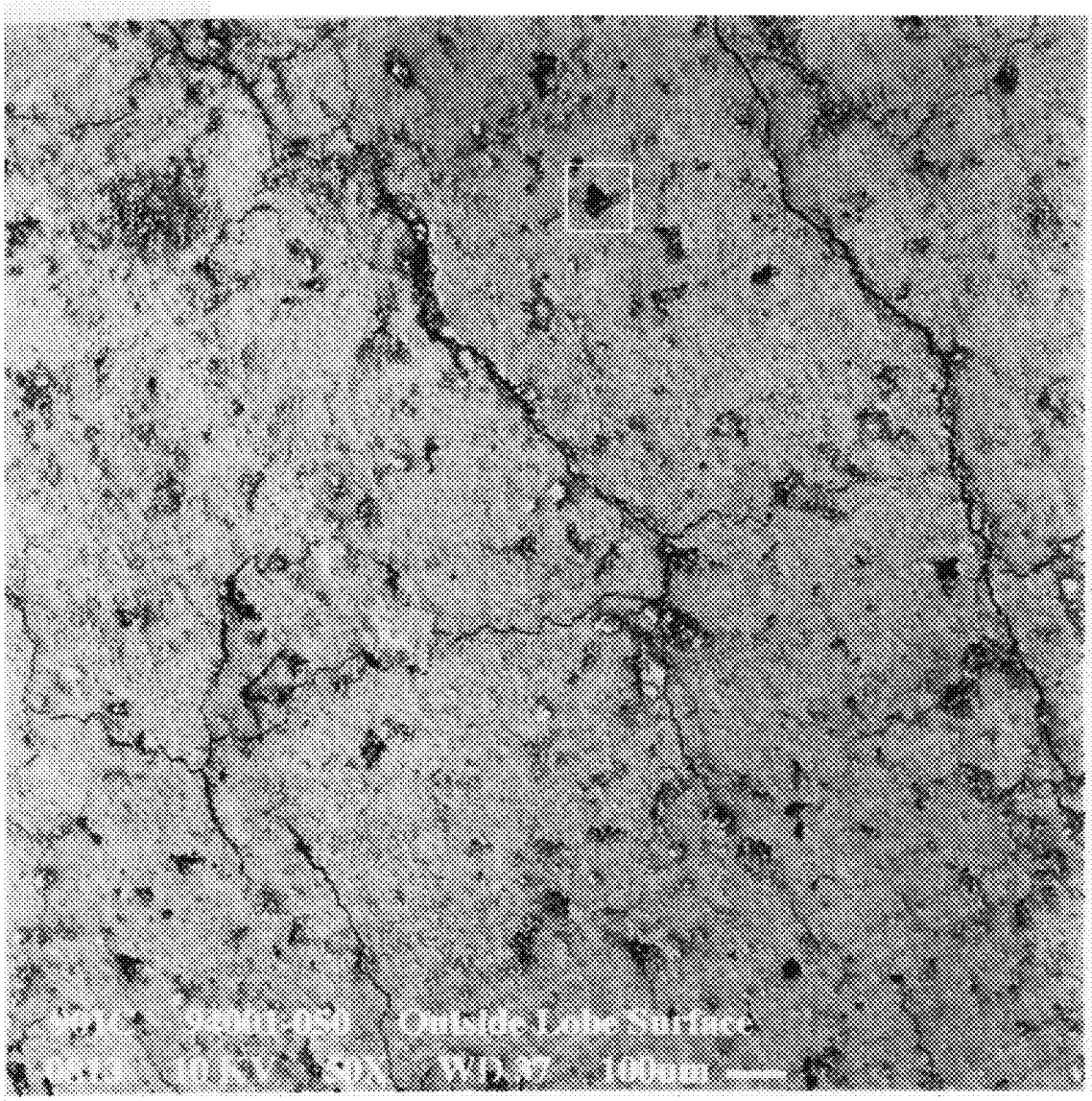
Figure 12:
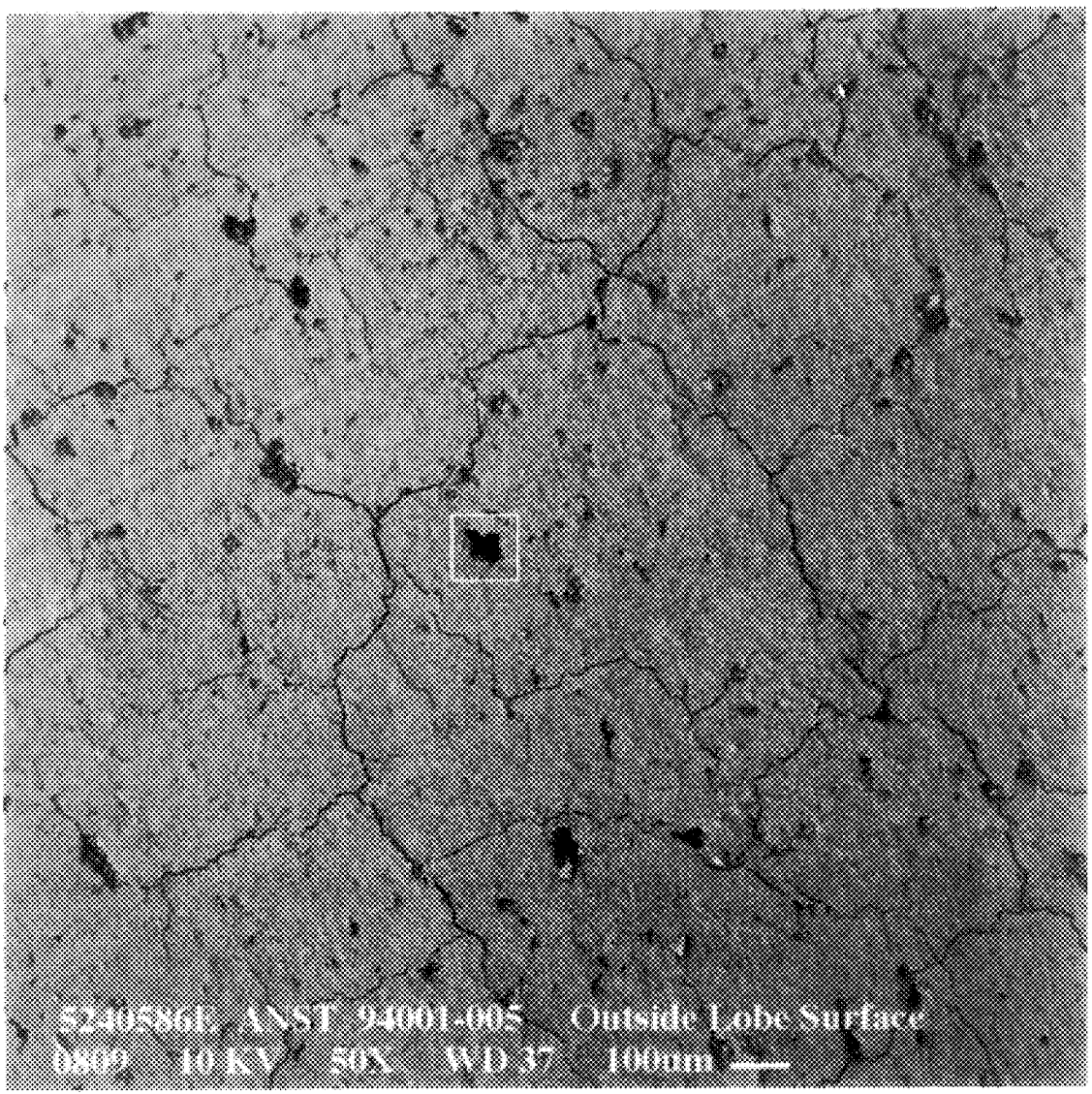

The molybdenum-modified catalysts of the invention are useful for the partial oxidation of hydrocarbons having at least four carbon atoms in a straight chain with molecular oxygen or a molecular-oxygen containing gas in the vapor phase to a dicarboxylic acid anhydride. The catalysts are used in producing dicarboxylic acid anhydrides wherein acrylic acid is produced as a by-product of the oxidation reaction. Preferably, the catalysts are used for the partial oxidation of nonaromatic hydrocarbons having at least four carbon atoms in a straight chain with molecular oxygen or a molecular-oxygen containing gas in the vapor phase to maleic anhydride. These catalysts are preferably prepared by the general procedures given in U.S. Pat. Nos. 4,562,268, 4,560,674, and 4,567,158 which are herein incorporated by reference. The catalysts prepared by these procedures exhibit a highly uniform macrostructure that predominantly comprises generally spheroidal particles of radially oriented three-dimensional networks of randomly shaped open cells. In the processes otherwise fully described in these patents, molybdenum and any promoter elements are added at times during the catalyst precursor preparation that preserve the open cell morphology but insure maximum benefit to catalyst performance from the presence of molybdenum and any promoter elements. It should be understood, however, that the advantageous effect of the proper amount of molybdenum is not limited to catalysts of open cell morphology, but is also realized in catalysts of a variety of different forms. See, for example, the various surface textural characteristics illustrated in the figures of U.S. Pat. No. 4,562,268, the macrostructures of which include: striated spherical particles composed of a succession of layers stacked one upon another (FIGS. 7–10 of '268); and clusters of small groups of associated platelets (FIGS. 11 and 12 of '268).

For purposes of this invention, the term "yield" means the ratio of the moles of maleic anhydride obtained to the moles of hydrocarbon feedstock introduced into the reactor multiplied by 100. The term "selectivity" means the ratio of the moles of maleic anhydride obtained to the moles of hydrocarbon feedstock reacted or converted multiplied by 100 with the terms expressed as mole percent. The term "conversion" means the ratio of the moles of hydrocarbon feedstock reacted to the moles of hydrocarbon feedstock introduced into the reactor multiplied by 100 with the term expressed as mole percent. The term "weight/weight productivity" means the weight of maleic anhydride produced per unit weight of catalyst per hour. The term "weight/area productivity" means the weight of maleic anhydride produced per unit B.E.T. developed surface area of catalyst per hour. The term "space velocity" or "gas hourly space velocity" or "GHSV" means the volumetric flow rate of gaseous feed expressed in standard (273K and 14.7 psig) cubic centimeters per hour divided by the bulk catalyst volume expressed in cubic centimeters with the term expressed as cc/cc/hour or simply, $hr^{-1}$. The term "gas flow 50548643.001 volume to catalyst weight ratio" means the ratio of the volumetric flow rate of a gas containing a hydrocarbon and air or oxygen to the weight of a catalyst bed through which the gas is flowing, expressed in g/cc-min.

VPO catalysts are prepared by reaction of a vanadium compound and a phosphorus compound to produce a precursor, and activation of the precursor by calcination to convert a substantial fraction of the precursor composition to vanadyl pyrophosphate. For fixed bed catalysts, the precursor is formed into a body of the desired shape before heat treatment to transform the precursor composition to active catalyst. In the synthesis of molybdenum-modified VPO catalysts, the character of the catalyst obtained is affected by the compatibility of the chemistry of the molybdenum-containing compound with the precursor chemistry, the influence of molybdenum on the transformation of the precursor to the active phase, and the effect of the molybdenum concentration on the development of the active phase and of the specific surface area of the catalyst upon equilibration.

The most preferred routes to VPO catalysts are by way of the precursor compound $VOHPO_4 \cdot 0.5H_2O$. There are numerous established synthetic options for the preparation of this precursor, and the procedures yield widely varying macrostructures. Generally the aforesaid precursor can accommodate nonstoichiometry, i.e., a P/V ratio of about 0.95 to about 1.3, intercalated organic material, such as the alcohol of the reaction medium, molybdenum, and promoter elements, with minor structural modifications.

The vanadium compounds useful as a source of vanadium in the catalysts of the instant invention in general are those containing pentavalent vanadium and include vanadium pentoxide or vanadium salts, such as ammonium metavanadate, vanadium oxytrihalides, and vanadium alkylcarboxylates. Among these compounds, vanadium pentoxide is preferred.

The phosphorus compounds useful as a source of phosphorus in the catalyst employed in the instant invention are preferably those that contain pentavalent phosphorus. Suitable phosphorus compounds include phosphoric acid, phosphorus pentoxide, or phosphorus perhalides such as phosphorus pentachloride. Of these phosphorus-containing compounds, phosphoric acid and phosphorus pentoxide are preferred.

The catalysts of the instant invention are normally prepared by introducing a substantially pentavalent vanadium-containing compound and a pentavalent phosphorus-containing compound into an alcohol medium capable of reducing in part the vanadium to a valence state of less than +5. Preferably, the mixture of the vanadium-containing compound, phosphorus-containing compound and alcohol medium forms a slurry.

The resultant mixture is contacted with an effective amount of an alcohol-modifying agent capable of changing the state of the alcohol to a state conducive to the formation of the catalyst precursor. The exact function and mode of action of the alcohol-modifying agent is not completely understood. While not desiring to be bound by theory of the invention or to limit the invention in any way, it is believed that the alcohol-modifying agent alters the surface tension of the alcohol to enhance intimate contact among the phosphorus-containing compound, the vanadium-containing compound, and the alcohol, and thereby promotes the formation of the highly porous catalyst precursor having the open cell morphology which is convertible by a controlled sequence of gas and thermal treatments into the catalyst of the instant invention. Suitable, but non-limiting, alcohol-modifying agents include hydrogen iodide, sulfur dioxide, fuming sulfuric acid, surfactants as described in U.S. Pat. No. 4,149,992, which specification is herein incorporated by reference, formic acid, oxalic acid, and citric acid. Of these alcohol-modifying agents, oxalic acid is preferred.

The amount of alcohol-modifying agent employed is not narrowly critical. All that is necessary, as previously noted, is that the amount employed be sufficient to modify the alcohol to a state that is conducive for the formation of the catalyst precursor. An amount sufficient to provide an alcohol-modifying agent/vanadium-containing compound mole ratio of 0.64 is normally employed. Larger or smaller amounts may, however, be employed, if desired, for example in the range of between about 0.4 and about 1 moles per mole of vanadium.

The phosphorus-containing compound may be introduced into the vanadium/alcohol/alcohol-modifying agent mixture in any convenient manner. It may be added in the form of a solution or suspension in the alcohol medium or component of the mixture, or when the phosphorus-containing compound is in liquid form, such as >100% phosphoric acid, it may be added alone. Alternatively, a vanadium-containing compound and a phosphorus-containing compound, such as >100% phosphoric acid may be introduced simultaneously into the alcohol medium. In yet another mode, the vanadium-containing compound is introduced into a solvent or dispersion of the phosphorus-containing compound in the alcohol. It is preferred, however, to introduce the phosphorus-containing compound to a mixture of the alcohol-modifying agent, the vanadium-containing compound, and the alcohol.

The alcohols employed in the preparation of the catalysts of the instant invention are preferably anhydrous and must be capable of reducing at least a portion of the vanadium to a +4 valence state, either upon addition of the vanadium-containing compound or upon mixing and heating. In addition the alcohol should be a solvent for the phosphorus-containing compound especially the preferred phosphoric acid, and relatively unreactive toward the phosphorus-containing compound. Preferably, the alcohol is not a solvent for the catalyst precursor mixed oxides of phosphorus and vanadium. In those instances wherein the catalyst precursor is soluble in the alcohol medium, precipitation should be easily induced by removal of a portion of the alcohol. Suitable alcohols include primary and secondary alcohols, such as methanol, ethanol, 1-propanol, 2-propanol, 1-butanol, 2-methyl-1-propanol (isobutyl alcohol), 2-butanol, 3-methyl-2-butanol, 2,2-dimethyl-1-propanol, 4-methyl-2-pentanol, and 1,2-ethanediol (ethylene glycol). Of these alcohols, isobutyl alcohol (IBA) is preferred.

After the phosphorus and vanadium compounds are introduced into the alcohol medium to form the alcohol/alcohol-modifying agent/vanadium-containing compound/phosphorus-containing compound mixture, reduction of at least a portion of the vanadium to a valence state of +4 is effected, preferably by heating the mixture, with stirring, if desired, until a blue solution or slurry is obtained. In general, heating the mixture at reflux temperature for a period of time ranging from about four hours to 20 hours is sufficient.

The molybdenum modifier may be added as a solid, a suspension of solids, or a solution to the product of the reaction of the vanadium and phosphorus-containing compounds to form a solid molybdenum-modified catalyst precursor composition. For purposes of the invention, a "molybdenum modifier" is a molybdenum-containing compound which alters the hydrocarbon/oxygen reaction which produces a dicarboxylic acid anhydride by minimizing the acrylic acid content of the reaction product gas produced in the catalytic oxidation of a hydrocarbon to the dicarboxylic acid anhydride. Molybdenum-containing compounds that may serve as modifiers of the invention include molybdenum oxides, halides, carboxylates, carbides, nitrides, and oxyhalides. Of these compounds, carboxylates and oxides are preferred. Suitable carboxylates for molybdenum salts include 2-ethylhexanoate, formate, acetate, propionate, butyrate, isobutyrate, pentanoate, hexanoate, heptanoate, octanoate, nonanoate, decanoate, oxalate, naphthenate, and benzoate. Of these carboxylates, molybdenum 2-ethylhexanoate is preferred. Molybdenum oxides including, for example, molybdenum trioxide, molybdenum dioxide, molybdenum dioxydichloride, molybdenum oxytetrachloride, and molybdenum oxytrichloride, are also acceptable molybdenum-containing compounds for purposes of the invention. Additional suitable molybdenum modifiers include molybdenum trichloride, molybdenum tetrachloride, molybdenum trichloride dibenzoate, molybdenum (III) acetylacetonate, molybdenum tetrachloride dipyridine, molybdenyl bis-acetylacetonate, 12-molybdophosphoric acid, 12-molybdosilicic acid and ammonium molybdate.

Molybdenum 2-ethylhexanoate or other soluble molybdenum sources can be added to the reaction product in solutions of alcohols, esters, aromatics, and alkanes. Of these solvents, isobutyl alcohol, isobutyl isobutyrate, decane, mineral spirits and other solvents in which the molybdenum-containing compound is substantially soluble constitute preferred but not limiting solvents of choice. Typically, the molybdenum 2-ethylhexanoate or other soluble molybdenum source is dissolved in a suitable solvent in an amount of 20 percent by weight or less.

The molybdenum-containing compound may be added to the reaction mixture before, during, or after formation of the product of the reaction. Preferably, molybdenum is incorporated into the product of the reaction, forming a solid molybdenum-modified precursor composition. The molybdenum is typically added to the reaction mixture during the reflux period at reaction mixture temperatures ranging from ambient to the reflux temperature of the reaction mixture, preferably at a temperature of less than 50° C. Because the molybdenum is reactive with the phosphorus compound, it is preferably withheld from the reaction system until the vanadium compound has been substantially consumed by reaction to form a solid VPO catalyst precursor comprising mixed oxides of vanadium and phosphorus. Otherwise, it may be necessary to increase the P/V ratio above the optimum for the purpose of driving the reaction of the vanadium compound to completion. A preferred method of preparation, therefore, is referred to as the "post" method, in which the vanadium compound is first reacted at elevated temperature with a modest excess of phosphorus compound, for example, at a P/V ratio of 1.05 to 1.20, until the vanadium compound is substantially exhausted; and thereafter the molybdenum-containing compound is reacted with the residual phosphorus compound to incorporate the molybdenum in the solid VPO catalyst precursor composition. The reaction between the vanadium and phosphorus compounds is carried out at a temperature in the range of between about 90 and about 120° C., conveniently at atmospheric reflux temperature. The reaction mixture is then cooled to below 50° C. for addition of the molybdenum source. Preferably, the solid VPO precursor composition precipitates from the alcohol medium as a finely divided precipitate that contains the molybdenum after its addition.

In a preferred catalyst preparation process, the vanadium compound and phosphorus compound are reacted at a temperature in the range of between about 90° C. and about 120° C., again using a P/V ratio of 1.05 to 1.15. The reaction mixture is cooled below 50° C. for addition of the molybdenum source, and optionally a further increment of phosphoric acid; and then the reaction system is again heated to a temperature in the range of between about 90° C. and about 120° C. for incorporation of the molybdenum into the precursor structure. After the second reflux period, the volume of alcohol in the reaction mixture may optionally be reduced by stripping about 15% to about 35% of the alcohol. Because both the V-P reaction and the incorporation of molybdenum are advantageously conducted at or near atmospheric reflux temperature, this preferred method is referred to hereinafter as the "reflux-cool-reflux" or "RCR" method. The molybdenum-containing compound used in the RCR method is preferably a molybdenum oxide powder of small particle size.

In another preferred method of the invention, a pentavalent phosphorus-containing compound, a substantially pentavalent vanadium-containing compound and alcohol are mixed and heated to reflux. The vanadium compound and phosphorus compound are reacted in the alcohol medium, preferably at a reflux temperature in the range of between about 90° C. and about 120° C. and a P/V ratio of 1.05 to 1.15, for 4 to 20 hours to form a solid VPO catalyst precursor. The volume of alcohol in the reaction mixture may optionally be reduced by stripping about 15% to about 35% of the alcohol charged. If the reaction mixture is at or above its boiling temperature, the mixture is then cooled, preferably to less than about 50° C. The reaction mixture is then allowed to settle for a period of about 2 to about 12 hours, preferably for about six hours until sedimentation of the solid VPO precursor is complete. A portion of the alcohol and the remaining unreacted phosphorus is then removed, for example, by decantation or by filtration with subsequent addition of a small amount of the alcohol to the settled or reslurried solid VPO precursor, in order to reduce the P/V ratio to about 1.045 to about 1.135, preferably about 1.075. A molybdenum salt is also added to the solid VPO precursor in the alcohol medium and the slurry is heated, preferably to a reflux temperature in the range of between about 90° C. and about 120° C., for 1 to 3 hours to form a solid molybdenum-modified catalyst precursor. This method is referred to hereinafter as the "post decant" method because the molybdenum is incorporated in the catalyst precursor after removal of alcohol and excess phosphorus. This method prevents molybdenum from being removed in the solvent, thereby positively controlling the amount of molybdenum available for incorporation in the catalyst precursor and eliminating the environmental hazard of disposal of molybdenum-containing solvent. The method also provides higher maleic anhydride yield, a lower operating temperature, and surface-concentrated molybdenum on the catalyst particles as compared to conventional VPO catalysts. The molybdenum-containing compound used in the post decant method is preferably a carboxylate salt which is hydrocarbon soluble such as molybdenum 2-ethylhexanoate dissolved in isobutyl alcohol.

In another method of the invention, the solid molybdenum-modified catalyst precursor is formed by dry blending a phosphorus-vanadium oxide powder prepared as described above with a molybdenum-containing powder. This method is hereinafter referred to as the "dry blend" method because the VPO precursor and molybdenum source are mixed without the use of a solvent medium. The RCR and post decant methods are more preferred than the dry blend method because the molybdenum is more uniformly dispersed on the catalyst surface by such methods. Moreover, a greater molar ratio of molybdenum to vanadium is required in a dry blend preparation to provide comparable acrylic acid reduction. The molar ratio of molybdenum to vanadium in the dry blend preparation is between about 0.0020 and about 0.0120, preferably between about 0.0060 and about 0.0100, and, more preferably between about 0.0070 and about 0.0085. The molybdenum source used in the dry blend method is preferably a molybdenum oxide powder of small particle size.

The solid molybdenum-modified precursor composition formed by a wet preparation process is recovered after cooling to below 50° C. by conventional techniques well known to those skilled in the art, including filtration, centrifugation, and decantation.

The solid molybdenum-modified precursor composition of the instant invention contains vanadium in the average valence state of from about +3.2 to +4.0 or simply 3.2 to 4.0. This average valence state is achieved when essentially all of the pentavalent vanadium introduced into the reaction mixture is reduced to the +4 valence state or below. It is believed that as this reduction occurs, the reduced vanadium simultaneously reacts with the phosphorus present in the reaction mixture to form the solid molybdenum-modified catalyst precursor comprising mixed oxides of vanadium and phosphorus.

Preferably, the solid molybdenum-modified precursor composition also contains molybdenum in the +6 valence state after the precursor is activated. It is believed that the Mo oxidation state remains essentially constant throughout preparation of the catalyst and reduces with time onstream.

The recovered solid molybdenum-modified catalyst precursor is dried to remove free solvent at a temperature of from 150 to 275° C., preferably under vacuum, to remove a portion of the bound solvate that includes both water and alcohol. To avoid reaction of the alcohol with catalytically active vanadium sites, the drying is performed in an atmosphere of low or no oxygen content such as dry nitrogen. The precursor may be dried at a relatively modest temperature of, for example, 110° C. to 150° C., and then subjected to "post dry" treatment (roasting) at a temperature in the range of 200° C. to 275° C. Advantageously, the post dry treatment is carried out by treating the precursor powder in an inert gas in the post dry temperature range. After the bed reaches the desired temperature, it is held at that temperature for a suitable period, for example 30 minutes to two hours, and thereafter an air/steam mixture is introduced, preferably on an incremental schedule to a maximum of 10–30% oxygen, after which the bed is cooled in an inert atmosphere to room temperature. The dried solid molybdenum-modified precursor powder is then formed into any desired structure for reactor use with the aid of a die lubricant such as graphite. Typically, about 1 to about 5 percent by weight graphite is mixed with the dried promoted catalyst powder. The resultant catalyst bodies (structures) are subjected to heat treatment as described below for transformation to active catalyst.

The heat treatment allows the B.E.T. developed surface area of a shaped body vanadium phosphorus oxide catalyst, or the average developed B.E.T. surface area of a fixed bed of such shaped catalyst bodies, to be greater than 15 $m^2/g$, and, preferably, greater than 20 $m^2/g$. Developed surface areas of this magnitude are achieved by contacting the shaped bodies comprising the promoted VPO catalyst with a stream of reactant gases comprising oxygen and a non-aromatic hydrocarbon having at least four carbon atoms in a straight chain, and reacting the hydrocarbon and oxygen in the presence of the catalyst body, for an appropriate period of time, typically about 150 to about 400 hours. These surface areas are measured using Micromeritics FlowSorb II 2300 instrument according to the single point BET method with nitrogen [from Brunauer et al., *Journal of the American Chemical Society*, 60, 309–319 (1939)].

The point at which the developed surface area of the catalyst reaches a maximum after exposure to the oxygen/hydrocarbon reaction may be considered an equilibrium point, and the process of bringing the developed surface area to its maximum by exposure to this reaction is referred to as "equilibration" of the catalyst. The exposure effective for equilibration is essentially the same as that used for "conditioning" a VPO catalyst in accordance with established practice. It has been discovered that, upon equilibration, the shaped body catalysts of the invention consistently exhibit a developed surface area of at least 15 $m^2/g$.

The dried solid molybdenum-modified precursor compound is generally defined as $$VO(Mo)_m HPO_4 \cdot aH_2O \cdot b(P_{2/c}O) \cdot n \text{ (organics)}$$

wherein m is a number from about 0.0020 to about 0.0060, b is a number taken to provide a P/V atom ratio of from about 0.95 to about 1.3, and c is a number representing the oxidation number of phosphorus and has a value of 5.

Activation of the dried formed molybdenum-modified precursor is performed in a controlled manner using a sequence of gas and thermal treatments as fully described in U.S. Pat. No. 5,137,860. The activated catalyst corresponds to the formula:

$$(VO)_2(Mo)_m P_2 O_7 \cdot b(P_{2/c}O)$$

where M, m, b and c are as defined above. The overriding principle to follow in these treatments is to avoid treatments in which exotherms occurring on the catalyst surface as a result of either alcohol oxidation or phosphate condensation (i.e., catalyst phase changes) exceed by 30 to 50° C. or more the set point temperature of the furnace. Accordingly, a sequence of temperature holds are introduced at times when the catalyst shows exothermic behavior. Typically, the dried formed molybdenum-modified catalyst precursor is heated to 260° C. at 4° C./min. from ambient temperature in flowing air. After a one hour hold at 260° C., steam is added such that the air/steam ratio is between 0.50 and 1.50, preferably at 1.00. The ratio of the total flow of gas (air and steam) to the total weight of catalyst treated is generally between 10 and 20 L/min.-lbs., where the total gas flow is given in standard liters per minute and the weight of catalyst is in lbs. The catalyst is then heated in the air/steam flow while the temperature is increased at an average of 4° C./min. up to 425° C. The dried formed molybdenum-modified precursor is heated at 425° C. for one hour, after which time the air is replaced with nitrogen and the catalyst is heated for another 6 hrs. in a nitrogen/steam flow at 425° C. The catalyst is then cooled to room temperature in a dry atmosphere.

More generally, the activation process may be described as follows. In operation of the process of the instant invention, the dried formed molybdenum-modified catalyst precursor is transformed into the active catalyst by a series of steps conveniently referred to as calcination. This transformation, which is critical for the preparation of superior catalysts, is accomplished in three stages. For convenience, these may be referred to as (1) initial heat-up stage; (2) rapid heat-up stage, and (3) maintenance/finishing stage.

In the initial heat-up stage, the dried formed molybdenum-modified catalyst precursor is heated in an atmosphere selected from the group consisting of air, steam, inert gas, and mixtures thereof, at any convenient heat-up rate, to a temperature not to exceed the phase transformation initiation temperature, which temperature is about 300° C. In general, suitable temperatures for the initial heat-up stage range from about 200° C. to about 300° C., with a temperature of from about 250° C. to about 275° C. being preferred.

After the desired temperature has been achieved in the initial heat-up stage, the initially selected atmosphere (in the event it does not contain molecular oxygen and steam and/or has a different composition than that which is desired for the rapid heat-up stage) is replaced by a molecular oxygen/steam-containing atmosphere, while maintaining the dried formed molybdenum-modified catalyst precursor at the temperature achieved in the initial heat-up stage. Such atmosphere optionally may contain an inert gas and, as such, may be conveniently represented by the formula $$(O_2)_x (H_2O)_y (IG)_z$$

wherein IG is an inert gas and x, y, and z represent mol % (or volume %) of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere. A critical feature of the instant invention is that such atmosphere must contain at least a portion of molecular oxygen and water (as steam). The presence of the inert gas in such atmosphere, as indicated by the formula, is optional. Nonlimiting examples of inert gases suitable for use in the molecular oxygen/steam-containing atmosphere include (molecular) nitrogen, helium, argon, and the like, with nitrogen generally being preferred for practical reasons.

Once the molecular oxygen/steam-containing atmosphere is provided, the dried formed molybdenum-modified catalyst precursor is subjected to the rapid heat-up stage of the calcination. In the rapid heat-up stage, the initial heat-up stage temperature is increased at a programmed rate of from about 2° C. per minute (° C./min) to about 12° C./min, preferably from about 4° C./min to about 8° C./min, to a value effective to eliminate or remove the water of hydration from the catalyst precursor. In general, a temperature of from about 340° C. to about 450° C., usually at least about 350° C. and preferably from about 375° C. to about 425° C. is suitable.

Following the rapid heat-up stage, the dried formed molybdenum-modified catalyst precursor is subjected to the maintenance/finishing stage of calcination. In the maintenance/finishing stage, while the molecular oxygen/steam-containing atmosphere, is maintained, the temperature is adjusted to a value greater than 350° C., but less than 550° C., preferably from about 375° C. to about 450° C., most preferably from about 400° C. to about 425° C. The adjusted temperature is then maintained, first in the molecular oxygen/steam-containing atmosphere for a time effective to provide a vanadium oxidation state of from about +4.0 to about +4.5 or simply from about 4.0 to about 4.5, and thereafter in a nonoxidizing, steam-containing atmosphere for a time effective to complete the dried formed molybdenum-modified catalyst precursor-to-active catalyst transformation to yield the active catalyst. In a manner similar to the molecular oxygen/steam-containing atmosphere, the nonoxidizing, steam-containing atmosphere also optionally may contain an inert gas, with nitrogen generally being the preferred inert gas for practicable reasons.

The nonoxidizing, steam-containing atmosphere need not necessarily be completely free of molecular oxygen. However, such atmosphere preferably is substantially free of molecular oxygen. Accordingly, molecular oxygen may be present in an amount which is not effective to cause further oxidation of the vanadium beyond the desired oxidation state of about +4.0 to about +4.5, more particularly, not beyond the maximum desired oxidation state of about +4.5. In general, molecular oxygen may be present in amounts which do not exceed about 0.5 mol % of the nonoxidizing, steam-containing atmosphere.

The adjusted temperature is maintained in the molecular oxygen/steam-containing atmosphere for a period of time of from about 0.5 hour to about 3 hours, with a period of time of from about 1.5 hours to about 2.5 hours being preferred.

A suitable period of time during which the adjusted temperature is maintained in the nonoxidizing, steam-containing atmosphere is at least 1 hour, although longer periods of time up to 24 hours, or longer, may be employed, if desired, with a period of time of from about 3 hours to about 10 hours being preferred, and a period of about 6 hours being most preferred.

After activation by the process described above, the catalyst is brought to full activity by contacting it with a stream of reactant gases comprising oxygen (typically air) and a n-butane or another suitable hydrocarbon gas, and reacting the hydrocarbon with oxygen in the presence of the catalyst for a period sufficient to equilibrate the catalyst. The equilibration process takes place at a temperature of at least 350° C., typically 385–450° C. It is important that the stream contacting the catalyst contain at least about 0.6 mole % n-butane during equilibration, preferably at least about 1.5 mole % n-butane, and, more preferably between about 1.5 and about 2.0 mole % n-butane. Generally, equilibration requires several hundred hours, most typically 150 to 400 hours exposure to the reaction. The developed B.E.T. surface area of the catalyst typically increases upon equilibration. Where the catalyst is activated by the method described hereinabove, and the preferred molybdenum to vanadium ratios prevail, the catalyst exhibits a developed surface area of at least about 20 $m^2/g$.

After activation and equilibration, the dried formed molybdenum-modified precursor is transformed to a catalyst comprising a substantial proportion of vanadyl pyrophosphate, a compound having the empirical formula $(VO)_2P_2O_7$. The presence of this compound may be identified by its characteristic X-ray diffraction pattern. Examples of diffraction patterns for various vanadyl pyrophosphate preparations are shown in FIG. 22B of Centi, Trifiro, Ebner and Franchetti, "Mechanistic Aspects of Maleic Anhydride Synthesis from $C_4$ Hydrocarbons over Phosphorus Vanadium Oxides," *Chemical Reviews*, 88, 55–80 (1988). Differences in the ratio of the height of the diffraction peak at d-spacing 3.86 Å ($2\theta$ value of 23.0°) to the height of the diffraction peak at d-spacing 3.14 Å ($2\theta$ value of 28.4°) are indicative of structural order differences in the various vanadyl pyrophosphate preparations. The selective oxidation of hydrocarbons with vanadium phosphorus oxide systems is described as a structure sensitive reaction, and thus sensibly depends upon the structure of the vanadyl pyrophosphate. In equilibrated shaped body catalysts having a volume >0.02 cc and containing molybdenum effective to minimize acrylic acid formation while maintaining yield in the oxidation of $C_4$ hydrocarbons to maleic anhydride, it has been found that the most effective results are realized where the ratio of the height of the diffraction peak at d-spacing 3.86 Å ($2\theta$ value of 23.0°) to the height of the diffraction peak at d-spacing 3.14 Å ($2\theta$ value of 28.4°) is in the range of between about 0.8 to about 1.3, preferably <1.25.

The catalyst employed in the instant invention exhibits a phosphorus/vanadium atom ratio from about 0.95 to 1.30, a ratio of about 1.0 to about 1.2 being preferred, a ratio of between about 1.05 and about 1.15 being more preferred, and a ratio of about 1.055 and about 1.135 being most preferred. In general, the phosphorus/vanadium atom ratio in the catalyst is determined by the phosphorus/vanadium atom ratio in the starting catalyst that is charged to the reactor.

The molybdenum-modified catalysts prepared in the instant invention are useful in a variety of reactors to convert non-aromatic hydrocarbons to maleic anhydride. The catalysts are also useful in minimizing acrylic acid formation when other dicarboxylic acid anhydrides are formed by oxidation of a hydrocarbon. The catalysts may be used in a fixed-bed reactor in the form of tablets, pellets, or the like, or in a fluid-bed reactor using catalysts preferably having a particle size of less than about 300 microns. Detail of the operation of such reactors are well known by those skilled in the art.

The catalysts of the instant invention particularly are useful in fixed-bed (tubular), heat exchanger-type reactors. The tubes of such reactors can vary in diameter from about 0.635 cm (0.25 inch) to about 3.81 cm (1.5 inches) and the length can vary from about 15.24 cm (6 inches) to about 609.6 cm (20 feet) or more. It is desirable to have the surfaces of the reactors at relatively constant temperatures, and some medium to conduct heat from the reactors is necessary to aid in temperature control. Non-limiting examples of such media include Woods metal, molten sulfur, mercury, molten lead, and eutectic salt baths. A metal block reactor whereby the metal surrounding the tube acts as a temperature regulating body can also be used. The reactor or reactors can be constructed from iron, stainless steel, carbon steel, glass, and the like.

It has been discovered that the molybdenum-modified catalysts of the invention minimize the acrylic acid content of the reaction product gas produced in the catalytic oxidation of a hydrocarbon to maleic anhydride, particularly when the molybdenum-modified catalysts are loaded in the last zone of a catalyst pack. Acrylic acid content has been minimized by at least about 20%, preferably by about 20 to about 70%, while maintaining maleic anhydride yield of not less than about 50 mole % using the molybdenum-modified catalyst of the present invention in substantially the exit region of a catalyst pack extending over between about 25 and about 60 volume % of the catalyst pack. The molybdenum-modified catalyst is distributed substantially at the exit end of the catalyst bed, such that the butane conversion is at least about 40% in the region of the catalyst bed upstream of the exit region, preferably about 40 to about 60%. Preferably, the molybdenum-modified catalyst is charged substantially within between about 30 and about 55 volume % of the catalyst pack at the exit end of the reaction zone. More preferably, the molybdenum-modified catalyst is charged substantially within between about 35 and about 50 volume % of the catalyst pack at the exit end of the reaction zone. Use of the molybdenum-modified catalyst primarily at the exit end of the reaction zone limits the acrylic acid content of the reaction gas stream while preserving high maleic anhydride yield. It has been discovered that the zoned catalyst pack provides essentially the same acrylic acid content in the reaction product gas stream and greater maleic anhydride yield as compared to a catalyst pack charged solely with the molybdenum-modified catalyst of the invention.

The remainder of the catalyst, which is charged to the feed inlet end of the catalyst pack, can be any catalyst capable of catalyzing the vapor phase partial oxidation of a hydrocarbon to a dicarboxylic acid anhydride under oxidation conditions. Such catalysts include those as described in U.S. Pat. Nos. 5,275,996, 5,185,455, 5,168,090, 5,137,860, 4,855,459, 4,567,158, 4,562,268 and 4,560,674, which are incorporated herein by reference.

Suitable configurations for the catalyst pack are not narrowly critical and will vary depending upon a variety of factors such as overall catalyst pack length, production rate, composition of the active catalyst, and reaction conditions, and can be routinely determined by one skilled in the art. Nonlimiting examples include a configuration in which an unpromoted VPO catalyst as described in U.S. Pat. Nos. 5,275,996, 5,185,455, 5,168,090, 5,137,860, 4,567,158, 4,562,268 and 4,560,674 is nearest the feed inlet end and the molybdenum-modified catalyst of the present invention is nearest the exit end. Another suitable configuration has an unpromoted VPO catalyst as described in the above-identified U.S. patents nearest the feed inlet end, an unpromoted catalyst diluted with an inert solid as described in U.S. Pat. No. 4,855,459 adjacent the unpromoted catalyst at a region in the catalyst pack in which the highest temperature (the "hot spot") is located to reduce the heat generation at such location, and the molybdenum-modified catalyst of the present invention nearest the exit end. A preferred configuration of the present invention includes a relatively fine, high activity non-molybdenum-modified VPO catalyst nearest the feed inlet end, a coarse, low activity non-molybdenum-modified VPO catalyst adjacent the fine, high activity catalyst in the hot spot region, and the molybdenum-modified catalyst of the present invention nearest the exit end. Optionally, the fine, high activity catalyst can also be charged between the coarse, low activity catalyst zone and the molybdenum-modified catalyst zone.

The catalyst pack can include several zones of different catalyst compositions. Two to ten zones of catalyst may be used, but commercial practicality generally limits the practice of the invention to three to four zones of catalyst. The different types of catalyst may have different forms of the same chemical composition, or they may be chemically distinct types of catalyst. Preferably, the pack includes a non-molybdenum-modified VPO catalyst, which is either unpromoted or contains a promoter as described in U.S. Pat. No. 5,364,824, within an inlet region of the reactor zone extending over between about 40 and about 75 volume % of the catalyst pack and the molybdenum-modified catalyst of the invention within an exit region of the reactor zone extending over between about 25 and about 60 volume % of the catalyst pack. The unpromoted catalyst may be diluted in the direction downstream from the feed inlet as described in U.S. Pat. No. 4,855,459.

The catalysts within the exit region of the catalyst pack must be of a relatively fine particle size and must have a high surface area per unit bed volume in order to effectively adsorb and destroy acrylic acid in the exit portion of the catalyst bed. Gas flow through such a relatively fine catalyst region results in a relatively high pressure drop per unit length along the gas flow path. In order to avoid excessive overall pressure drop across the catalyst pack, it is especially desirable to minimize pressure drop in the region upstream of the molybdenum-modified catalyst zone. Pressure drop upstream of the modified catalyst can be minimized by using a coarse catalyst upstream. Use of a relatively coarse catalyst of low geometric surface area to geometric volume ratio (hereinafter simply "surface to volume ratio") upstream of the molybdenum-modified catalyst provides that the pressure drop per unit distance in the direction of gas flow in the critical region is materially lower than the pressure drop per unit distance in the bed as a whole. The "critical region" is a region within the bed where the combination of temperature and hydrocarbon concentration could otherwise cause the reaction to proceed at an excessive rate or the gas temperature to rise excessively. The critical region containing coarse catalyst bodies has high gas permeability, while the inlet and exit regions containing relatively fine catalyst bodies of higher surface to volume ratio have a lesser gas permeability. By capitalizing on the association of both high gas permeability and low unit activity with low surface to volume ratio, and using the low surface to volume ratio catalyst in a region where reaction rate is at all events high despite lesser promotion from the catalyst, this preferred embodiment of the invention provides high productivity with relatively low overall pressure drop through the system.

Additionally, use of such a stratified (graded) catalyst charge maintains high maleic anhydride yield while decreasing acrylic acid content of the reaction product gas stream.

Where the aspect ratio of the reactor tube is greater than 20 (L/D>20), the pressure drop of gas flowing through the tube may be accurately predicted from the relationship:

$$Wp = p_{in} - [p_m^2 - K_i T^{1.1} L^{2.76} (SV)^{1.76}]^{0.5}$$

where:

$Wp$=gas pressure drop through the catalyst bed (or region thereof)

$p_{in}$=reactor inlet pressure (to bed or region), psia $K_i$=a constant characteristic of the catalyst charge in region i of the bed (frictional constant)

T=reactor cooling fluid temperature, ° K.

L=length of the catalyst bed (or region thereof), ft.

SV=space velocity, $hr^{-1}$

Thus, where:

i=c=the critical region $K_c$=frictional constant for the critical region and where:

i=t=the total bed $K_t$=frictional constant for the bed as a whole,

Preferably, the relationship between $K_c$ and $K_t$ is such that the pressure drop per unit distance in the direction of gas flow in the critical region is at least about 15% lower, more preferably at least about 20% lower, most preferably at least about 30% lower than in the remainder of the bed.

Although pressure drop characteristic varies predictably with surface to volume ratio only for catalyst bodies of the same shape, data has been developed for a variety of catalyst sizes and shapes which provides a basis for selection of the catalyst bodies to be used in the critical region and other regions of the catalyst bed.

$K_i$ values were determined for various sizes and shapes of catalyst by charging the catalyst to a tube of the diameter of interest which has an aspect ratio of at least 100 and measuring the pressure drop at a variety of conditions and then fitting the data to the modified Ergun equation. The values of $K_i$ for use in the above equation were found to be as set forth below:

| Solid Shape | $K_i$ Value |
| --- | --- |
| Trilobe 6NC | $5.2 \times 10^{-10}$ |
| Trilobe III | $9.0 \times 10^{-10}$ |
| Trilobe V | $3.1 \times 10^{-10}$ |
| 3/16" cored tablets | $10 \times 10^{-10}$ |
| 7/32" cored tablets | $5.5 \times 10^{-10}$ |
| 1/4" cored tablets | $4.5 \times 10^{-10}$ |
| 6 mm inert spheres | $4.0 \times 10^{-10}$ |
| 8 mm inert spheres | $3.5 \times 10^{-10}$ |
| 1/8" solid tabs | $15 \times 10^{-10}$ |
| Tristars | $8.1 \times 10^{-10}$ |
| Tristars + 10% (vol) 6 mm inert | $8.0 \times 10^{-10}$ |
| Tristars + 20% (vol) 6 mm inert | $7.8 \times 10^{-10}$ |
| spheres 4–8 mm | $5.7 \times 10^{-10}$ |
| rings 8 × 8 × 4 mm | $31 \times 10^{-10}$ |

For purposes of comparison, the surface to volume ratios of a number of these catalysts were determined. These determinations were based on the ratio of the geometric surface area to the geometric volume enclosed by the surface, and do not include any effects of porosity. The ratios are as set forth below:

| Solid Shape | S/V cm$^{-1}$ |
| --- | --- |
| Trilobe 6NC | 23 |
| Trilobe III | 27 |
| Trilobe V | 20 |
| 3/16" cored tablets | 17 |
| 7/32" cored tablets | 14 |
| 1/4" cored tablets | 12 |
| 6 mm inert spheres | 10 |
| 8 mm inert spheres | 7.5 |
| 1/8" solid tabs | 17 |
| 3/16" solid tabs | 13 |
| spheres 4–8 mm | avg. ~10 |

These measurements demonstrate that, while surface to volume ratio is correlatable with pressure drop for catalyst bodies of a given shape, empirical determinations must be made to compare the pressure drop characteristics of catalyst bodies of different shapes. However, such determinations are readily made by routine experimentation. Accordingly, one skilled in the art can readily apply the principles described herein to establish an appropriate catalyst profile for high productivity and low pressure drop.

In the preferred catalyst pack configuration, the relatively fine, high activity non-molybdenum-modified VPO catalyst nearest the feed inlet end and the molybdenum-modified catalyst nearest the exit end have a surface to volume ratio of at least 20 cm$^{-1}$, preferably between about 23 cm$^{-1}$ and about 28 cm$^{-1}$. The coarse, low activity non-molybdenum-modified VPO catalyst located in the hot spot region has a $K_i$ value of not more than $6 \times 10^{-10}$, preferably between about $3 \times 10^{-10}$ and about $5 \times 10^{-10}$.

Prior to activation and equilibration of the catalyst as described above, the dried formed molybdenum-modified precursor can be treated to provide a porous catalyst in which resistance to internal diffusion in the catalyst bodies is minimized and productivity is enhanced at constant granule size and pressure drop. The porous nature of the catalyst contributes substantially to the active surface area at which the catalytic reaction takes place. However, for the internal surfaces of the catalyst body (tablets or pellets) to be utilized effectively, the feed gases, hydrocarbon and oxygen, must diffuse through the pores to reach the internal surfaces, and the reaction products must diffuse away from those surfaces and out of the catalyst body.

It has been discovered that enhanced productivity in the conversion of n-butane or other hydrocarbons to maleic anhydride is achieved by using a high surface area porous phosphorus/vanadium oxide catalyst which has been prepared using a pore builder to produce a high proportion of large pores therein. The catalysts comprise tablets, pellets or other shaped bodies having volume per shaped body of at least about 0.02 cc and a B.E.T. surface area of at least about 15 m$^2$/g. Such high surface area results from a high concentration of pores having an average pore diameter of less than about 0.05 microns. By the further presence of a high concentration of macropores having a pore diameter in the range of about 0.1 to about 3.3 microns, means are provided for rapid internal diffusion of product and reactant gases within the catalyst body. The large pores constitute flow arteries for distribution of these gases, thereby providing access of reaction gases to the active surfaces of the catalyst and egress of product gases from the finer pores of the catalyst body. This rapid exchange of gases allows maximum effective use of more of the internal surface of the tablet or pellet in the catalytic oxidation of $C_4$ hydrocarbons to maleic anhydride.

Total pore volume of the pore-built catalyst is at least about 0.15 cc/g, preferably at least about 0.18 cc/g. The catalyst possesses a uniquely advantageous combination of small pores, which present a substantial active surface for oxidation of a hydrocarbon to maleic anhydride, and larger pores, which provide access of reactants to, and egress of reaction products from, the smaller pores so that maximum effective use is made of the small pore surface area. Thus, at least about 40% of the pore volume is constituted of pores having a diameter less than about 0.1 $\mu$M, while at least about 20% of the pore volume is constituted of pores having a diameter of between about 0.1 and about 3.3 $\mu$M. In preferred embodiments of the invention, between about 40% and about 70% of the pore volume is constituted of pores having a diameter less than about 0.1 $\mu$m, between about 25% and about 60%, more preferably between about 30% and about 50%, of the pore volume is constituted of pores having a diameter between about 0.1 and about 3.3 microns, between about 10% and about 40%, more preferably between about 12% and about 30%, of the pore volume is constituted of pores having an average pore diameter between about 0.2 $\mu$M and about 2 $\mu$M, and between about 5% and about 20%, more preferably between about 7% and about 15%, of the pore volume is constituted of pores having an average pore diameter of between about 0.5 $\mu$M and about 1.2 $\mu$M.

FIG. 1 illustrates the distribution of pore volume as a function of pore diameter for the catalyst of the invention, as determined by a standard mercury porosimetry test for pore size distribution. For purposes of comparison, FIG. 1 also illustrates the pore size distribution for a catalyst prepared without use of a pore builder, but otherwise in a manner similar to that by which the catalyst of the invention was prepared. Because of the rapid internal diffusion afforded by the pore distribution within the catalyst of the invention, reactant gases can diffuse to the centers of even relatively large bodies for effective utilization of the entire internal surface thereof. This allows the catalyst to be produced in large tablets or pellets, resulting in low pressure drop through a catalyst bed without sacrificing productivity to the inaccessibility of internal surfaces. Tablets or other shaped bodies having pressure drop characteristics acceptable for commercial fixed bed reactors typically have a principal dimension of at least about 1/8", more typically 5/32" to 1/2". Generally, therefore, the catalyst of the invention has a volume per body (as defined by the outer contours thereof) of at least about 0.02 cc, more commonly at least about 0.03 cc, and most preferably at least about 0.05 cc. Further to minimize pressure drop in a catalytic reactor containing a fixed catalyst bed comprising the shaped bodies, the shaped body preferably comprises an opening therethrough for flow of reactant and product gases when the catalyst is used in the manufacture of maleic anhydride. Advantageously, the shaped body comprise a cylinder having a bore therethrough, as illustrated, for example, in U.S. Pat. No. 4,283,307.

A substantial volume of macropores is obtained by using a pore modification agent in the preparation of the catalyst tablets or pellets. By employing relatively mild conditions in generating the macropores, the desired pore size distribution is realized without adversely affecting the activity at the active internal surfaces of the catalyst. Such advantageous results are realized by both selection of the pore modification agent and control of the conditions under which the pore modification agent is removed from the catalyst.

Pore-built catalysts have been demonstrated to afford a productivity of at least about 4 lbs. maleic anhydride per hour-ft$^3$ of catalyst, in most instances at least about 4.8 lbs. maleic anhydride per hour-ft$^3$ of catalyst, with productivities of 6 lbs. maleic anhydride per hour-ft$^3$ of catalyst being readily achievable.

The pore-built catalysts also exhibit crush strengths satisfactory for use in commercial reactors, for example, for the production of maleic anhydride by catalytic oxidation of n-butane. Gravity and other compaction forces tend to crush porous catalyst bodies to a powder form, which results in high pressure drop through the catalyst bed. Inadequate crush strength is generally associated with low apparent density of the catalyst bodies. Despite their high total pore volume and large proportion of macropores, the activated catalyst bodies have been found to exhibit a substantial normalized apparent shaped body density, in the range of between about 1.0 and about 2.0 g/cc, and a crush strength of at least about 4 pounds, more typically at least about 6 pounds. Normalized apparent shaped body density is the same as measured apparent density where the solid phase of the catalyst is entirely constituted of phosphorus/vanadium oxide catalyst. Where the solid phase contains a foreign material such as, for example, a particulate iron aggregate, the normalized apparent density is determined by adjusting the measured apparent density for the weight fraction of VPO in the catalyst body. Thus, if:

$a_n$=the normalized apparent body density $a_m$=the measured apparent body density x=the weight fraction VPO in the catalyst body then:

$$a_n = a_m x$$

Where no aggregate is present, the normalized (and measured) apparent body density is between about 1.25 and about 2.0 g/cc.

In the pore-building process, a pore-modified catalyst precursor composition is prepared comprising a mixture of a particulate phosphorus/vanadium oxide catalyst precursor composition and a pore modification agent which is subject to removal from the catalyst after tableting or pelletizing. The pore modification agent should be subject to removal under mild conditions from the catalyst precursor body without undergoing an exothermic oxidation that adversely affects the VPO crystal structure or composition. More particularly, the pore modification agent should be removable without exposing the precursor composition to an exotherm of such severity as to cause either substantial reduction of the vanadium oxidation state or premature or uncontrollably rapid dehydration of the VPO precursor. To facilitate its removal under relatively mild conditions, the pore modification agent should be subject to vaporization, decomposition or oxidation at temperatures below 300° C. and without leaving a carbon, ash, or other residue so great as to create a substantial exotherm during the subsequent catalyst activation process. In particular, it is essential that the mechanism of removal of the pore modification agent be substantially quantitative without generating an exotherm during the removal process, whether due to decomposition or reaction with the atmosphere in which removal takes place, which would heat the catalyst precursor composition above 300° C. for more than about 20 minutes.

A preferred type of pore modification agent is thermally stable and has a substantial vapor pressure at a temperature below 300° C. It is particularly preferred that the pore modification agent have a vapor pressure of at least about 1 mm Hg at a temperature between about 150° C. and about 250° C., more preferably between about 150° C. and about 200° C.

Preferably, the pore builder has a relatively high melting point, e.g. greater than 60° C., so that it does not melt during compression of the catalyst precursor into a slug, tablet or pellet. It is also preferred that the pore builder comprise a relatively pure material rather than a mixture, so that lower melting components are not expressed as liquids under compression during formation of slugs or tablets. In the case of fatty acids, for example, it is known that lower melting components of fatty acid mixtures can be removed as liquids by pressing. If this phenomenon occurs during slug or tablet compression, the flow of liquid may disturb the pore structure and produce an undesirable distribution of pore volume as a function of pore diameter.

Particularly advantageous are pore modification agents which have a significant vapor pressure at temperatures below their melting points, so that they can be removed by sublimination into a carrier gas.

For example, the pore modification agent may be a fatty acid corresponding to the formula $CH_3(CH_2)_xCOOH$ where x>8 such as stearic acid (x=16), palmitic acid (x=14), lauric acid (x=10), myristic acid (x=12), esters of such acids and amides or other functionalized forms of such acids, for example, stearamide ($CH_3(CH_2)_{16}CONH_2$). Suitable esters may include methyl esters as well as glycerides such as stearin (glycerol tristearate). Mixtures of fatty acids can be used, but substantially pure acids, particularly stearic, generally perform better than mixtures. While fatty acids and fatty acid derivatives are generally preferred, other compositions which meet the functional requirements discussed above are also suitable for use as pore modification agents (pore builders).

Other preferred pore modification agents include polynuclear organic compounds such as naphthalene. Naphthalene melts at about 80° C. and has an appreciable vapor pressure at temperatures below 175° C. Moreover, because it lacks both functional groups and polarity, it is not strongly adsorbed, by either physisorption or chemisorption, to the catalyst precursor composition in the catalyst precursor body. Accordingly, quantitative removal of naphthalene is readily achieved under quite mild removal conditions.

A pore-modified catalyst precursor composition is prepared by mixing the pore builder in particulate form with a particulate precursor composition which contains oxides of vanadium and phosphorus. Preferably, the pore-modified precursor composition contains between about 6% and about 16%, preferably between about 8% and about 12%, by weight of pore builder. Preferably, a lubricity agent is also included in the mix, e.g., between about 2% and about 6% by weight graphite. This composition is then formed under compression into a tablet or other predetermined shape. Mixing is better and tablet integrity enhanced if the mean particle diameter of the precursor approximates the mean particle diameter of the precursor composition, at least within about two orders of magnitude. Typically, vanadium/phosphorus oxide precursor particles have a mean diameter in the range of between about 20 to 200 microns, most often in the range of between about 50 and 150 microns. It is generally preferred that the mean particle diameter of the pore builder be between about 10 and about 500 microns, more preferably between about 30 and about 90 microns, most preferably about 40 to about 50 $\mu$M.

Figure 7:
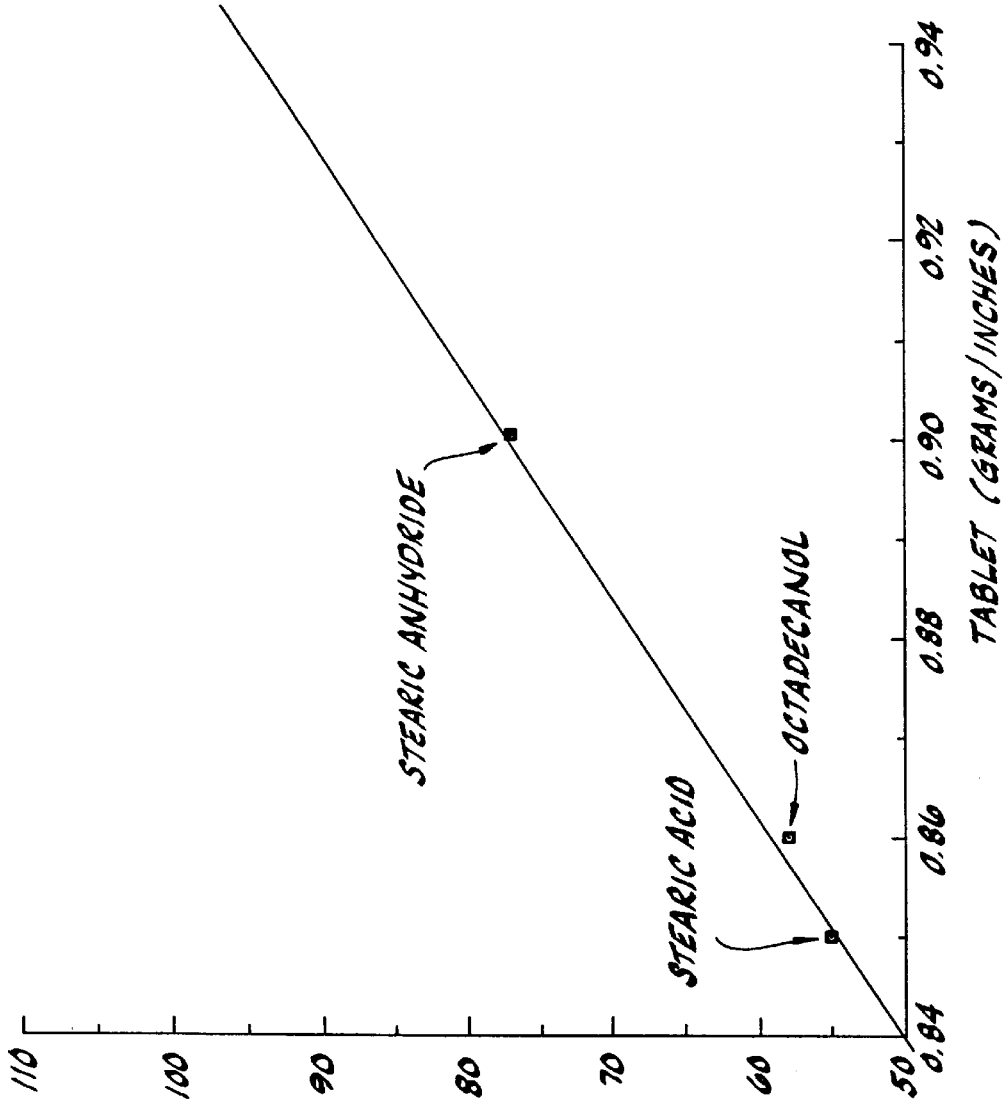
FIG. 7 is a plot illustrating a correlation between the tableting pressure at which liquid is extruded from various pore modification agents and the melting point exhibited by the pore modification agents in the absence of compressive force.
Figure 8:
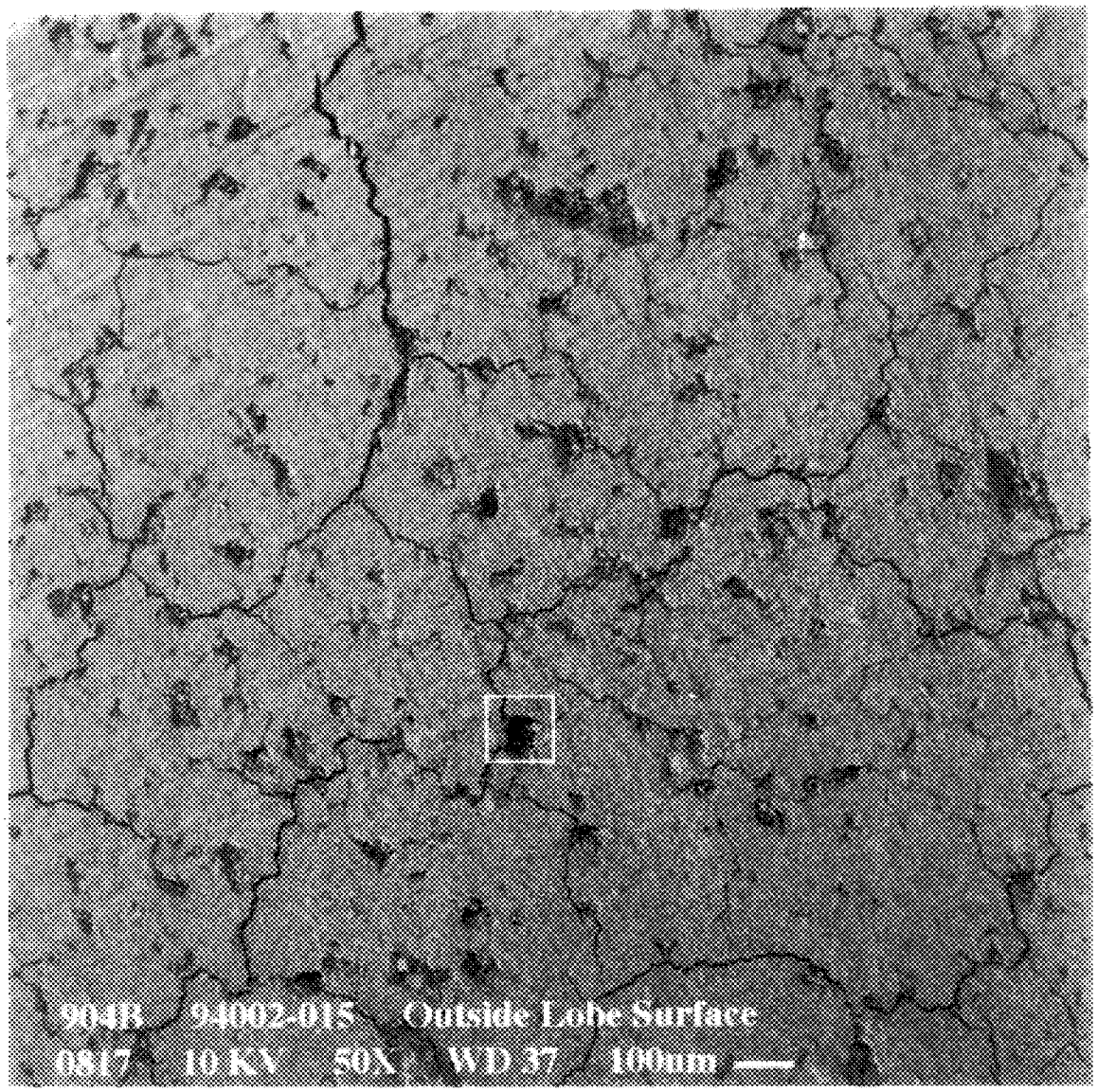
FIGS. 8 to 12 are external photomicrographs of catalyst tablets of the invention showing the incidence of surface holes communicating with the interior of the tablet.
Figure 9:
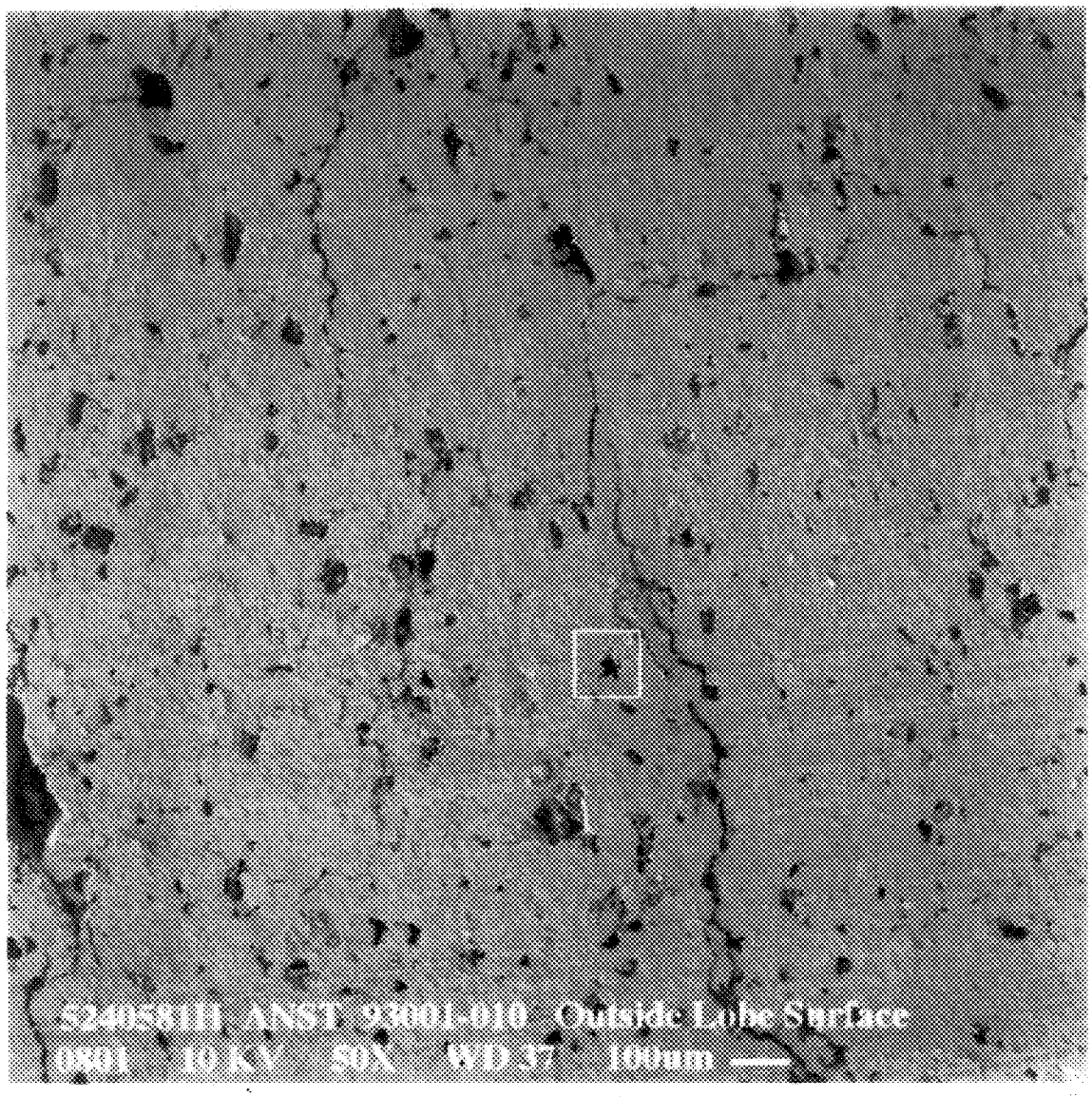
Figure 10:
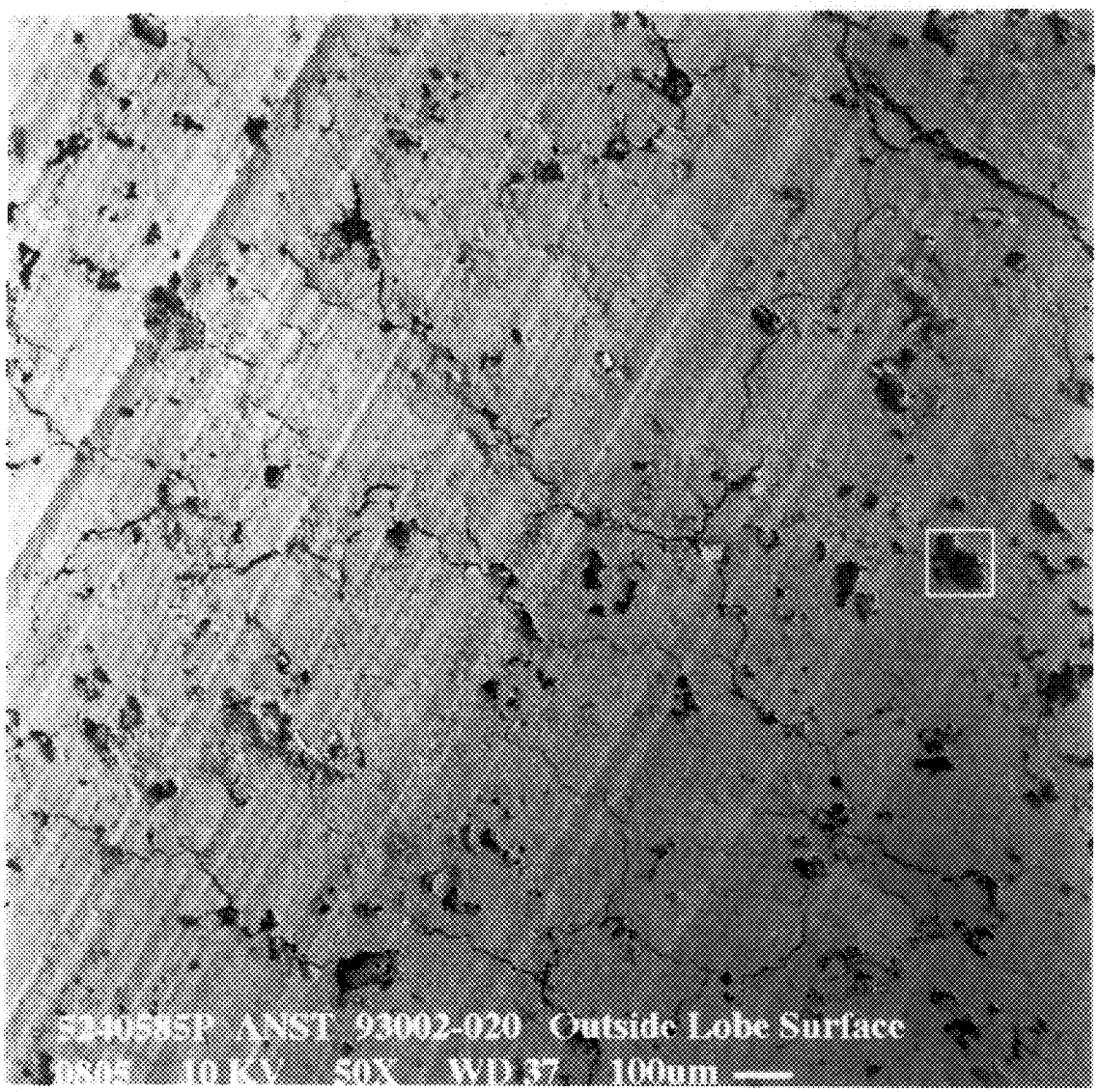

Although the particulate mixture of vanadium/phosphorus oxide precursor and pore builder can be formed directly into a precursor body which is heat treated for activation, a preferred method involves a preliminary slugging and granulation step. Thus, the pore-modified precursor mixture is compressed to produce a slug of material, for example, in the form of a cylinder, the slug is then granulated, and the granulated composition is compressed in a die to form the tablet, pellet or other shaped precursor catalyst body. Where a fatty acid pore builder such as stearic acid is used, the slug is preferably compressed to a density of between about 1.40 and about 1.50 g/cc. Compressing to significantly higher densities may result in undesired expression of liquid phase from the fatty acid pore builder, which may cause a change in the number and size distribution of pore builder particles and in turn have a detrimental effect on the porosity of the final catalyst product. The tolerable degree of compression may be generally correlated with the pore builder's melting point in the absence of compression. FIG. 7 illustrates this relationship for a number of exemplary pore modification agents. Expression of liquid is indicated for combinations of melt point and tablet compression whose co-ordinates fall to the right of and below the solid line of FIG. 7, while expression of liquid is avoided for combinations of normal melting point and tablet compression whose co-ordinates fall to the left and above the solid line.

Granulation of the slug may be carried out by the mechanical action of mill knives operated in conjunction with a retaining screen having holes which pass the desired size granule. Preferably the granules are on the order of 200µM to 1 mm in size, as produced by passage through a screen having 1/16" to 1/8", preferably about 3/32" holes. The tablet or other shaped body formed by compression of these granules comprises a structure of mixed particulate phosphorus/vanadium oxide structure and particulate pore builder. The shaped precursor body has a minimum principal dimension of at least about 1/8", preferably 5/32" to 1/2", and thus a volume per catalyst body of at least 0.02 cc, more preferably at least about 0.03 cc, more preferably at least about 0.05 cc.

Figure 4:
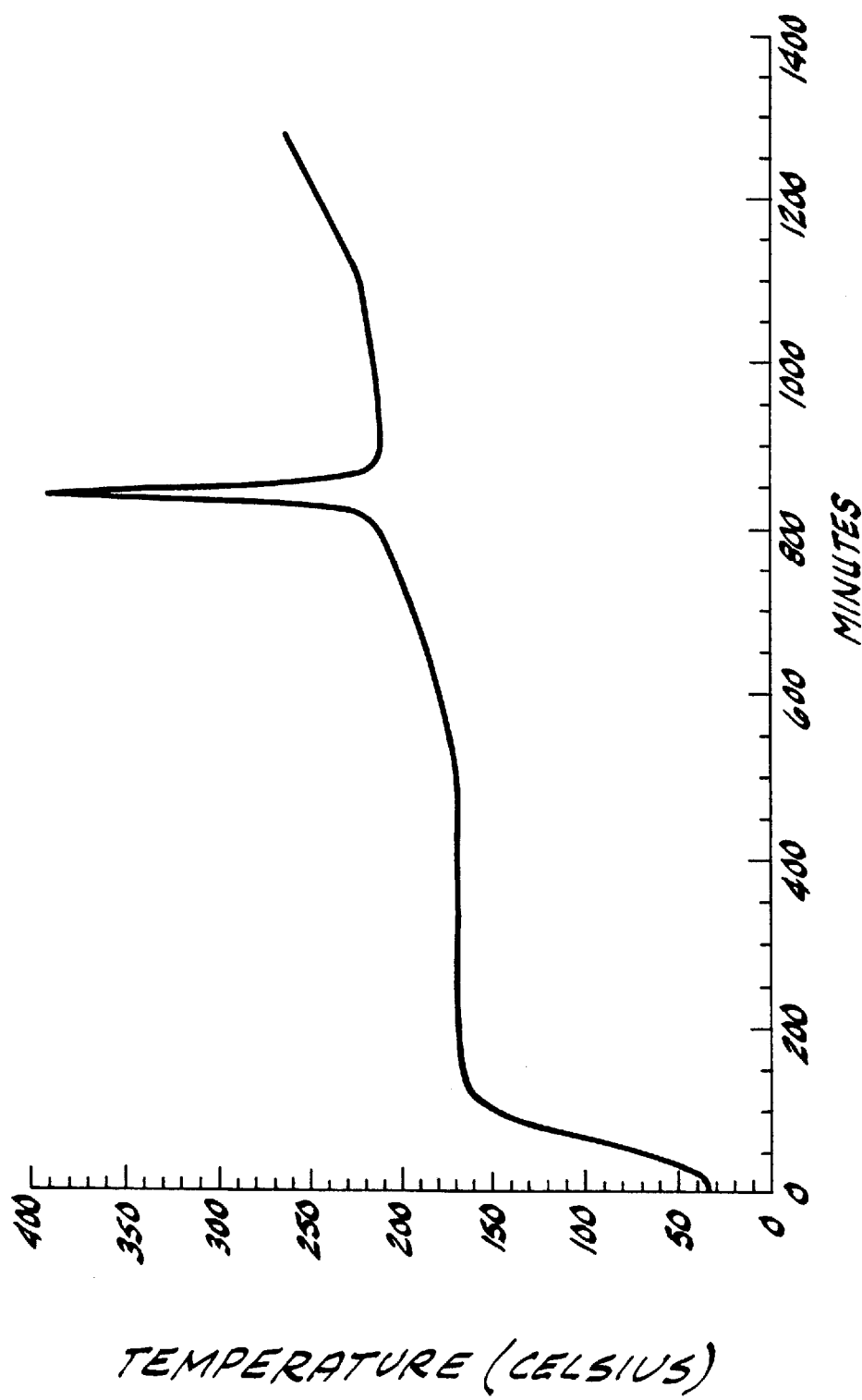
FIG. 4 is a copy of a temperature recording chart illustrating an excessive exotherm in the removal of pore builder, which resulted in the formation of a catalyst having less than desired activity.
Figure 5:
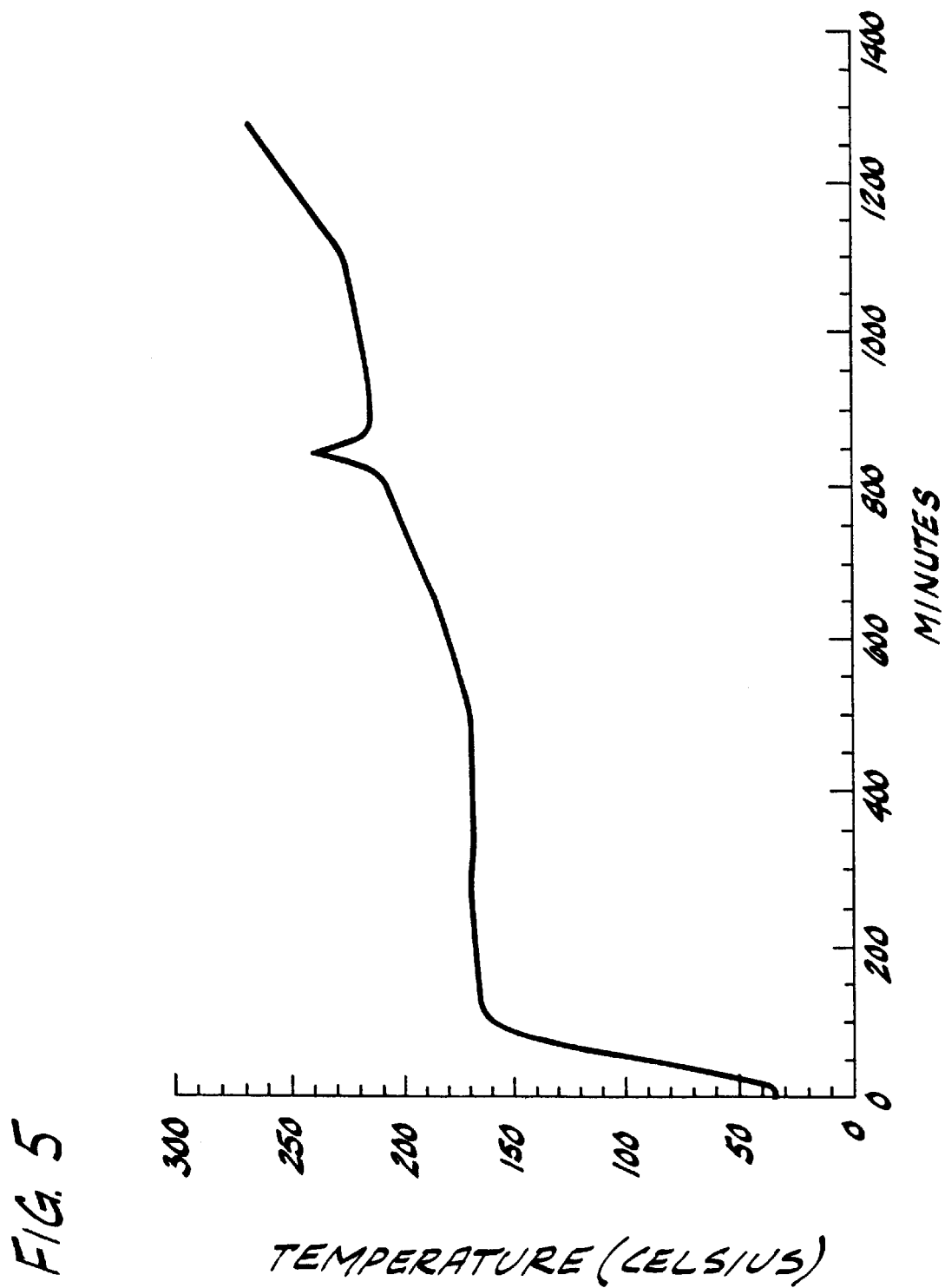
FIG. 5 is a copy of a temperature recording chart illustrating a tolerable temperature excursion in removal of pore modification agent in accordance with the process of the invention.
Figure 6:
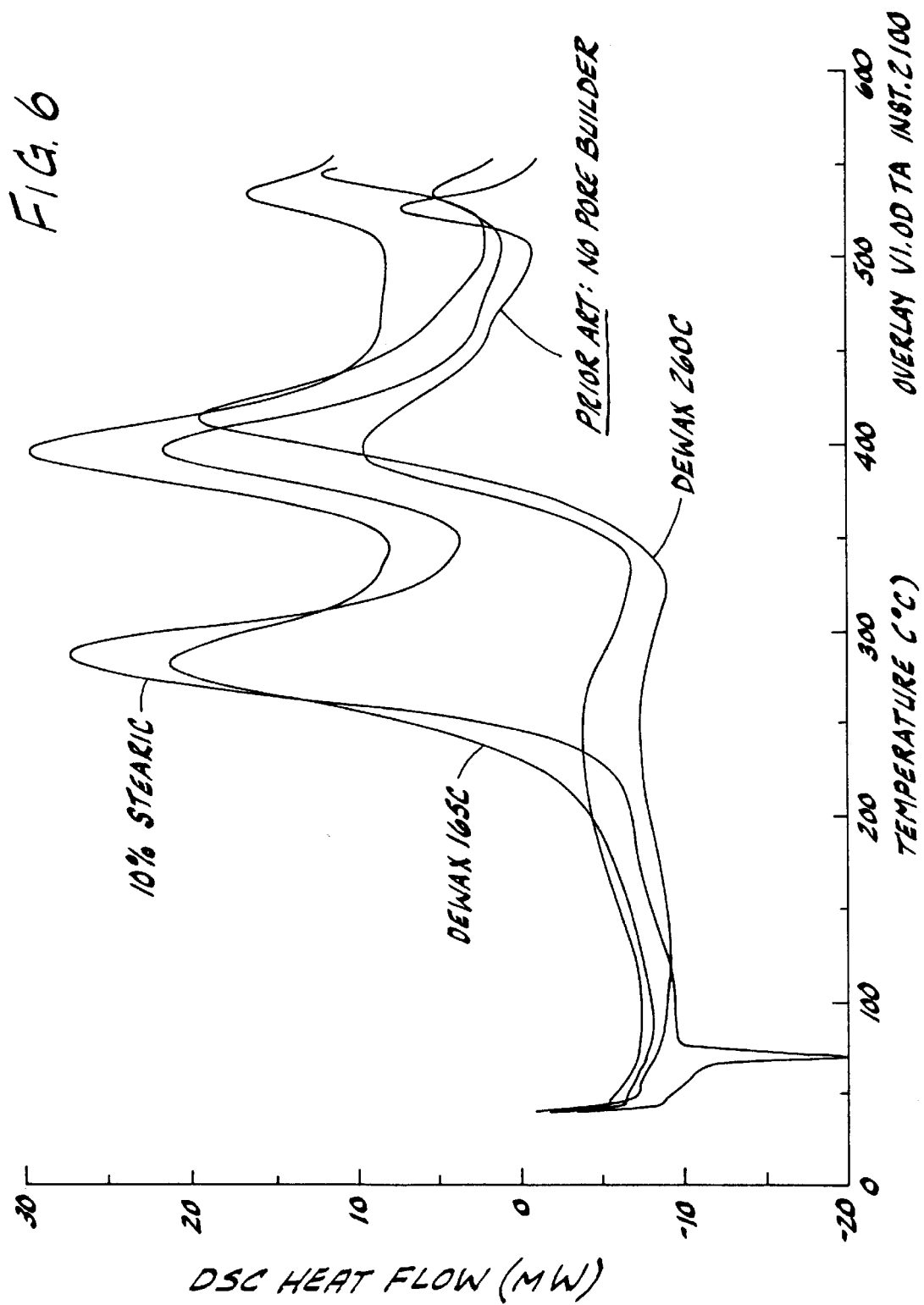
FIG. 6 is an overlay of several differential scanning calorimetry curves, one for a tableted vanadium/phosphorus/ oxide catalyst precursor composition prepared in accordance with the invention, the others for tableted precursors prepared without a pore builder or with inadequate removal of the pore builder prior to differential scanning calorimetry.

The tablets or other shaped precursor bodies are heated under conditions effective for removal of the pore builder from the bodies without causing an exotherm sufficient to result in excessive premature dehydration or reduction of the vanadium/phosphorus oxide precursor composition. A stripping gas is caused to flow over the shaped bodies to provide a driving force for mass transfer and to carry away the pore builder volatilized by heating. A variety of conditions can be utilized in removal of the pore builder, depending in significant part on its nature. Generally, it is preferred that the conditions be controlled so that the precursor bodies are not heated to a temperature higher than about 275° C., more preferably not higher than about 255° C. However, brief excursions to higher temperatures can be tolerated so long as neither excessive dehydration nor significant reduction is suffered. In most systems, dehydration is not excessive if the temperature does not rise to more than about 300° C. for more than about 5 to about 20 minutes. FIG. 5 illustrates a modest exotherm of the type that can be tolerated during removal of pore builder. By contrast, FIG. 4 illustrates an excessive exotherm which damages the catalyst structure.

Where the pore builder has a melting point significantly lower than the temperature at which it is removed, the precursor bodies are preferably heated to a temperature above the melting point but below the lowest temperature at which the pore builder is subject to substantial thermal degradation or oxidation by the catalyst precursor or components of the atmosphere to which the shaped body is exposed during heating. Preferably, the shaped body is heated to a temperature at which the vapor pressure of the pore builder is above 1 mm Hg, but well below 300° C. Most of the pore builders of interest may be removed at or near atmospheric pressure by heating to a temperature in the range of between about 150° C. and about 250° C. Where the pore builder has a vapor pressure of <1 mm Hg in the range of between about 150° C. to about 200° C., the shaped body is preferably heated, at gradually increasing temperature, to a terminal temperature in the range of between about 200° C. and about 250° C. The stripping gas preferably flows over the catalyst body at a velocity of at least about 25 cm/sec., more preferably between about 50 and about 75 cm/sec. Satisfactory removal of pore builder can be realized over a wide range of pressure, including atmospheric and above. A pressure slightly below atmospheric is preferred.

In order to prevent excessive dehydration of the VPO structure, it is important not only to avoid excessive exotherms that can result from oxidation of the pore builder with oxygen from the stripping gas when the catalyst precursor is heated too fast, but also to remove as much pore builder as possible at relatively low temperature, below the temperature at which oxidation of the pore builder may result from abstraction of oxygen from the VPO catalyst precursor structure. The latter reaction is a particular risk towards the end of the pore builder removal step, at the relatively high temperatures that may be required for lowering the concentration of residual pore builder to a level at which no serious exotherm is experienced in the subsequent catalyst activation stage. Moreover, fairly lengthy exposure to such temperatures may be necessary to eliminate residual pore builder to the extent required for the activation step, without generating an exotherm in the removal step by heating too rapidly. Thus, for example, where the shaped precursor bodies need to be heated to a temperature of 240° C. for removal of residual pore builder by stripping, they are exposed to potential dehydration and reduction not only during the approach to 240° C. but also during the several hours typically required to cool to a temperature below about 150° C. At such temperatures, if the amount of residual pore builder remains too high, the catalyst precursor structure is subject to both dehydration and reduction due to reaction of the pore builder with oxygen abstracted from the crystal VPO lattice. Moreover, where air or other oxygen containing gas is used as the stripping gas, and a substantial exotherm is experienced, the temperature of the VPO precursor may rise so high that once the pore builder has burned off, the catalyst structure becomes oxidized by reaction with oxygen in the stripping air, leading to final vanadium oxidation state well above the desired range. Thus, as discussed in more detail below, the bulk of the pore builder is preferably removed at a temperature below the temperature at which it may be subject to rapid oxidation.

It is also important to achieve substantially complete removal of the pore builder before heat treatment of the precursor bodies to produce activated catalyst bodies. When exposed to oxygen during the subsequent heat treatment for activation, residual pore builder may oxidize at an excessive rate, causing an excessive exotherm in that operation which may interfere with the conditions of the heat treatment. Thus, for example, when using the preferred method of activation as described below, it is important that, in the range of about 300° to about 400° C., the rate of increase in the temperature of the precursor bodies is not faster than about 2° to about 12° C. per minute. If any significant residual amount of pore builder is present, an exotherm may develop which increases the heating rate of the precursor bodies to well above 12° C. per minute, even where they are heated in an oven in which the rate of increase of the air or other stripping gas temperature is well within the 2° to 12° C./min. range. Accordingly, the removal step should be continued until at least 80%, preferably at least about 85%, of the pore builder has been removed, as indicated, for example, by measured weight loss during the removal step.

Severe exotherms can also be experienced in the pore builder removal step, so that the rate of temperature increase must be carefully controlled in that step as well. Many pore builder materials are subject to uncontrolled oxidation if the precursor bodies are heated too rapidly, especially at temperatures in the upper portion of the range in which pore builder is removed. Rapid oxidation may result from abstraction of oxygen from the crystal lattice, but may be much more severe where air is used as the stripping gas. It has been observed that the precursor bodies can reach temperatures as high as 600° C., essentially destroying the desired crystal structure of the catalyst. Even at temperatures well below 600° C., a substantial exotherm may result in excessive dehydration of the crystalline VPO structure. In the presence of air the oxidation state of the vanadium may be increased substantially above the preferred 4.06 to 4.3 range, while in the absence of air, the vanadium oxidation state may be reduce below that range. FIG. 4 illustrates an excessive exotherm of the type that may be generated in the course of pore builder removal.

The tendency to uncontrolled oxidation and generation of excessive exotherms is believed to be a function of the nature of the pore builder, the temperature and the amount of pore builder remaining in the precursor bodies at a given temperature. Thus, the heating rate may be critical. It has further been observed that certain pore builders are subject to catalytic oxidation in the presence of the VPO precursor beginning at a threshold temperature which varies with the nature of the pore builder. At this temperature, it is understood that oxygens of the VPO crystal lattice become labile and react with the pore builder. Oxygen withdrawn from the lattice by this reaction is replenished by oxygen transferred from the stripping gas. If the amount of remaining pore builder is low when the threshold ("light off") temperature is reached, catalytic oxidation provides a useful and beneficial means of substantially eliminating residual pore builder prior to high temperature heat treatment for transformation of the precursor to active catalyst. This phenomenon may provide a particular benefit when air is used as the stripping gas. In such instance, the pore builder oxidation proceeds at a controlled rate, causing neither excessive dehydration, reduction of vanadium, oxidation of vanadium, or adverse alteration of the crystal structure. However, if the amount of remaining pore builder is too great, catalytic oxidation thereof may generate an excessive exotherm. Thus, it is desirable to remove as much of the pore builder as possible at relatively low temperature.

In a preferred embodiment, therefore, the precursor bodies are initially heated at a modest rate, for example, at a rate such that their temperature increases at between about 1° C. and about 3° C. per minute to a hold temperature at or slightly lower, preferably no more than about 15° C. lower, than the light off temperature for catalytic oxidation of the pore builder in the presence of the precursor. Operation at the light off temperature is acceptable because the oxidation rate at this temperature is slow enough that the reaction heat can be readily removed by the stripping gas, and both bulk and local hot spots are avoided. The precursor bodies are then maintained at the hold temperature for a period of time during which additional amounts of pore builder are removed by evaporation. During the initial heatup and the hold period, the stripping gas serves as a heat source, and the pore builder is removed essentially by evaporation or sublimation, while oxidation is substantially avoided. After the hold period, heating of the precursor bodies is resumed at a very slow rate to the light off temperature, and beyond the light off temperature to the terminal temperature of the pore builder removal step. During the latter phase of the process, it is believed that residual pore builder is removed both by evaporation and catalytic oxidation. In this period, the stripping gas typically serves as a heat sink rather than a heat source, as is indicated by the fact that the temperature of the catalyst bodies ordinarily exceeds the temperature of the stripping gas once the light off temperature for the pore builder has been reached.

Where stearic acid is used as the pore builder, air is preferably used as the stripping gas, and the precursor bodies are heated to increase their temperature at a rate of about 1° C. to about 3° C. per minute from the initial temperature, typically ambient, to a hold temperature not greater than about 170° C., preferably about 165° C. At the velocities discussed above, the air is advantageously recirculated for conservation of energy, a fractional purge stream having a flow volume of 5% to 20% of the circulating rate being withdrawn for disposal of pore builder and pore builder oxidation products. The bodies are maintained at the hold temperature until enough pore builder has been removed so that the heat generated by subsequent catalytic oxidation does not cause an excessive exotherm. More particularly, the catalyst bodies should be maintained at the hold temperature long enough so that any exotherm in the remainder of the pore builder removal step does not exceed a maximum temperature of about 300° C. If desired, pore builder removal during the hold period is monitored by weight loss. After the hold period, heating to increase the temperature of the precursor bodies is resumed at a very gradual rate. The hold period is typically between about 1 to about 10 hours, depending on the nature of the pore builder, the initial pore builder content, and the nature and velocity of the stripping gas. At a volumetric air flow velocity of between about 0.5 and about 20, more preferably about 4 to about 10, liter/sec.-kg catalyst precursor, and a linear velocity of between about 50 and about 75 cm/sec, the hold period for stearic acid is preferably between about 1 and about 7 hours.

After the hold period, the catalyst bodies are heated at a rate effective to progressively remove residual pore builder by oxidation and/or vaporization while avoiding the generation of an excessive exotherm. The rate of removal is a function of the amount of residual pore builder and the temperature. As the temperature increases, the proportion of catalyst sites that are active for oxidation of the pore builder may be visualized as progressively increasing. At a given temperature, the rate of removal of pore builder by oxidation and/or vaporization declines as pore builder is consumed, until the concentration of residual pore builder asymptotically approaches a limiting, essentially irreducible value. Thus, to achieve progressive reduction in pore builder concentration beyond the asymptotic limit at a given temperature, the temperature must be progressively increased. However, the rate of oxidation may become uncontrollably high if the temperature is raised too high or too rapidly at a given residual pore builder concentration. It is critically important that the oxidation rate not reach the point at which local hot spots adversely alter VPO phase structure, or even reach a self-accelerating level at which reaction heat generation rate exceeds the rate of heat removal in the stripping air flowing over the precursor tablets. As a consequence, it is necessary to increase the temperature very gradually to maintain a reasonable rate of removal of residual pore builder while avoiding an excessive exotherm. It has been found that, as the pore builder concentration decreases, it becomes feasible to moderately accelerate the rate of heating until a terminal temperature is reached at which the asymptotic concentration of residual pore builder is low enough so that an excessive exotherm is avoided in the subsequent catalyst activation step.

The exact time/temperature schedule may vary with such parameters as the identity of the pore builder, the stripping air flow velocity, the size and shape of the precursor tablets, the surface to volume ratio of the bed of catalyst bodies in the pore builder removal oven, and the total weight of catalyst precursor bodies relative to the volumetric air flow in the oven. Typically, however, the precursor bodies are heated very slowly, for example, from about 0.5° C. to about 3° C. per hour, preferably about 1° C. to about 2° C. per hour, to a temperature in the range of about 15° to 40° C. above the hold temperature, and thereafter at a rate increasing to 10° to 40° C. per hour, preferably about 15° to about 25° C. per hour, at temperatures ranging from around 200° C. to the terminal temperature (240° to 260° C. in the case of stearic acid). Thereafter, the precursor bodies are cooled to ambient temperature, preferably in about 0.5 to 2 hours. The precise temperature schedule is controlled so that the vanadium oxidation state is not reduced to below 3.8. For example, a large batch of precursor bodies containing a stearic acid pore builder may be heated on the following schedule:

| | |
|---|---|
| ambient to 170° C. | 1 hour |
| 170° C. hold | 2 hours |
| 170° C. to 185° C. | 15 hours |
| 185° C. to 199° C. | 7 hours |
| 199° C. to 255° C. | 2 hours |
| cool to ambient | 2 hours |

A smaller batch may be treated on a somewhat more aggressive schedule, for example

| | |
|---|---|
| ambient to 165° C. | 1 hour |
| 165° C. hold | 2 hours |
| 165° C. to 199° C. | 17 hours |
| 199° C. to 255° C. | 2 hours |
| cool to ambient | 2 hours |

The entire cycle has been found to extend for 15 to 35 hours, optimally 23 to 28 hours.

Removal of pore builder using air as the stripping gas, and following the temperature schedule outlined above, has been found to avoid the problem referred to as "overstripping" in Andrews U.S. Pat. No. 5,275,996. Whether overstripping results from an excessively reducing atmosphere, from oxygen abstraction resulting from bonding between the VPO substrate and carboxyl groups of a fatty acid pore builder, thermally initiated oxygen abstraction reactions, or both, it has been found that this problem is avoided in the process of the present invention wherein the heating rates are very strictly controlled and air is used as the stripping gas.

By use of air as a stripping gas under the controlled temperature conditions of the invention, even non-volatile pore builders such as methyl cellulose may be effectively used without adverse effect on the final properties of the catalyst. According to the methods of the prior art, it was necessary to burn out such non-volatile pore builders in a fashion which resulted in an excessive exotherm. More specifically, catalyst bodies containing cellulosic type pore builders were heated to rather elevated temperatures in the presence of air, causing decomposition of the pore builder into volatile fragments which were then burned in the air, causing the temperature of the catalyst body to rise far above 300° C., with consequently excessive and premature dehydration. However, by stripping with dilute oxygen-containing gas under conditions below the flammable range, cellulosic pore builders can be entirely removed at temperatures substantially below 300° C. without excessive dehydration or other adverse effect on the precursor crystal lattice.

As indicated, brief temperature excursions as high as 300° C. may be tolerated if the energy absorbed by the precursor body is not such as to cause excessive dehydration during the removal step.

Where the pore builder comprises a relatively volatile compound such as naphthalene, or other polynuclear organic which is free of polarity or functional groups that would generate high energy bonds with the precursor substrate, it may be removed by stripping at temperatures, below about 170° C., at which the oxygen atoms of the precursor crystal lattice are essentially non-labile and the vanadium is not subject to reduction in its oxidation state. Where the pore builder is removable at such modest temperatures, it may not be necessary to heat to the threshold temperature at which catalytic oxidation of the pore builder is initiated in the presence of the catalyst precursor. However, provided that the substantial bulk of the pore builder is removed by evaporation below the light off temperature, catalytic oxidation may be relied on to remove residual pore builder.

Regardless of which of the above described methods is used, the pore builder is removed from the shaped porous body, leaving a porous, gas-permeable structure containing a substantial fraction of macropores, as discussed above. When the pore builder is removed using the extended heating cycles described hereinabove, any residue of carbon, ash or adsorbed organic species at the internal surfaces of the catalyst is reduced to a practical minimum. Thus, when the precursor is subsequently transformed into active catalyst at temperatures in excess of 300° C., the highest feasible catalyst activity is realized. More particularly, the catalyst surfaces are not exposed to uncontrolled exothermic temperature excursions which may otherwise cause the catalyst temperature to rise more rapidly than about 2 to 12° C. per minute during the ramp heating from 300° to 400° C. as described in more detail hereinbelow.

Where a pore builder is burned out of a catalyst tablet by previously known methods, the internal surfaces are exposed to combustion temperatures, which are substantially in excess of the temperatures at which transformation of the catalyst precursor to active catalyst is effectively conducted. By contrast, in the process of the invention, the benefit of a substantial distribution of macropores is achieved, while the adverse effect of carbon deposits, physisorbed or chemisorbed organic species, or exposure of the pore surfaces to excessive temperatures, is avoided. Residual carbon or organic material may not be entirely eliminated, but the residual amount per unit surface area is small enough that, by careful control of the heating rate during the catalyst activation step, the residual carbonaceous material is oxidized at rate which does not cause a substantial exotherm, and does not result in either reduction of vanadium, untoward dehydration of the VPO precursor, loss of effective B.E.T. surface area, or adverse effect on the VPO crystal structure.

Figure 2:
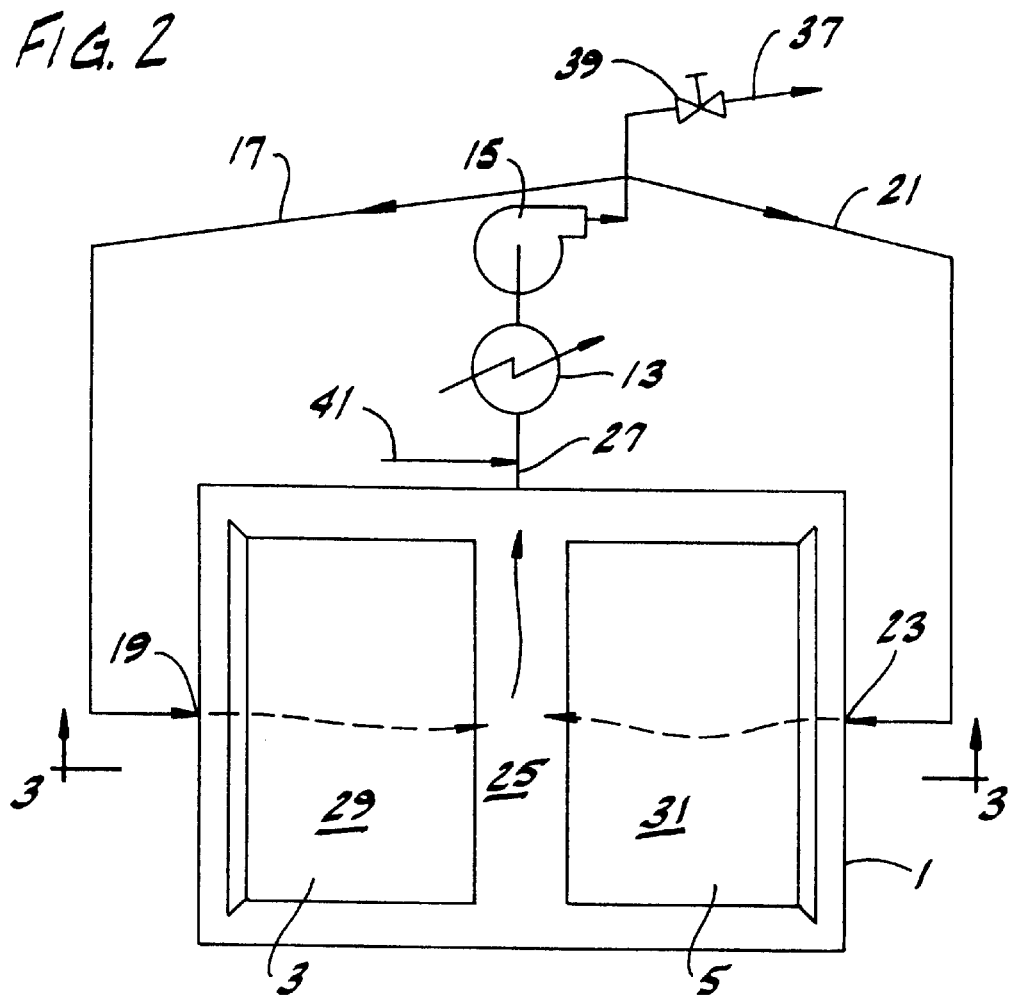
FIGS. 2 and 3 are schematic plan and sectional (along line 3—3) elevation diagrams, respectively, showing an apparatus useful in the removal of a pore modification agent from a tableted catalyst precursor composition and recovery of the pore modification agent.
Figure 3:
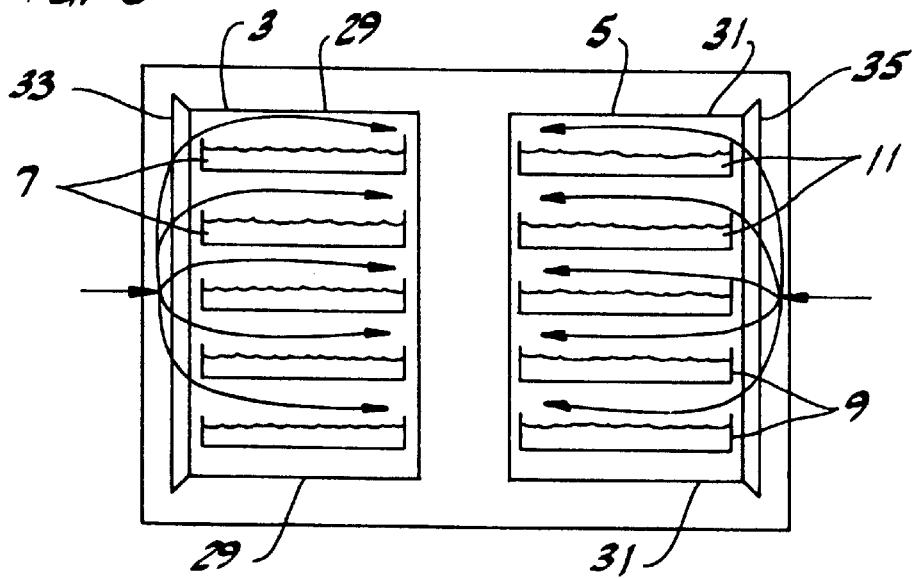

A system for removal of a pore builder is illustrated in FIGS. 2 and 3. In the apparatus shown, an oven 1 contains a pair of racks 3 and 5, each rack holding a plurality of trays 7, 9, and each tray in turn containing a relatively thin layer of shaped porous bodies 11 comprising the catalyst precursor composition containing the pore builder within their pores. Stripping air is circulated through oven 1 and an indirect heat exchanger 13 by means of a blower 15.Air exiting blower 15 is divided between a gas duct 17, which communicates with an air inlet 19 on one side of oven 1, and a gas duct 21, which communicates with an inlet 23 on the other side of the oven opposite inlet 19. Rack 3 is located on the side of the oven adjacent inlet 19, rack 5 is located adjacent inlet 23, and a space between the racks constitutes a plenum 25 for collection of air circulated over the trays for return to the blower via a gas exit 27 of the oven and heat exchanger 13.

Each rack 3, 5 is open on the sides thereof facing the walls of the oven in which the stripping gas inlets 19 and 21 are located, but is covered with sheet metal walls 29, 31 on the top bottom, and the sides facing the other two walls of the oven. Thus, an enclosed "tunnel" is formed having one side open for inflow of stripping air and an opposite side open for exit of air containing pore builder stripped from the shaped catalyst bodies. On the inlet ("upwind") side of each rack, the sheet metal walls are extended beyond the edge of the rack and flared outwardly to form a louver 33, 35 to capture as much air as possible coming from the oven recirculating blower and direct it into the "tunnel" formed by walls 29, 31, thus providing the most desirable air flow over the catalyst precursor shaped bodies on the trays in the rack. Though not indicated in the drawing, each rack may contain two vertical arrays of trays, one adjacent the upwind and the other adjacent the downwind openings in the "tunnel."

In accordance with the pore building process, air or other stripping or purge gas is passed over trays 7, 9 of shaped porous bodies for removal of vaporized pore builder from the shaped bodies. The stripping air is heated by indirect heat transfer in heat exchanger 13, the heat of vaporization of the pore builder being provided by direct heat transfer from the stripping air. The stripping gas flows over the trays at a velocity in the range noted above. In a preferred embodiment, as illustrated, the gas flows both over and under a relatively thin, e.g., 1" thick layer of precursor bodies. The pressure of the stripping gas and temperature of the shaped bodies falls within the ranges outlined above. During the concluding phase of the pore builder removal cycle, oxygen in the stripping gas may participate in controlled catalytic oxidation of residual builder while preventing abstraction of labile oxygens and reduction of vanadium. As noted above, air is preferably used. To conserve energy the air is recirculated by means of a blower 15. A purge stream is discharged through line 37 and valve 39, while makeup air is drawn in through line 41. If desired, the purge may be regulated on a programmed basis at a rate proportional to the rate of vaporization/oxidation of pore builder, but is conveniently set at a fixed rate which preserves a substantial driving force for mass transfer during periods in which the rate of pore builder removal is at a maximum. The purge stream is conveyed to a combustion chamber where it is burned at high temperature to produce an innocuous exhaust gas comprising water vapor and carbon dioxide.

After removal of the pore builder, the shaped catalyst body is subjected to heat treatment to convert the catalyst precursor composition to active catalyst as described above. Pore-built catalysts and processes for preparing such catalysts are described in copending and coassigned application Ser. No. 08/306,489 now U.S. Pat. No. 5,641,722, Attorneys Docket No. HTS 7826, which is expressly incorporated herein by reference.

Because of the apparent presence of residual pore builder, or carbon resulting from coking of the pore builder during the pore builder removal step, it is important to control the rapid heatup rate of the precursor bodies themselves within the aforesaid 2° to 12° C. range. To keep the rate of temperature increase within such range, the oven in which the calcination takes place is preferably heated at a rate no higher than about 3° C., more preferably not more than about 2° C. As noted above, a heatup rate approaching 12° C. per minute may result in a substantial exotherm. Where stearic acid is used as the pore builder, the optimal heatup rate is about 1.8° C. per minute. The acceptable level of residual pore builder remaining after the pore builder removal step may be defined with reference to transformation of the precursor to active catalyst at a standard or reference heating rate of 1.8° C. between 300° and 400° C. A maximum acceptable level of residual pore builder is that concentration which does not result in an exotherm that adversely alters or affects the VPO structure when the shaped bodies are heated for activation in the presence of air, steam or nitrogen under such reference conditions.

Figure 13:
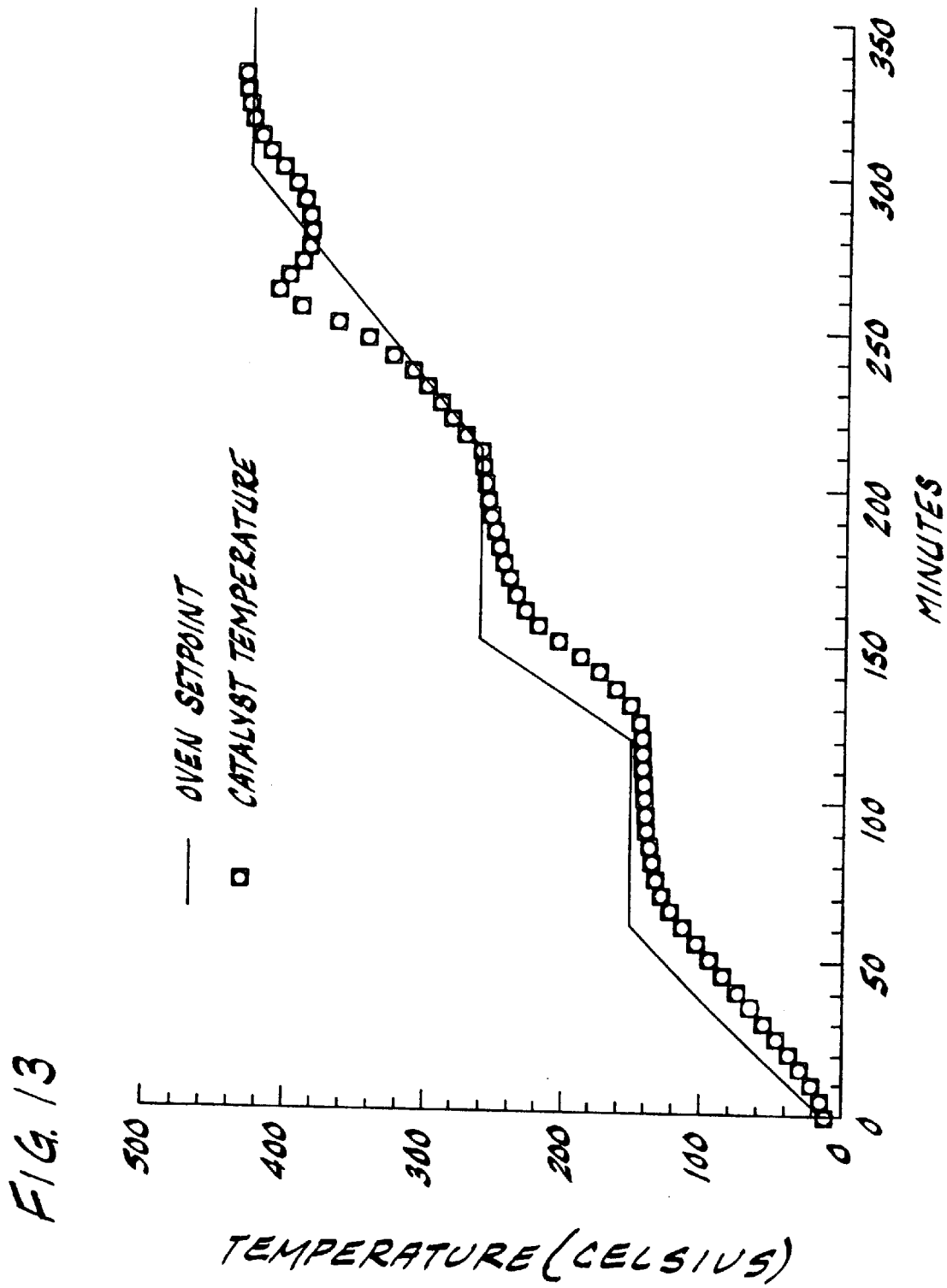
FIG. 13 is a plot of catalyst temperature and oven temperature vs. time during the preparation of an activated catalyst in accordance with the process of the present invention.

FIG. 13 illustrates typical profiles of both catalyst body temperature and oven temperature for the catalyst activation steps of the process of the invention. It may be noted that the circulating gas serves as a heat source in supplying the heat of vaporization during the pore builder removal step, but functions as a heat sink during the activation step when residual pore builder is oxidized. The circulating gas may also serve as a heat sink whenever a modest exotherm is incurred in removal of pore builder, for example, as illustrated in FIG. 5.

It has been discovered that both the removal of pore builder and the transformation of catalyst precursor bodies to active catalyst bodies can be conducted in the same oven, without removal of the catalyst bodies from the oven between the end point of the pore builder removal step and the beginning of the transformation step. As indicated above, the end point of the pore builder removal step is determined by the residual concentration of pore builder, and/or carbonaceous degradation products of the pore builder, which must be reduced to such a level that no excessive exotherm is experienced in the subsequent activation step. To assure against such an exotherm, it is necessary that at least 80% by weight of the pore builder originally present be removed from the precursor bodies by raising the terminal temperature of the precursor bodies at the end point to at least about 200° C., preferably in the range of 240° to 260° C. Advantageously, the precursor bodies are not cooled below about 100° C. in the period between the end point of the removal step and the beginning of the activation step. More preferably, the precursor bodies are not allowed to cool by more than 50° C. during that period. Using this preferred embodiment of the process of the invention, enhanced productivity is achieved by avoiding the steps of cooling the precursor bodies, transferring them from one oven to another, and reheating them in the first step of the activation process. Substantial energy savings are also realized.

Such pore-built catalysts have been demonstrated to afford enhanced yields in the range of 2–4% higher than otherwise comparable catalysts that have not been processed to provide the proportions of macropores described hereinabove. The catalysts of the invention are also superior to catalysts which contain a similar proportion of macropores, but have been prepared by burning a pore builder out of a catalyst precursor tablet or pellet under conditions which expose the catalyst body to a substantial exotherm. Careful removal of the pore builder under mild conditions avoids the deposit of carbon on the active surfaces of the catalyst pores or abstraction of labile oxygens and reduction of the vanadium oxidation state, and further avoids interference with the critical chemistry by which the precursor is transformed to high surface area active catalyst under the controlled heating conditions described above.

FIGS. 8–12 are photomicrographs showing the external surface of a catalyst tablet of the invention. Distributed over the surface of this tablet are exit holes through which the pore builder has escaped during the process of its removal. By removal of the pore builder under mild conditions, a distribution is obtained in which the exit holes greater than about 2 microns in diameter have a density of at least about 75/mm$^2$, more preferably at least about 100/mm$^2$ on the external surfaces of the catalyst bodies. These holes are in communication with the interior of the body and further facilitate the ingress of reactant gases and egress of product gases.

Pore-built molybdenum-modified catalysts can also be prepared in the manner described in U.S. Pat. No. 5,275,996, herein incorporated by reference. Catalysts described therein are such that, of the total pore volume, at least about 5%, preferably at least about 8%, is constituted of pores having a diameter greater than 0.8 micron. Generally, the proportion of pore volume constituted of 0.8+ micron pores is between about 8% and about 50%, preferably between about 10% and about 30%. The precursor includes between about 4% and about 16%, preferably between about 8% and about 12%, by weight of pore builder. The VPO precursor particles used in preparing such pore-built catalysts have a mean diameter in the range of between about 50 to 200 microns, most often in the range of between about 80 and 110 microns. It is generally preferred that the mean particle diameter of the pore builder be between about 50 and about 2000 microns, more preferably between about 100 and about 550 microns.

The reaction to convert non-aromatic hydrocarbons to maleic anhydride requires only contacting the hydrocarbons admixed with a molecular oxygen-containing gas (including molecular oxygen), such as air or molecular oxygen-enriched air, with the catalyst at elevated temperatures. In addition to the hydrocarbon and molecular oxygen, other gases such as nitrogen and steam, may be present or added to the reactant feedstream. Typically, the hydrocarbon is admixed with the molecular oxygen-containing gas, preferably air, at a concentration of about one mole percent to about 10 mole percent hydrocarbon and contacted with the catalyst at a space velocity of about 100 hr$^{-1}$ to about 4000 hr$^{-1}$ at a temperature between 300° C. and about 600° C., preferably 1500 hr$^{-1}$ and about 325° C. to about 425° C., to provide an excellent yield and selectivity to maleic anhydride.

The pressure is not critical in the reaction to convert non-aromatic hydrocarbons to maleic anhydride. The reaction may be conducted at atmospheric, superatmospheric, or subatmospheric pressure. It will generally be preferred, however, for practical reasons to conduct the reaction at or near atmospheric pressure. Generally, pressures of from about 1.013×10$^2$ kPa-G (14.7 psig, 1 atmosphere) to about 3.45×10$^2$ kPa-G (50 psig) may be conveniently employed.

Maleic anhydride produced by the catalysts of the instant invention may be recovered by any means well known to those skilled in the art. For example, maleic anhydride can be recovered by direct condensation or by absorption in suitable media with subsequent separation and purification of the anhydride. In an aqueous purification system, the reduced amount of acrylic acid formed in producing maleic anhydride reduces aqueous waste removal restrictions on the process such that more butane can be fed into the process.

A large number of non-aromatic hydrocarbons having from four to 10 carbon atoms can be converted to maleic anhydride using the catalysts of the instant invention. It is necessary that the hydrocarbon contain not less than four carbon atoms in a straight chain. As an example, the saturated hydrocarbon n-butane is satisfactory but isobutane (2-methyl-propane) is not satisfactory for conversion to maleic anhydride although its presence is not harmful. In addition to n-butane, other suitable hydrocarbons include the pentanes, the hexanes, the heptanes, the octanes, the nonanes, the decanes, and mixtures of any of these, with or without n-butane so long as an unbranched chain having no less than four carbon atoms is present in the saturated hydrocarbon molecule.

Unsaturated hydrocarbons are also suitable for conversion to maleic anhydride using the catalyst of the instant invention. Suitable unsaturated hydrocarbons include the butenes (1-butene and 2-butene), 1,3-butadiene, the pentenes, the hexenes, the heptenes, the octenes, the nonenes, the decenes, and mixtures of any of these with or without saturated hydrocarbons such as n-butane, as long as the requisite unbranched C$_4$ hydrocarbon chain is present in the molecule.

Cyclic compounds such as cyclopentane and cyclopentene are also satisfactory feed materials for conversion to maleic anhydride.

Of the aforementioned feedstocks, n-butane is the preferred saturated hydrocarbon and the butenes are the preferred unsaturated hydrocarbons, with n-butane being the most preferred of all feedstocks.

It will be noted that the aforementioned feedstocks need not necessarily be pure substances, but can be technical grade hydrocarbons.

The principal product from the oxidation of the aforementioned suitable feed materials is maleic anhydride although significant amounts of by-products may also be produced when the feedstock is a hydrocarbon containing more than four carbon atoms.

The equilibrated catalysts of the invention exhibit a weight/area productivity of at least about 3.5 mg maleic anhydride/m$^2$-hr and/or a weight/weight productivity of at least about 100 g maleic anhydride/kg.cat.-hr. when contacted with a gas containing 2.4% by volume n-butane in air, at a gas flow volume to catalyst weight ratio of 2180 cc/g-min. under a pressure of 1.055×10$^2$-kPa-G, and at a temperature sufficient to maintain a hydrocarbon conversion of 85 mole percent. When employed in a commercial fixed bed maleic anhydride reactor after equilibration, the catalyst may continue to exhibit its maximum productivity for a substantial period of time. Eventually, the activity and productivity of the catalyst begin gradually to deteriorate, but a catalyst of the invention that has been equilibrated continues to exhibit productivities in excess of the above noted minimums for a substantial period, typically 1000 to 2000 hours, following equilibration. Thus, the catalysts of the invention offer substantial advantages in the commercial manufacture of maleic anhydride.

The following examples illustrate the best currently-known method of practicing this invention.

EXAMPLE 1

To a 12-liter round bottomed flask equipped with a mechanical stirrer having a Teflon paddle, water-cooled reflux condenser with Dean Stark trap, thermometer, and heating mantle, was charged 4997 grams (g) of isobutyl alcohol (IBA), 898 g of 106.86% H$_3$PO$_4$ dropwise with stirring (solution P/V=1.15), 774 g of Kerr-McGee V$_2$O$_5$ (below 40 mesh, granular), and 345 g of oxalic acid dihydrate. Another 1667 g of IBA was added to rinse all of the reagents into the flask giving a total of 6663 g of IBA. The slurry was heated to reflux over a 2-hour period with stirring to produce a moderate vortex. The refluxing slurry was then heated for another 12 hours (overnight), cooled to room temperature, then returned to reflux on the following day. About one-fourth of the IBA was distilled (2.074 liters, L), then heating and stirring were shut off and the slurry allowed to settle. From the settled mixture was removed about one-half of the remaining IBA (3.111 L).

The slurry was then returned to stirring and 27.38 g of 15% molybdenum Hex-Cem (molybdenum salt of 2-ethylhexanoic acid, code 962, commercially available from Om Group) dissolved in 90 g of IBA were added. The slurry was returned to reflux for another 1 hour. The cooled slurry was poured into two trays (4239 g) and dried in a vacuum oven up to 150° C. The recovered weight of dried powder was 1604 g.

The powder was further dried in a box oven with a controlled air treatment slowly up to 260° C. About 1% air in nitrogen was used for treatment up to 240° C., then the air was gradually increased to 100% before ramping on to 260° C. A total of 1501 g of powder was recovered. Elemental analysis of this powder showed 17.40% phosphorus, 26.45% vanadium, and 0.24% molybdenum for a P/V ratio of 1.082 and an Mo/V ratio of 0.0048 (calculated values are P/V= 1.075 and Mo/V=0.0050). The average vanadium oxidation state determined by titration methods was 3.97.

The 260° C. air/heat-treated powder was mixed with 4 weight percent graphite and compacted on a rotary tableting press to produce ½" slugs of about 1.5 g/cm$^3$ average bulk density. These slugs were crushed and sieved to form a granular powder containing particles mostly between 10 and 16 mesh (1.0 to 1.7 mm). The granulated powder was then formed into a tablet diameter of 5/32" with a trilobe shape. For ¼" trilobe tablets, the 260° C. air calcined powder was mixed with 4 weight percent graphite and 10 weight percent Witco Industrene stearic acid and the powder blend was then compressed on a rotary tableting press to produce ½" slugs of about 1.5 g/cc average bulk density. The slugs were processed to produce ¼" trilobe tablets in the same way as the 5/32" tablets. The stearic acid was removed (i.e., dewaxed) by controlled heating in air of the ¼" tablets according to the procedures of U.S. patent application Ser. No. 08/306,489.

Tablets of either 5/32" trilobes or dewaxed ¼" trilobes were then placed in an oven and treated with an air-nitrogen-steam mixture at programmed temperatures according to the methods given in U.S. Pat. No. 5,137,860. The activated tablets produced by this treatment had a BET surface area of 20.4 m$^2$/g, and had a developed BET surface area of 19.7 m$^2$/g upon equilibration in butane-air gas stream at reaction temperatures for selective catalytic oxidation of n-butane to maleic anhydride.

EXAMPLE 2

Solid forms of molybdenum can also be used to prepare the catalysts of this invention. Molybdenum trioxide is available commercially as a fine powder, typically below 20 μm in average particle size. This example demonstrates one method of preparation that leads to an effective use of the molybdenum present for minimizing the acrylic acid content of the reaction product gas in the production of maleic anhydride through selective oxidation of n-butane.

To a 12-liter round bottomed flask equipped with a mechanical stirrer having a Teflon paddle, water-cooled reflux condenser, thermometer, and heating mantle, was charged 6000 grams (g) of isobutyl alcohol (IBA), 905.2 g of 105.95% H$_3$PO$_4$ dropwise with stirring (solution P/V= 1.15), 774 g of Kerr-McGee V$_2$O$_5$ (below 40 mesh, granular), and 345 g of oxalic acid dihydrate. Another 500 g of IBA was added to rinse all of the reagents into the flask.

The slurry was heated to reflux over a 2-hour period with stirring. The refluxing slurry was then heated for 6 hours and cooled to room temperature. With stirring, 9.2 g of MoO$_3$ powder (Climax Molybdenum Grade L, 99.95% molybdic oxide, average particle size of 5.0 μm by Coulter® counter measurements) was added then another 163 g of IBA was used as a rinse to give a total of 6663 g of IBA. The flask was returned to reflux.

About one-fourth of the IBA was distilled (1666 g) from the flask, then heating and stirring were shut off and the slurry allowed to settle. From the settled slurry was removed about one-half of the remaining IBA (2499 g). Some of the added MoO$_3$ powder dissolved in the IBA solution (elemental analysis showed 0.048% Mo in this solution). Catalyst precursor powder prepared by this procedure is known as made by the reflux-cool-reflux (RCR) method.

The cooled slurry was poured into two trays (4491 g) and dried in a vacuum oven up to 150° C. with a purge of nitrogen. The recovered weight of dried powder was 1468 g.

The powder was further dried in a box oven with a controlled air treatment slowly up to 260° C. About 1% air in nitrogen was used for treatment up to 240° C., then the air was gradually increased to 100% before ramping on to 260° C. Elemental analysis of the air treated powder showed 18.39% phosphorus, 27.74% vanadium, and 0.28% molybdenum for a P/V ratio of 1.090 and an Mo/V ratio of 0.0054 (calculated values are P/V=1.075 and Mo/V=0.0075 if no molybdenum were lost to solution). The average vanadium oxidation state determined by titration methods was 3.99.

The 260° C. air/heat-treated powder was mixed with 4 weight percent graphite and compacted on a rotary tableting press to produce ½" slugs of about 1.5 g/cm$^3$ average bulk density. These slugs were crushed and sieved to form a granular powder containing particles mostly between 10 and 16 mesh (1.0 to 1.7 mm). The granulated powder was then formed into a tablet diameter of 3/16" with a trilobe shape and concave ends ("6NC" designation for 5/32" noninterlocking concave shape).

Tablets of the 6NC trilobes were then placed in an oven and treated with an air-nitrogen-steam mixture at programmed temperatures according to the methods given in U.S. Pat. No. 5,137,860. The activated tablets produced by this treatment had a BET surface area of 21.9 m$^2$/g, and had a developed BET surface area of 20.9 m$^2$/g upon equilibration in butane-air gas stream at reaction temperatures for selective catalytic oxidation of n-butane to maleic anhydride.

EXAMPLE 3

In addition to molybdenum-promoted catalysts made by the RCR method in Example 2, vanadium phosphorus oxide (VPO) catalysts of this invention can be promoted with molybdenum using a dry blending procedure. This example demonstrates how drying blending of the VPO precursor with MoO$_3$ leads to a useful catalyst for minimizing the acrylic acid content of the reaction product gas made when n-butane is selectively oxidized to maleic anhydride.

A VPO precursor was prepared that possesses a macrostructure formed on predominantly spheroidal particles comprising radially oriented three-dimensional networks of randomly shaped open cells (cf., U.S. Pat. No. 4,560,674). The powder was prepared as described in Example 1 except no molybdenum-containing chemical was added during isolation of the precursor. The isolated slurry was dried in a vacuum oven at 150° C. then in a box oven with controlled air treatment as the temperature increased slowly up to 260° C. About 1% air in nitrogen was used for treatment up to 240° C., then the air was gradually increased to 100% before ramping on to 260° C. The 260° C. air/heat-treated powder was mixed with 4 weight percent graphite and compacted on a rotary tableting press to produce ½" slugs of about 1.5 g/cm³ average bulk density. These slugs were crushed and sieved to form a granular powder containing particles mostly between 10 and 16 mesh (1.0 to 1.7 mm).

A total of 2481.4 g of granulated powder was blended with 18.6 g MoO₃powder (molybdic anhydride, catalog #A-174, commercially available from Fisher Scientific) then formed into a tablet diameter of 3/16" (6/32") with a trilobe shape (6NC). Tablets were then placed in an oven and treated with an air-nitrogen-steam mixture at programmed temperatures according to the methods given in U. S. Pat. No. 5,137,860. The activated tablets produced by this treatment had a BET surface area of 17.3 m²/g, and had a developed BET surface area of 23.9 m²/g upon equilibration in butane-air gas stream at reaction temperatures for selective catalytic oxidation of n-butane to maleic anhydride.

EXAMPLE 4

Activated VPO tablets having the 6NC shape were charged to a 0.43" inside diameter stainless steel microreactor with exactly 11.7 g per sample. Three samples were evaluated by feeding a 2.4±0.2% butane in synthetic air (21% oxygen and 79% helium) at 15 psig and 1500/hr. GHSV (425 sccm). Each catalyst was run for at least 150 hrs. to reach an equilibrated catalyst state at 85±1% conversion. The temperature of the catalyst bed was adjusted to reach the target conversion level. Maleic anhydride and acrylic acid yields reported were determined using an online gas chromatograph that was calibrated for butane and acrylic acid (maleic anhydride yield reported is "back calculated" from the butane passing unconverted by the catalyst and the by-products (carbon oxides, acetic acid, and acrylic acid). The results are reported in Table 1.

TABLE 1

| Catalyst | Initial Mo/V | Maleic Anhydride Yield, % | Acrylic Acid Content, mole % |
|---|---|---|---|
| Ex. 2 | 0 | 58.4 | 0.011 |
| Ex. 2 | 0.01 | 56.8 | 0.004 |
| Ex. 3 | 0.01 | 56.2 | 0.006 |

The results show unexpectedly that the acrylic acid yield is decreased by about 45 to 65% in the two molybdenum-modified catalysts as compared to the acrylic acid yield produced by the unpromoted catalyst prepared in accordance with the method of Example 2. However, the maleic anhydride yield in the two molybdenum-containing catalysts decreased by about 1.6 to 2.2%.

EXAMPLE 5

As shown in Example 4, addition of a molybdenum-containing chemical to a VPO precursor that is activated for use in the conversion of butane-to-maleic anhydride leads to a decrease in both the acrylic acid and maleic anhydride yields. While the acrylic acid by-product yield reduction is beneficial especially when used in maleic anhydride plants that use an aqueous recovery system for isolating and refining maleic anhydride, the loss of maleic anhydride ("maleic") yield is to be avoided. This example demonstrates another key feature of this invention, namely, the use of the molybdenum-promoted VPO catalyst in a stratified catalyst pack where the yield of acrylic acid ("acrylic") is minimized while at the same time the yield of maleic anhydride is maximized. Reactor data are summarized in tables 2 (molybdenum-modified catalyst from Example 2 with Mo/V=0.01 prepared by the RCR method) and 3 (molybdenum-modified catalyst from Example 1 prepared by the post-decant method).

TABLE 2

Microreactor Data[a] for Various VPO Catalyst Beds Without (non-Mo) and With (Mo) Molybdenum Modifier

| Entry | Catalyst | Bath Temperature, °C. | Maleic Anhydride Yield[b], % | Acrylic Acid Yield, % |
|---|---|---|---|---|
| 1 | 100%[c] non-Mo | 399 | 63.8 | 0.012 |
| 2 | 100% Mo | 378 | 62.1 | 0.004 |
| 3 | Top 50% non-Mo; Bottom 50% Mo | 390 | 61.7 | 0.008 |
| 4 | Top 50% Mo; Bottom 50% non-Mo | 396 | 63.2 | 0.005 |
| 5 | 50% non-Mo/50% Mo Blend | 400 | 63.9 | 0.013 |
| 6 | Top 50% Inert 6 mm Al₂O₃; Bottom 50% non-Mo | 413 | 56.0[d] | 0.014 |
| 7 | 100% Mo as 1 to 2 mm pieces | 380 | 64.0 | 0.005 |

[a]Catalyst samples are in the form of 6NC tablets except where noted and comprise 11.7 g total charge (100% by weight) run at a flow/weight ratio of 2200 (flow in standard cm³ per minute, weight in grams), 15 psig, 2.4% butane at 85% conversion. Gas flow direction is from the bottom to the top of the microreactor.
[b]Relative Maleic anhydride back-calculated yield based on unreacted butane analyzed by gas chromatography.
[c]In this table, catalyst is charged by weight-%.
[d]Yield reported for a conversion of 75.6%. This example shows the acrylic coming out of the second zone relative to that of the first zone. The catalyst was run at a temperature appropriate for 85% butane conversion of an entire reactor charge even though only half of the reactor charge was used.

Additional microreactor data were collected using stratified catalyst beds run under different butane concentrations to demonstrate scope and acrylic acid reduction by placing the molybdenum-containing catalyst in the last zone of the reactor. Table 3 summarizes the results.

TABLE 3

Microreactor Data for 5/32" Trilobe Tablets with Stratified Last Zone-Containing molybdenum-Modifier VPO Catalyst Bed Volumes for Dual VPO Catalyst Packs at Various Reactor Conditions[a]

| %-Volume of Mo-VPO Catalyst in Last Zone | %-Butane | Bath Temperature, °C. | %-Maleic Anhydride Yield[b] | %-Acrylic Acid Yield |
|---|---|---|---|---|
| 0 | 2.40 | 411 | 58.6 | 0.012 |
| 33 | 2.40 | 417 | 58.1 | 0.006 |
| 33 | 2.00 | 410 | 58.8 | 0.004 |
| 33 | 1.65 | 404 | 59.2 | 0.004 |
| 40 | 2.40 | 415 | 57.2 | 0.006 |
| 40 | 2.00 | 409 | 58.2 | 0.004 |
| 40 | 1.65 | 404 | 58.8 | 0.004 |
| 50 | 2.40 | 415 | 57.8 | 0.005 |
| 50 | 2.00 | 409 | 58.4 | 0.004 |
| 50 | 1.65 | 405 | 58.5 | 0.003 |

[a]Catalyst samples charged to 11.7 g total weight and run at 2200 flow/weight ratio (flow in standard cm³ per minute for weight in grams), 15 psig, and 85% conversion.
[b]Reported as relative back-calculated maleic anhydride yield on the basis of butane passing in a gas chromatographic analytical scheme.

The data presented in Table 3 show at least 50% reduction in acrylic acid content is achieved by using a stratified catalyst bed with the molybdenum-modified catalyst located in the last zone of the reactor.

EXAMPLE 6

Catalysts of this invention typically are used in tubular reactors having inside diameters of about 2.10 cm and 335 to 600 cm long. Catalyst packs are made up of two or more catalyst zones with the same or different sizes and shapes. The following two catalyst packs were charged to identical 335.3 cm long reactors with inside diameters of 2.10 cm.

Catalyst Pack 1 (Comparative): 0 to 5.1 cm, ¼" α-alumina inerts; 5.1 to 142.2 cm, blend of 5/32" trilobes of activated VPO without Mo (85 weight-%) and 3/16" α-alumina inerts (15 weight-%); 142.2 to 335.3 cm, 5/32" trilobes of activated VPO without Mo Catalyst Pack 2: 0 to 12.7 cm, ¼" α-alumina inerts; 12.7 to 89.2 cm, ¼" trilobes of activated VPO without Mo; 89.2 to 194.6 cm, blend of 5/32" trilobes of activated VPO without Mo (80 weight-%) and 3/16" α-alumina inerts (20 weight-%); 194.6 to 335.3 cm of 5/32" trilobes of molybdenum-modified activated VPO of Example 1 (about 43 volume-%)

Each catalyst pack was brought up to operating conditions over a 24-hr. period in 1.0% butane at gas hourly space velocities (GHSV) of 1700 to 2000/hr. with 2.4% moisture in the feed gas while limiting the butane conversion to about 80%. Each reactor was then switched to 1.65% butane at about 1670/hr. (GHSV) with inlet and exit pressures of 20.1 and 16.0 psig, respectively. Analytical data were collected using an online calibrated Fourier-transform infrared (FTIR) analyzer. At on stream times of about 4400 and 1400 hours, respectively, comparative data shown in Table 4 were collected.

TABLE 4[a]

| Catalyst Pack Number | 1 | 2 |
|---|---|---|
| % - Butane | 1.65 | 1.65 |
| Bath Temperature ° C. | 398 | 404 |
| Hot Spot Temperature ° C. | 429 | 443 |
| % - Conversion | 85.1 | 85.1 |
| % - Selectivity | 74.2 | 73.1 |
| % - Maleic Anhydride Yield[b] | 60.1 | 59.1 |
| % - Carbon Totals | 102.0 | 102.2 |
| % - Acrylic Acid Yield[c] | 0.029 | 0.010 |

[a]Feed stream contained 6 to 8 ppm of trimethylphosphate.
[b]Relative back-calculated maleic anhydride yield corrected for acrylic and acetic acids in gas stream.
[c]Acrylic acid yields determined from averaged wet-scrubber data using liquid chromatography.

The data show a 1.0% maleic anhydride yield decrease for running the molybdenum-modified catalyst pack 2 while the acrylic acid level for the pack was reduced by 65%.

EXAMPLE 7

Catalysts of this invention have a vanadyl pyrophosphate phase that forms during treatment of the catalyst tablets in a butane/oxygen gas mixture. This active phase as characterized by powder X-ray diffraction has a peak height intensity ratio that is less than about 1.30 for the powder X-ray diffraction d-spacings at 3.86 and 3.14 Å. Catalysts of this invention typically are prepared from alcoholic solutions that afford a poorly crystalline solid precursor catalyst. When the precursor catalyst is activated in an air/nitrogen/steam atmosphere, the precursor phase is converted into primarily a vanadyl pyrophosphate phase. Equilibration of this $(VO)_2P_2O_7$ phase in a butane/oxygen gas mixture leads to further crystallization of the $(VO)_2P_2O_7$ phase. Four butane/oxygen equilibrated catalysts are tabulated below in Table 5. The first listed catalyst was non-molybdenum-modified and was prepared as described in Example 1. The other listed catalysts were molybdenum-modified and were prepared as described in Examples 1, 2 and 3, respectively.

TABLE 5

| Example | | d-spacing Peak Intensities | | Ratio of 3.86 Å/3.14 Å |
|---|---|---|---|---|
| Catalyst | Mo/V | 3.86 Å | 3.14 Å | Intensities |
| Non-Mo, 1 | 0.0000 | 766 | 697 | 1.099 |
| 1 | 0.0048 | 747 | 657 | 1.136 |
| 2 | 0.0054 | 733 | 594 | 1.235 |
| 3 | 0.0075 | 773 | 618 | 1.250 |

While the invention is susceptible to various modifications and alternative forms, specific embodiments thereof have been shown by way of example and are herein described in detail. It should be understood, however, that it is not intended to limit the invention to the particular form disclosed, but on the contrary, the intention is to cover all modifications, equivalents and alternatives falling within the spirit and scope of the invention as defined by the appended claims.

What is claimed is:

1. An active, phosphorus vanadium oxide catalyst for the conversion to maleic anhydride of a non-aromatic hydrocarbon having at least four carbon atoms in a straight chain, said catalyst comprising a shaped body having a volume of at least about 0.02 cc and a B.E.T. surface area of at least about 15 m²/g, and said catalyst containing molybdenum and having a molar ratio of molybdenum to vanadium of between about 0.0020 and about 0.0060.

2. An active catalyst as set forth in claim 1 wherein said molybdenum of said catalyst has an oxidation state of 6+.

3. An active catalyst as set forth in claim 1 having an X-ray diffraction pattern wherein the ratio of the peak height at a d-spacing of about 3.86 angstrom to the peak height at a d-spacing of about 3.14 angstrom is between about 0.8 and about 1.3.

4. An active catalyst for conversion to maleic anhydride of a non-aromatic hydrocarbon having at least four carbon atoms in a straight chain, the catalyst comprising phosphorus, vanadium, oxygen, and molybdenum and having a macrostructure predominantly consisting of radially oriented three-dimensional networks of randomly shaped open cells, the molybdenum being concentrated at the surfaces of the walls of said cells.

5. An active catalyst as set forth in claim 4 comprising a phosphorus vanadium oxide substantially homogeneously distributed throughout the walls of said cells.

6. A fixed catalyst bed adapted for the production of maleic anhydride by passage therethrough of a gas stream initially comprising a mixture of a nonaromatic hydrocarbon having at least four carbon atoms in a straight chain and an oxygen containing gas, said catalyst bed comprising
   a first zone containing a phosphorus vanadium oxide catalyst substantially devoid of active sites comprising molybdenum; and
   a second zone downstream of said first zone with respect to the flow of said gas stream, said second zone comprising a molybdenum-modified phosphorus vanadium oxide catalyst comprising active sites comprising molybdenum.

7. A catalyst bed as set forth in claim 6 wherein maleic anhydride and acrylic acid are produced as said gas stream passes through said catalyst bed, and said gas stream contacts the active catalyst for a time sufficient to eliminate at least about 20% of the acrylic acid from the gas stream.

8. A catalyst bed as set forth in claim 7 wherein from about 20% to about 70% of the acrylic acid is eliminated from the gas stream.

9. A catalyst bed as set forth in claim 7 wherein from about 35% to about 65% of the acrylic acid is eliminated from the gas stream.

10. A fixed catalyst bed adapted for the production of maleic anhydride by passage therethrough of a gas stream initially comprising a mixture of a nonaromatic hydrocarbon having at least four carbon atoms in a straight chain and an oxygen containing gas, said catalyst bed comprising a mixture of the active catalyst of claim 1 and a phosphorous vanadium oxide catalyst substantially devoid of active sites comprising molybdenum.

11. A catalyst bed as set forth in claim 10 wherein maleic anhydride and acrylic acid are produced as said gas stream passes through said catalyst bed, and said gas stream contacts the active catalyst for a time sufficient to eliminate at least about 20% of the acrylic acid from the gas stream.

12. A catalyst bed as set forth in claim 11 wherein from about 20% to about 70% of the acrylic acid is eliminated from the gas stream.

13. A catalyst bed as set forth in claim 11 wherein from about 35% to about 65% of the acrylic acid is eliminated from the gas stream.

14. An active catalyst having a crystal structure corresponding to that of a catalyst that has been prepared and activated by a process comprising the steps of:
blending a phosphorus vanadium oxide powder and a molybdenum-containing powder to form a molybdenum-modified catalyst precursor composition;
forming the molybdenum-modified catalyst precursor composition into shaped bodies, each of said shaped bodies having a volume of at least about 0.02 cc; and
activating the formed molybdenum-modified catalyst precursor composition to transform it into the active catalyst.

15. An active catalyst as set forth in claim 14 wherein the formed molybdenum-modified catalyst precursor composition is activated by the steps of:
(a) heating the formed molybdenum-modified catalyst precursor composition in an atmosphere selected from the group consisting of air, steam, inert gas, and mixtures thereof, to a temperature not to exceed 300° C.;
(b) maintaining the formed molybdenum-modified catalyst precursor composition at the temperature of Step (g) and providing an atmosphere containing molecular oxygen, steam, and optionally an inert gas, the atmosphere being represented by the formula $(O_2)_x(H_2O)_y(IG)_z$ wherein IG is an inert gas and x, y, and z represent mol percent of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere;
(c) increasing the temperature of the formed molybdenum-modified catalyst precursor composition at a programmed rate of from about 2° C./min to about 12° C./min to a value effective to eliminate the water of hydration from the formed molybdenum-modified catalyst precursor composition;
(d) adjusting the temperature from Step (c) to a value greater than 350° C., but less than 550° C., and maintaining the adjusted temperature in the molecular oxygen/steam-containing atmosphere for a time effective to provide a vanadium oxidation state of from about +4.0 to about +4.5; and
(e) continuing to maintain the adjusted temperature in a nonoxidizing, steam-containing atmosphere for a time effective to complete the formed molybdenum-modified catalyst precursor composition to active catalyst transformation to yield the active catalyst.

16. An active catalyst as set forth in claim 14 wherein said active catalyst comprises a shaped body having a volume of at least about 0.02 cc, a phosphorus/vanadium atom ratio of from about 1.05 to about 1.20, a B.E.T. surface area of at least about 15 m²/g, an average vanadium oxidation state of between about 4.06 and about 4.3, a total pore volume of at least about 0.15 cc/g, a normalized apparent shaped body density of between about 1.0 and about 2.0 g/cc, and a crush strength of at least about 4 pounds, at least about 20% of the pore volume of said catalyst being constituted of pores having a diameter between about 0.1 microns and about 3.3 microns, and at least about 40% of the pore volume being constituted of pores having a diameter of less than about 0.1 microns.

17. An active catalyst as set forth in claim 14 wherein said molybdenum-modified catalyst precursor composition corresponds to the formula:

$VO(Mo)_m HPO_4 \cdot aH_2O \cdot b(P_{2/c}) \cdot n(organics)$ wherein m is a number from about 0.002 to about 0.012, a is a number of at least about 0.5, b is a number taken to provide a P/V atom ratio of from about 1.0 to about 1.2, c is a number representing the oxidation number of phosphorus and has a value of 5, and n is a number taken to represent the weight % of intercalated organics component, and said formed molybdenum-modified catalyst precursor composition is transformed into an active catalyst represented by the formula:

$(VO)_2 Mo_m P_2O_7 \cdot b(P_{2/c}O)$ wherein m, b and c are as defined above.

18. A process for the preparation of an active catalyst comprising the steps of:
blending a phosphorus vanadium oxide powder and a molybdenum-containing powder to form a molybdenum-modified catalyst precursor composition;
forming the molybdenum-modified catalyst precursor composition into shaped bodies, each of said shaped bodies having a volume of at least about 0.02 cc; and
activating the formed molybdenum-modified catalyst precursor composition to transform it into the active catalyst.

19. A process as set forth in claim 18 wherein the formed molybdenum-modified catalyst precursor composition is activated by the steps of:
(a) heating the formed molybdenum-modified catalyst precursor composition in an atmosphere selected from the group consisting of air, steam, inert gas, and mixtures thereof, to a temperature not to exceed 300° C.;
(b) maintaining the formed molybdenum-modified catalyst precursor composition at the temperature of Step (g) and providing an atmosphere containing molecular oxygen, steam, and optionally an inert gas, the atmosphere being represented by the formula ti $(O_2)_x(H_2O)_y(IG)_z$ wherein IG is an inert gas and x, y, and z represent mol percent of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere;

(c) increasing the temperature of the formed molybdenum-modified catalyst precursor composition at a programmed rate of from about 2° C./min to about 12° C./min to a value effective to eliminate the water of hydration from the formed molybdenum-modified catalyst precursor composition;

(d) adjusting the temperature from Step (c) to a value greater than 350° C., but less than 550° C., and maintaining the adjusted temperature in the molecular oxygen/steam-containing atmosphere for a time effective to provide a vanadium oxidation state of from about +4.0 to about +4.5; and (e) continuing to maintain the adjusted temperature in a nonoxidizing, steam-containing atmosphere for a time effective to complete the formed molybdenum-modified catalyst precursor composition to active catalyst transformation to yield the active catalyst.

20. A fixed catalyst bed as set forth in claim 6 wherein said second zone comprises molybdenum active sites in a proportion sufficient to reduce the acrylic acid content of the gas stream exiting the catalyst bed as compared to the acrylic acid content of a gas stream leaving a catalyst bed all zones of which are entirely devoid of molybdenum active sites.

21. A fixed catalyst bed as set forth in claim 20 wherein said molybdenum-modified phosphorus vanadium oxide catalyst comprises a shaped body having a volume of at least about 0.02 cc and a B.E.T. surface area of at least about 15 m²/g, said catalyst containing molybdenum in a molar ratio of molybdenum to vanadium of at least about 0.0020.

22. A fixed catalyst bed as set forth in claim 20 wherein the molybdenum-modified catalyst in said second zone contains molybdenum in a molar ratio to vanadium of at between about 0.0020 and about 0.0060.

23. A fixed catalyst bed as set forth in claim 6 wherein said molybdenum-modified phosphorus vanadium oxide catalyst is prepared by a process comprising:

reacting substantially pentavalent vanadium-containing compound with a pentavalent phosphorus-containing compound in an alcohol medium capable of reducing the vanadium to an oxidation state of less than +5;

incorporating molybdenum into the product of the reaction, thereby forming a solid molybdenum-modified precursor composition;

removing the alcohol to produce a dried solid molybdenum-modified precursor composition;

forming shaped bodies comprising said dried solid molybdenum-modified precursor composition; and activating the dried formed molybdenum-modified catalyst precursor composition to transform it into the active catalyst.

24. An active catalyst having a crystal structure corresponding to that of a catalyst that has been prepared and activated by a process comprising:

preparing a slurry comprising a mixture containing a phosphorus-containing compound, a pentavalent vanadium-containing compound and an alcohol medium capable of reducing the vanadium to an oxidation state of less than +5;

heating said mixture such that said vanadium-containing compound is reduced by said alcohol and reacts with said phosphorus-containing compound in said slurry to form a solid vanadium/phosphorus oxide precursor composition comprising mixed oxides of vanadium and phosphorus;

cooling said mixture after formation of said solid vanadium/phosphorus oxide precursor composition;

introducing a source of molybdenum into the cooled mixture containing said solid vanadium/phosphorus oxide precursor composition, and heating a slurry containing molybdenum and said solid vanadium/phosphorus oxide precursor composition to effect incorporation of molybdenum and formation of a solid molybdenum-modified precursor composition;

removing the alcohol to produce a dried solid molybdenum-modified precursor composition;

forming shaped bodies comprising said dried solid molybdenum-modified precursor composition; and activating the dried formed molybdenum-modified catalyst precursor composition to transform it into the active catalyst.

25. An active catalyst having a crystal structure corresponding to that of a catalyst that has been prepared and activated by a process comprising:

preparing a slurry comprising a mixture containing a phosphorus-containing compound, a pentavalent vanadium-containing compound and an alcohol medium capable of reducing the vanadium to an oxidation state of less than +5;

heating said mixture such that said vanadium-containing compound is reduced by said alcohol and reacts with said phosphorus-containing compound in said slurry to form a solid particulate vanadium/phosphorus oxide precursor composition comprising mixed oxides of vanadium and phosphorus;

removing a portion of said alcohol medium from said mixture after formation of said solid vanadium/phosphorus oxide precursor composition; and after removal of said portion of said alcohol, introducing a source of molybdenum into the mixture containing said solid vanadium/phosphorus oxide precursor composition;

incorporating molybdenum into the particulate vanadium/phosphorus oxide precursor, thereby forming a molybdenum-modified precursor composition;

removing alcohol to produce a dried solid molybdenum-modified precursor composition;

forming shaped bodies comprising said dried solid molybdenum-modified precursor composition; and activating the dried formed molybdenum-modified precursor composition to transform into the active catalyst.

26. An active catalyst having a crystal structure corresponding to that of a catalyst that has been prepared and activated by a process comprising:

reacting a substantially pentavalent vanadium-containing compound with a pentavalent phosphorus-containing compound in an alcohol medium capable of reducing the vanadium to an oxidation state of less than +5;

incorporating molybdenum into the product of the reaction, thereby forming a solid molybdenum-modified precursor composition;

removing the alcohol to produce a dried solid molybdenum-modified precursor composition;

forming shaped bodies comprising said dried solid molybdenum-modified precursor composition and a pore modification agent; and activating the dried formed molybdenum-modified catalyst precursor composition to transform it into the active catalyst, said active catalyst comprising a shaped body having a volume of at least about 0.02 cc, a phosphorus/vanadium atom ratio from about 1.05 to about 1.20, a B.E.T. surface area of at least about 15 $m^2/g$, an average vanadium oxidation state between about 4.06 and about 4.3, a total pore volume of at least about 0.15 g/cc, a normalized apparent shaped body density between about 1.0 and about 2.0 g/cc, and a crush strength of at least about 4 pounds, at least 20% of the pore volume of said catalyst being constituted of pores having a pore diameter between about 0.1 microns and about 3.3 microns, and at least 40% of the pore volume being constituted of pores having a diameter of less than about 0.1 microns.

27. An active catalyst having a crystal structure corresponding to that of a catalyst that has been prepared and activated by a process comprising:

reacting a substantially pentavalent vanadium-containing compound with a pentavalent phosphorus-containing compound in an alcohol medium capable of reducing the vanadium to an oxidation state of less than +5;

incorporating molybdenum into the product of the reaction, thereby forming a solid molybdenum-modified precursor composition;

removing the alcohol to produce a dried solid molybdenum-modified precursor composition;

forming shaped bodies comprising said dried solid molybdenum-modified precursor composition and a pore modification agent; and activating the dried formed molybdenum-modified catalyst precursor composition to transform it into the active catalyst, said active catalyst comprising a shaped body having a B.E.T. surface area of at least about 15 $m^2/g$, an average vanadium oxidation state between about 4.0 and about 4.5, a total pore volume of at least about 0.15 g/cc, a normalized apparent shaped body density between about 1.0 and about 2.0 g/cc, and a crush strength of at least about 4 pounds, at least 5% of the pore volume of said catalyst being constituted of pores having a pore diameter of at least about 0.8 microns, and at least 4% of the pore volume being constituted of pores having a diameter of at least about 10 microns.

28. A process for the preparation of an active catalyst, the process comprising the steps of:

preparing a slurry comprising a mixture containing a phosphorus-containing compound, a pentavalent vanadium-containing compound and an alcohol medium capable of reducing the vanadium to an oxidation state of less than +5;

heating said mixture such that said vanadium-containing compound is reduced by said alcohol and reacts with said phosphorus-containing compound in said slurry to form a solid vanadium/phosphorus oxide precursor composition comprising mixed oxides of vanadium and phosphorus;

cooling said mixture after formation of said solid vanadium/phosphorus oxide precursor composition;

introducing a source of molybdenum into the cooled mixture containing said solid vanadium/phosphorus oxide precursor composition, and heating a slurry containing molybdenum and said solid vanadium/phosphorus oxide precursor composition to effect incorporation of molybdenum and formation of a solid molybdenum-modified precursor composition;

removing the alcohol to produce a dried solid molybdenum-modified precursor composition;

forming shaped bodies comprising said dried solid molybdenum-modified precursor composition; and activating the dried formed molybdenum-modified catalyst precursor composition to transform it into the active catalyst.

29. A process for the preparation of an active catalyst, the process comprising the steps of:

preparing a slurry comprising a mixture containing a phosphorus-containing compound, a pentavalent vanadium-containing compound and an alcohol medium capable of reducing the vanadium to an oxidation state of less than +5;

heating said mixture such that said vanadium-containing compound is reduced by said alcohol and reacts with said phosphorus-containing compound in said slurry to form a solid particulate vanadium/phosphorus oxide precursor composition comprising mixed oxides of vanadium and phosphorus;

removing a portion of said alcohol medium from said mixture after formation of said solid vanadium/phosphorus oxide precursor composition; and after removal of said portion of said alcohol, introducing a source of molybdenum into the mixture containing said solid vanadium/phosphorus oxide precursor compositions incorporating molybdenum into the particulate vanadium/phosphorus oxide precursor, thereby forming a molybdenum-modified precursor composition;

removing alcohol to produce a dried solid molybdenum-modified precursor composition;

forming shaped bodies comprising said dried solid molybdenum-modified precursor composition; and activating the dried formed molybdenum-modified precursor composition to transform into the active catalyst.

30. A fixed catalyst bed as set forth in claim 6 wherein said second catalyst zone comprises shaped bodies of phosphorus vanadium oxide catalyst having an individual catalyst body volume of at lout about 0.02 cc and a B.E.T. surface area of at least about 15 $m^2/g$.

31. A fixed catalyst bed gap adapted for the production of maleic anhydride by passage therethrough of a gas stream initially comprising a mixture of a nonaromatic hydrocarbon having at least four carbon atoms in a straight chain and an oxygen containing gas, said catalyst bed comprising:

a first zone containing a phosphorous vanadium oxide catalyst substantially devoid of active sites comprising molybdenum; and second zone downstream of said first zone with respect to the flow of said gas stream, said second zone comprising shaped bodies of phosphorus vanadium oxide catalyst containing molybdenum in a molybdenum to phosphorus-ratio of between about 0.0020 and about 0.0060 and having an individual catalyst body volume of at least about 0.02 cc and a B.E.T. surface area of at least about 15 $m^2/g$.

32. A catalyst as set forth in claim 25 wherein the dried formed molybdenum-modified catalyst precursor composition is activated by the steps of:

(a) heating the dried formed molybdenum-modified catalyst precursor composition in an atmosphere selected from the group consisting of air, steam, inert gas, and mixtures thereof, to a temperature not to exceed 300° C.;

(b) maintaining the dried formed molybdenum-modified catalyst precursor composition at the temperature of Step (a) and providing an atmosphere containing molecular oxygen, steam, and optionally an inert gas, the atmosphere being represented by the formula $$(O_2)_x(H_2O)_y(IG)_z$$

wherein IG is an inert gas and x, y, and z represent mol percent of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere;

(c) increasing the temperature of the dried formed molybdenum-modified catalyst precursor composition at a programmed rate of from about 2° C./min to about 12° C./min to a value effective to eliminate the water of hydration from the dried formed molybdenum-modified catalyst precursor composition;

(d) adjusting the temperature from Step (c) to a value greater than 350° C., but less than 550° C., and maintaining the adjusted temperature in the molecular oxygen/steam-containing atmosphere for a time effective to provide a vanadium oxidation state of from about +4.0 to about +4.5; and (e) continuing to maintain the adjusted temperature in a nonoxidizing, steam-containing atmosphere for a time effective to complete the dried formed molybdenum-modified catalyst precursor composition to active catalyst transformation to yield the active catalyst.

33. An active catalyst as set forth in claim 24 wherein said mixture is heated to a reflux temperature ranging from about 90° C. to about 120° C. and maintained at the reflux temperature until said vanadium-containing compound is substantially exhausted by reaction with said pentavalent phosphorus-containing compound.

34. An active catalyst as set forth in claim 33 wherein the phosphorus containing compound and the vanadium-containing compound are reacted at a P/V ratio between about 1.05 and about 1.15.

35. An active catalyst as set forth in claim 24 wherein said mixture is cooled below about 50° C. before introduction of the molybdenum-containing compound.

36. An active catalyst as set forth in claim 24 wherein said molybdenum-containing slurry is heated at a reflux temperature between about 90° C. and about 120° C.

37. An active catalyst as set forth in claim 24 wherein said molybdenum-containing compound is a slurry of a molybdenum-containing powder in a solvent.

38. An active catalyst as set forth in claim 24 wherein said molybdenum-containing compound is a molybdenum salt dissolved in a solvent.

39. An active catalyst as set forth in claim 25 wherein preparation of said catalyst further comprises heating a slurry containing molybdenum and said solid vanadium/phosphorus oxide precursor composition to effect incorporation of molybdenum and formation of a molybdenum-modified precursor composition.

40. An active catalyst as set forth in claim 25 wherein preparation of said catalyst further comprises settling said slurry such that said alcohol medium separates from said vanadium/phosphorus oxide precursor composition, and decanting said alcohol portion from said vanadium/phosphorus oxide precursor composition to provide a P/V ratio between about 1.055 and about 1.135.

41. An active catalyst as set forth in claim 40 wherein preparation of said catalyst further comprises stripping part of said alcohol medium from said slurry before said slurry is settled.

42. An active catalyst as set forth in claim 41 wherein preparation of said catalyst further comprises cooling said slurry before said slurry is settled.

43. An active catalyst as set forth in claim 42 wherein said slurry is cooled below about 50° C.

44. An active catalyst as set forth in claim 39 wherein said molybdenum-containing slurry is heated at a reflux temperature between about 90° C. and about 120° C.

45. An active catalyst as set forth in claim 25 wherein said dried solid molybdenum-modified precursor composition corresponds to the formula:

$$VO(Mo)_m HPO_4 \cdot aH_2O \cdot b(P_{2/c}O) \cdot n(\text{organics})$$

wherein m is a number from about 0.0020 to about 0.0060, a is a number of at least about 0.5, b is a number taken to provide a P/V atom ratio of from about 1.0 to about 1.2, c is a number representing the oxidation number of phosphorus and has a value of 5, and n is a number taken to represent the weight % of intercalated organics component, and said dried solid molybdenum-modified precursor composition is transformed into an active catalyst represented by the formula:

$$(VO)_2 Mo_m P_2 O_7 \cdot b(P_{2/c}O)$$

wherein m, b and c are as defined above.

46. An active catalyst as set forth in claim 26 wherein pores having a diameter between about 0.1 microns and about 3.3 microns constitute between about 25% and about 60% of the total pore volume of said active catalyst.

47. An active catalyst as set forth in claim 46 wherein pores having a diameter between about 0.1 microns (μm) and about 3.3 microns constitute between about 30% and about 50% of the total pore volume of said active catalyst.

48. An active catalyst as set forth in claim 46 wherein pores having a diameter between about 0.2 and about 2 μm constitute between about 10% and about 40% of the total pore volume of the active catalyst, and pores having a diameter of between about 0.5 and about 1.2 μm constitute between about 5% and about 20% of the total pore volume.

49. An active catalyst as set forth in claim 48 wherein pores having a diameter between about 0.2 and about 2 μm constitute between about 12% and about 30% of the total pore volume of the active catalyst, and pores having a diameter of between about 0.5 and about 1.2 μm constitute between about 7% and about 12% of the total pore volume.

50. An active catalyst as set forth in claim 48 wherein pores having a diameter of less than about 0.1 microns constitute between about 40% and about 70% of the total pore volume of said active catalyst.

51. An active catalyst as set forth in claim 26 wherein said shaped body comprising said active catalyst has exit holes having a diameter of at least 2 microns at the external surfaces thereof, said holes being present in a density of at least about 75 surface holes per mm$^2$, said holes being in communication with the body interior.

52. An active catalyst as set forth in claim 26 wherein said shaped body comprises an opening therethrough for flow of reactant and product gases when the active catalyst is used in the manufacture of maleic anhydride.

53. An active catalyst as set forth in claim 52 wherein said shaped body comprises a cylinder having a bore therethrough.

54. An catalyst as set forth in claim 27 wherein each of the shaped bodies comprising said catalyst has exit holes having a diameter of at least 2 microns at the external surfaces thereof, said holes being present in a density of at least about 100 surface holes per $mm^2$, said holes being in communication with the body interior.

55. An active catalyst as set forth in claim 27 wherein the average oxidation state of the vanadium is between about 4.06 and about 4.30.

56. An active catalyst as set forth in claim 27 wherein pores having a diameter of greater than about 0.8 microns constitute at least about 8% of the total pore volume of said catalyst.

57. An active catalyst as set forth in claim 56 wherein pores having a diameter of greater than about 0.8 microns constitute between about 8% and about 50% of the total pore volume of said catalyst.

58. An active catalyst as set forth in claim 57 wherein pores having a diameter of greater than about 10 microns constitute between about 6% and about 40% of the total pore volume of said catalyst.

59. A process as set forth in claim 29 wherein said shaped bodies are formed by a process including the steps of:

forming a particulate phosphorus/vanadium oxide catalyst precursor composition from said dried solid molybdenum-modified precursor composition;

preparing a pore-modified catalyst precursor composition comprising a mixture of the particulate phosphorus/vanadium oxide catalyst precursor composition and a pore modification agent in proportions sufficient to provide a pore modification agent concentration of from about 4% to about 16% by weight, said pore modification agent being subject to vaporization, decomposition and/or oxidation at a temperature below 300° C. without leaving a substantial residue;

forming said pore-modified catalyst precursor composition into a predetermined shape under compression, thereby producing said shaped bodies comprising said pore-modified catalyst precursor composition and containing said pore modification agent, said shaped bodies being porous; and heating said shaped bodies while passing a stripping gas comprising air thereover for removal of at least about 80% by weight of said pore modification agent at a temperature not greater than about 300° C., said shaped bodies being heated at a rate of between about 10 and about 3° C. per minute to a hold temperature that is below a threshold temperature at which the pore modification agent is subject to catalytic oxidation in the presence of said pore-modified catalyst precursor composition, to form said dried formed solid molybdenum-modified precursor composition.

60. A process as set forth in claim 59 wherein said pore modification agent has a vapor pressure of at least about 1 mm Hg at a temperature between about 150° C. and about 260° C.

61. A process as set forth in claim 59 wherein the pore modification agent concentration of from about 8% to about 16% by weight.

62. A process as set forth in claim 60 wherein said shaped porous body is heated to a temperature between about 150° C. and about 260° C. for removal of said pore modification agent.

63. A process as set forth in claim 59 wherein the stripping gas flows over the precursor body at a linear rate of at least about 25 cm/sec.

64. A process as set forth in claim 59 wherein the stripping gas containing at least about 5% by volume water vapor when the temperature of said catalyst body is above the temperature at which the vapor pressure of the pore modification agent is 1 mm Hg.

65. A process as set forth in claim 64 wherein the stripping gas contains between about 20% and about 80% by volume water vapor when the temperature of said catalyst body is above the temperature at which said pore modification agent has a vapor pressure of 1 mm Hg.

66. A process as set forth in claim 59 wherein the composition of said stripping gas is such that no reaction that may occur between said agent and any component of said gas generates an exotherm sufficient to heat said body to a temperature of greater than 300° C.

67. A process as set forth in claim 59 wherein oxygen is incorporated in said stripping gas so that, after 90% of said pore modification agent has been removed from said body, the proportion of oxygen in said gas is sufficient to prevent reduction of the average oxidation state of vanadium in said precursor body to less than about 3.8 but not sufficient to create a flammable mixture in said stripping gas.

68. A process as set forth in claim 63 wherein said pore modification agent substantially comprises stearic acid, and said hold temperature is between about 160° C. and about 170° C.

69. A process as set forth in claim 63 wherein said shaped bodies are heated from said hold temperature to a terminal temperature at which the concentration of residual pore modification agent in the shaped body has been reduced to a terminal level, the terminal level being defined as a concentration of residual pore modification agent which does not result in an exotherm that adversely alters the catalyst structure upon subsequent transformation of the dried formed molybdenum-modified catalyst precursor composition to active catalyst by heat treatment of said shaped bodies in the presence of air, steam or nitrogen under reference conditions, such reference conditions comprising heating said precursor at a rate of 1.8° C. between 300° C. and 400° C.

70. A process as set forth in claim 69 wherein said shaped bodies are heated from said hold temperature at a rate of between about 0.5° C. and about 2° C. per hour in a temperature range between about 15° C. and 40° C. above the hold temperature.

71. A process as set forth in claim 70 wherein said shaped bodies are heated at a rate of between about 10° C. and about 40° C. per minute between a temperature of about 200° C. and said terminal temperature.

72. A process as set forth in claim 71 wherein said terminal temperature is between about 240° C. and about 260° C.

73. A process as set forth in claim 72 wherein said shaped bodies are cooled from said terminal temperature to ambient temperature within about 0.5 to about 2 hours.

74. A process as set forth in claim 59 wherein said pore modification agent is removed by vaporization.

75. A process as set forth in claim 59 wherein said pore modification agent is recovered and reused in the preparation of further shaped bodies comprising said dried solid molybdenum-modified precursor composition.

76. A process as set forth in claim 74 wherein said pore modification agent has a vapor pressure of at least about 1 mm Hg at a temperature below 300° C., and said pore modification agent is removed by passing a stripping gas over said shaped bodies at a temperature at which said vapor pressure is at least about 1 mm Hg.

77. A process as set forth in claim 59 wherein essentially complete removal of said pore modification agent is provided, without reduction of vanadium in said pore-modified catalyst precursor composition to an average oxidation state of less than about 3.8.

78. A process as set forth in claim 77 wherein said pore modification agent has a vapor pressure of at least about 1 mm Hg at a temperature below the temperature at which oxygen atoms in said pore-modified catalyst precursor composition are labile and subject to abstraction.

79. A process as set forth in claim 59 wherein said pore modification agent is selected from the group consisting of fatty acids, fatty acid esters, and polynuclear organic compounds.

80. A process as set forth in claim 59 wherein said pore modification agent is removed by oxidation or decomposition at a temperature below 300° C.

81. A process as set forth in claim 59 wherein said particulate phosphorus/vanadium oxide catalyst precursor composition is mixed with a particulate pore modification agent, the mean particle diameter of said pore modification agent being not greater than about two orders of magnitude different from the mean particle diameter of said particulate phosphorus/vanadium oxide catalyst precursor composition.

82. A process as set forth in claim 81 wherein said pore modification agent has a mean particle diameter of between about 50 and about 2000 microns.

83. A process as set forth in claim 82 wherein said pore modification agent has a mean particle diameter of between about 100 and about 550 microns.

84. A process as set forth in claim 81 wherein said pore modification agent has a mean particle diameter of between about 10 and about 500 microns.

85. A process as set forth in claim 84 wherein said pore modification agent has a mean particle diameter of between about 30 and about 90 microns.

86. A process as set forth in claim 85 wherein said particulate phosphorus/vanadium oxide catalyst precursor composition has a mean particle diameter of between about 20 and about 200 microns.

87. A process as set forth in claim 59 wherein, after removal of said pore modification agent, said shaped bodies are heated at a temperature above 300° C. to transform said shaped bodies to a phosphorus/vanadium oxide catalyst body active for the oxidation of a hydrocarbon to maleic anhydride.

88. A process as set forth in claim 59 wherein transformation of said dried formed molybdenum-modified catalyst precursor composition to said active catalyst comprises the steps of:

(a) heating said dried formed molybdenum-modified catalyst precursor composition in an atmosphere selected from the group consisting of air, steam, inert gas, and mixtures thereof to a temperature not to exceed about 300° C., thereby removing said pore modification agent from said dried formed molybdenum-modified catalyst precursor composition substantially at a temperature below 300° C.;

(b) maintaining the catalyst precursor body at the temperature of Step (a) and providing an atmosphere containing molecular oxygen, steam, and optionally an inert gas, the atmosphere being represented by the formula

$(O_2)_x(H_2O)_y(IG)_z$ wherein IG is an inert gas and x, y, and z represent mol percent of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere;

(c) increasing the temperature of the catalyst precursor body at a programmed rate of from about 2° C./min to about 12° C./min to a value effective to eliminate the water of hydration from the catalyst precursor body;

(d) adjusting the temperature from Step (c) to a value greater than 350° C., but less than 550° C., and maintaining the adjusted temperature in the molecular oxygen/steam-containing atmosphere for a time effective to provide a vanadium oxidation state of from about +4.06 to about +4.3; and (e) continuing to maintain the adjusted temperature in a nonoxidizing, steam-containing atmosphere for a time effective to complete the catalyst precursor body-to-active catalyst transformation to yield the active catalyst.

89. A process as set forth in claim 88 wherein transformation of said catalyst precursor body to said active catalyst is carried out after removal of said pore modification agent from said dried formed solid molybdenum-modified precursor composition.

90. A process as set forth in claim 88 wherein step (a) produces a catalyst precursor body having a pore volume of at least about 0.15 cc/g, at least about 25% of the pore volume of said catalyst precursor body being constituted of pores having a diameter between about 0.1 microns and about 3.3 microns, and at least about 40% of the pore volume being constituted of pores having a diameter of less than about 0.1 microns.

91. A process as set forth in claim 88 wherein step (a) produces a catalyst precursor body having a pore volume of at least about 0.15 cc/g, at least about 5% of the pore volume of said catalyst precursor being constituted of pores having a diameter of at least about 0.8 microns, and at least about 4% of the pore volume being constituted of pores having a diameter of at least about 10 microns.

92. A process as set forth in claim 88 wherein said pore modification agent is removed during Step (c) of said transformation.

93. A process as set forth in claim 92 wherein oxygen in a proportion of between about 0.1 and about 1.5% by volume is included in said atmosphere during an initial heating period of between about 0.5 and about 10 hours, and thereafter the oxygen content of said atmosphere is increased to between about 2.0 and about 5% by volume.

94. A process as set forth in claim 93 wherein said atmosphere contains at least about 5% by volume water vapor when in said initial heating period the temperature of said catalyst body is above the temperature at which the vapor pressure of the pore modification agent is 1 mm Hg.

95. A process as set forth in claim 59 wherein said pore modification agent has a melting point of between about 35° and about 100° C., and a vapor pressure greater than 1 mm Hg at a temperature below 300° C.

96. A process as set forth in claim 88 wherein said dried formed solid molybdenum-modified precursor composition is heated in the presence of said stripping gas until an end point at which at least about 80% of said pore modification agent has been removed from said catalyst precursor body, the terminal temperature of said catalyst body at said end point being at least 200° C., and said catalyst precursor body is not cooled below about 100° C. during the period after said end point and prior to Step (a) of the transformation of said catalyst precursor body to an active catalyst.

97. A process as set forth in claim 96 wherein said catalyst precursor body is not cooled by more than 50° C. below said terminal temperature after said end point and prior to Step (a).

98. A process as set forth in claim 88 in which the pore modification agent is removed from said catalyst precursor body by passing said stripping gas over said catalyst precursor body in an oven, and transformation of said catalyst precursor body to active catalyst is carried out in the same oven without removal of the catalyst precursor body from the oven in the period between said end point and Step (a).

99. A process-as set forth in claim 28 wherein said mixture is cooled below about 50° C. before introduction of the molybdenum-containing compound.

100. A process as set forth in claim 28 wherein said molybdenum-containing slurry is heated at a reflux temperature between about 90° C. and about 120° C.

101. A process as set forth in claim 28 wherein said molybdenum-containing compound is a slurry of a molybdenum-containing powder in a solvent.

102. A process as set forth in claim 28 wherein said molybdenum-containing compound is a molybdenum salt dissolved in a solvent.

103. A process as set forth in claim 28 wherein preparation of said catalyst further comprises heating a slurry containing molybdenum and said solid vanadium/phosphorus oxide precursor composition to effect incorporation of molybdenum and formation of a molybdenum-modified precursor composition.

104. A process as set forth in claim 28 wherein preparation of said catalyst further comprises settling said slurry such that said alcohol medium separates from said vanadium/phosphorus oxide precursor composition, and decanting said alcohol portion from said vanadium/phosphorus oxide precursor composition to provide a P/V ratio between about 1.055 and about 1.135.

105. A process as set forth in claim 104 wherein preparation of said catalyst further comprises stripping part of said alcohol medium from said slurry before said slurry is settled.

106. A process as set forth in claim 105 by wherein preparation of said catalyst further comprises cooling said slurry before said slurry is settled.

107. A process as set forth in claim 106 wherein said slurry is cooled below about 50° C.

108. A process as set forth in claim 103 wherein said molybdenum-containing slurry is heated at a reflux temperature between about 90° C. and about 120° C.

* * * * *